US012016948B2

(12) United States Patent
Wang et al.

(10) Patent No.: US 12,016,948 B2
(45) Date of Patent: Jun. 25, 2024

(54) MICROMOTORS AND NANOMOTORS FOR GASTROINTESTINAL DIAGNOSIS AND TREATMENT APPLICATIONS

(71) Applicant: The Regents of the University of California, Oakland, CA (US)

(72) Inventors: Joseph Wang, San Diego, CA (US); Liangfang Zhang, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/475,894

(22) PCT Filed: Jan. 5, 2018

(86) PCT No.: PCT/US2018/012678
§ 371 (c)(1),
(2) Date: Jul. 3, 2019

(87) PCT Pub. No.: WO2018/129390
PCT Pub. Date: Jul. 12, 2018

(65) Prior Publication Data
US 2019/0343758 A1 Nov. 14, 2019

Related U.S. Application Data

(60) Provisional application No. 62/505,812, filed on May 12, 2017, provisional application No. 62/443,516, filed on Jan. 6, 2017.

(51) Int. Cl.
*A61K 9/46* (2006.01)
*A61K 9/00* (2006.01)
*A61K 9/20* (2006.01)
*A61K 9/48* (2006.01)
*A61K 9/50* (2006.01)
*A61B 5/00* (2006.01)

(52) U.S. Cl.
CPC .......... *A61K 9/0007* (2013.01); *A61K 9/0053* (2013.01); *A61K 9/2009* (2013.01); *A61K 9/2027* (2013.01); *A61K 9/204* (2013.01); *A61K 9/205* (2013.01); *A61K 9/2086* (2013.01); *A61K 9/4808* (2013.01); *A61K 9/4866* (2013.01); *A61K 9/501* (2013.01); *A61K 9/5026* (2013.01); *A61K 9/5031* (2013.01); *A61K 9/5036* (2013.01); *A61B 5/4222* (2013.01)

(58) Field of Classification Search
None
See application file for complete search history.

(56) References Cited

U.S. PATENT DOCUMENTS

| 7,157,102 | B1 * | 1/2007 | Nuwayser | A61K 9/167 424/463 |
| 9,347,143 | B2 | 5/2016 | Wang et al. | |
| 9,352,963 | B2 | 5/2016 | Wang et al. | |
| 2008/0156654 | A1 | 7/2008 | Wang et al. | |
| 2013/0084569 | A1 | 4/2013 | Wang et al. | |
| 2013/0241344 | A1 | 9/2013 | Wang | |
| 2014/0045179 | A1 | 2/2014 | Wang et al. | |
| 2015/0013304 | A1 | 1/2015 | Wang et al. | |

OTHER PUBLICATIONS

Li et al., Enteric Micromotor Can Selectively Position and Spontaneously Propel in the Gastrointestinal Tract, American Chemical Society Nano, vol. 10, Sep. 20, 2016, pp. 9536-9542.*
Gao et al. (I) (Nanoscale, 2014, 6, 10486-10494).*
Gao et al. (Nanoscale, 2013, 5, 4696-4700).*
Zhang et al. (Nature Materials, 14, 1065-1071, 2015).*
Mitra et al. (Indian J. Pharm. Sci., 2011, 73 (4): 355-366).*
Thagale et al. (Int. J. of Pharm. & Life Sci. (IJPLS), vol. 2, Issue 1: Jan. 2011, 510-515).*
Avila, et al. "Micromotor-enabled active drug delivery for in vivo treatment of stomach infection" Nature Communications 8(272), 9 pages.
Gao et al. "Artificial Micromotors in the Mouse's Stomach: A Step toward in Vivo Use of Synthetic Motors" ACS Nano, 2015, 9(1), pp. 117-123.
ISA, International Search Report and Written Opinion for International Application No. PCT/US2018/012678. Mail Date: Mar. 8, 2018. 10 pages.
Torreggiani et al., "Copper (II)-Quercetin complexes in aqueous solutions: spectroscopic and kinetic properties," Journal of Molecular Structure, 2005; 744-747: pp. 759-766.
Turnlund et al., "A stable isotope study of copper absorption I young men: effect of phytate and α-cellulose[1-3]," The American Journal of Clinical Nutrition, 1985; 42: pp. 18-23.
Walter et al., "Enhanced selectivity for Mg2+ with a phosphinate-based chelate: APDAP versus APTRA," Dalton Transactions, The Royal Society of Chemistry, 2018; 47: pp. 1879-1887.
Deloume et al., "Structure du picolate de magnésium dihydraté," Acta Crystallogr, Section B, Struct. Crystallogr Cryst. Chem., 29(4): 668-676 (1973). (English abstract included).
International Search Report and Written Opinion for PCT/US2017/056228, dated Dec. 22, 2017.

(Continued)

*Primary Examiner* — Tigabu Kassa
(74) *Attorney, Agent, or Firm* — Perkins Coie LLP

(57) ABSTRACT

Disclosed are nano/micromotor devices, systems, and methods for providing payloads in the gastrointestinal system. In one aspect, a micromotor for a gastrointestinal tract includes a micromotor body including a one or more material layers to provide a structure that surrounds a hollow interior region and has an opening to an exterior of the micromotor body; one or more particles including a biocompatible metal element, the one or more particles contained in the interior region of the micromotor body; a coating coupled to the structure of the micromotor body; and a payload material, in which the micromotor is structured to move in a fluid of a gastrointestinal system based on a reaction between the one or more particles and a constituent or a condition of the fluid, such that the reaction generates bubbles that accelerate out of the opening of the micromotor body to propel the micromotor in the fluid.

15 Claims, 26 Drawing Sheets

(56) References Cited

OTHER PUBLICATIONS

ISA, International Preliminary Report on Patentability for International Application No. PCT/US2018/012678. Mail Date: Jul. 18, 2019. 9 pages.
Li et al. "Enteric Micromotor Can Selectively Position and Spontaneously Propel in the Gastrointestinal Tract" American Chemical Society Nano, Sep. 2016, vol. 10, pp. 9536-9542.
Li et al. "Micromotors spontaneously neutralize gastric acid for pH-responsive payload release" Angewandte Chemie International Edition. 2017, 56(8), pp. 2156-2161.
Woods, et al. "Wireless Capsule Endoscope for Targeted Drug Delivery: Mechanics and Design Considerations" IEEE Transactions on Biomedical Engineering, 60(4), Apr. 2013, pp. 945-953.

\* cited by examiner

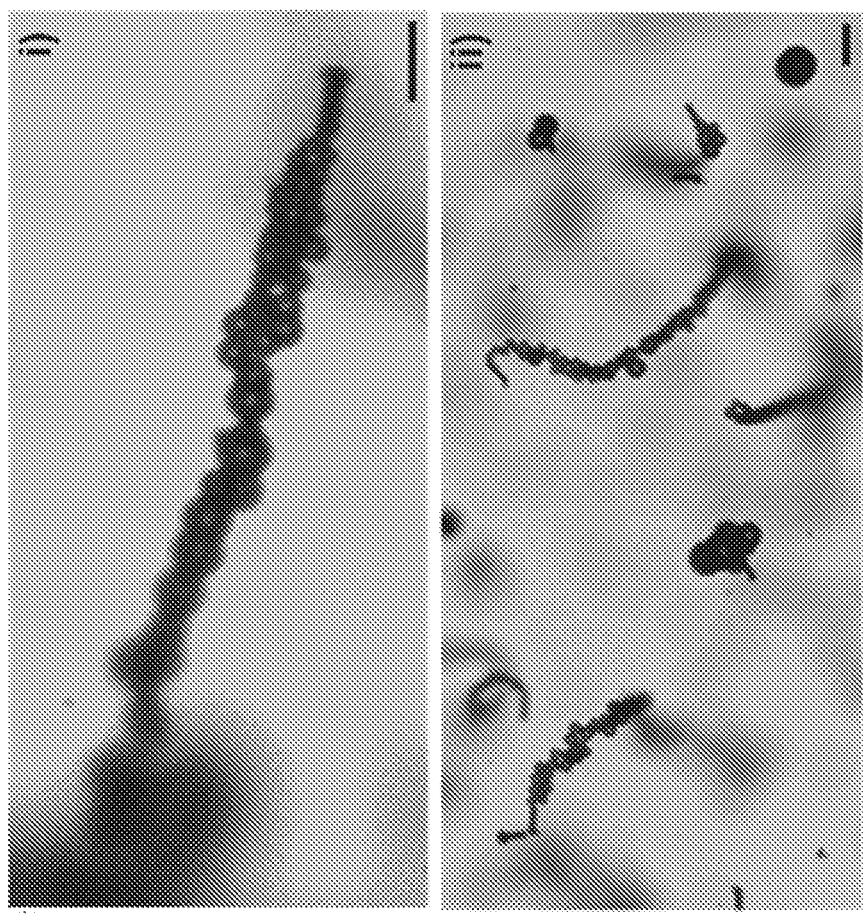
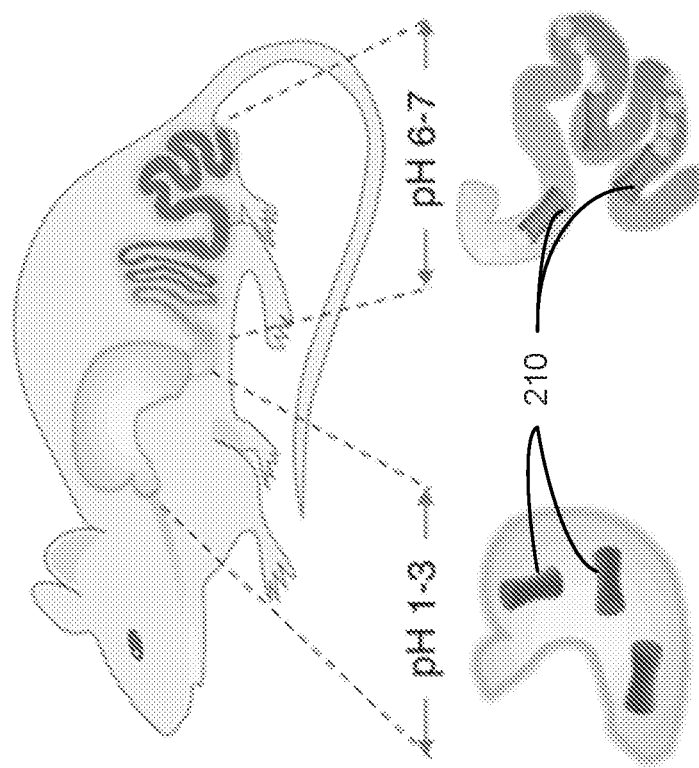
FIG. 2E
FIG. 2A

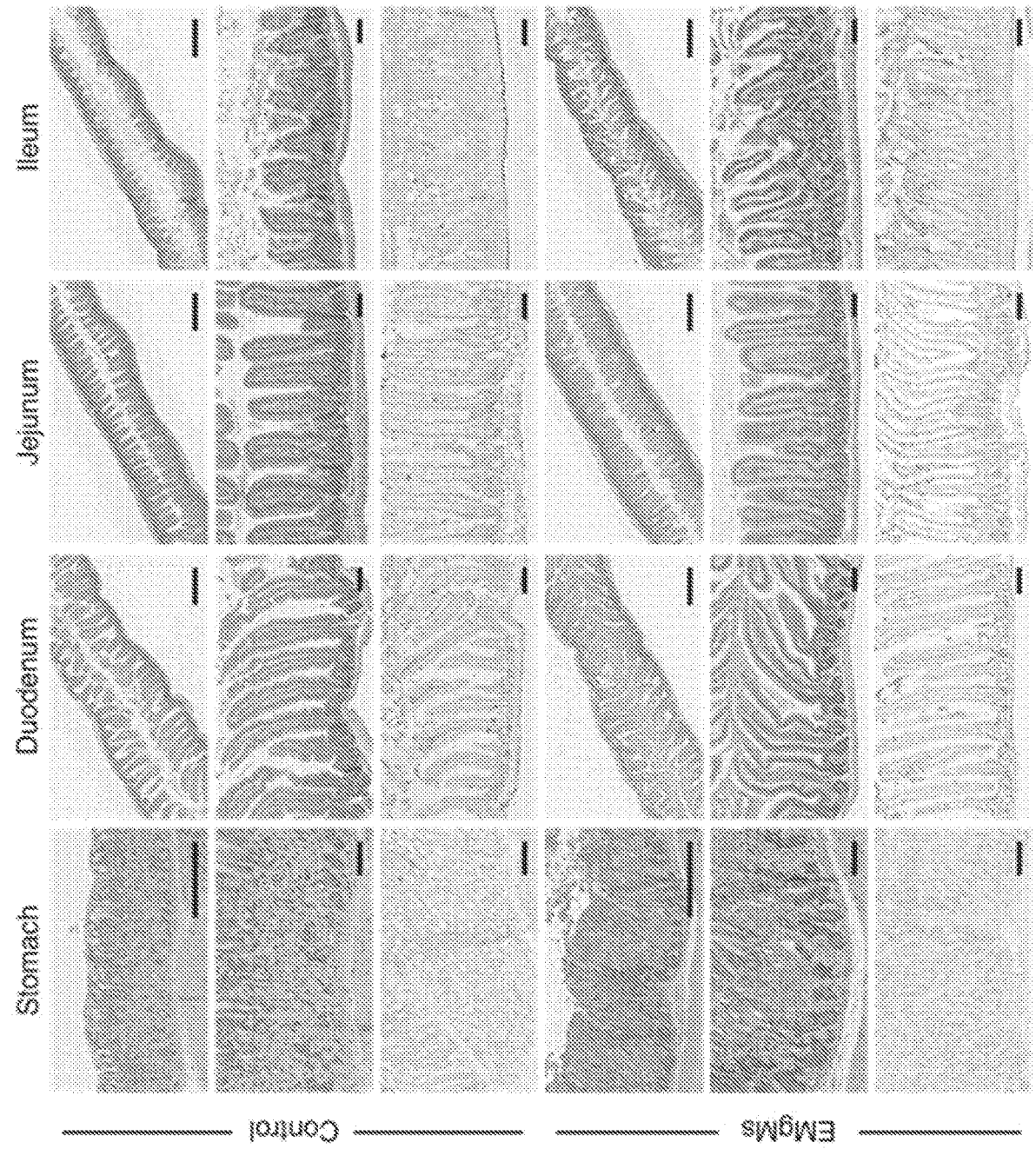

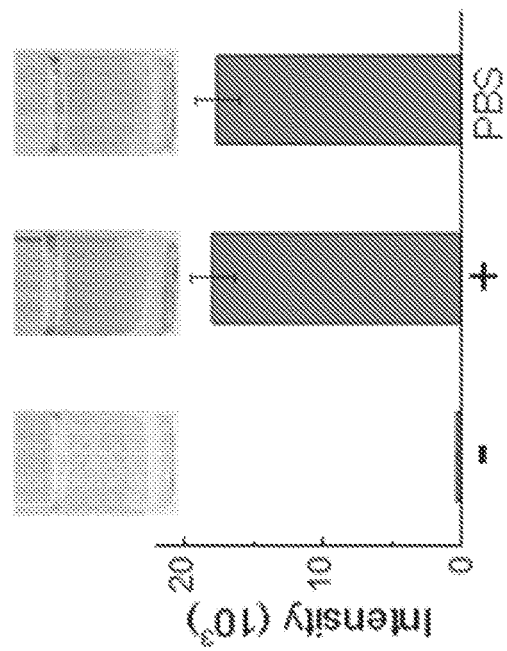
FIG. 7A
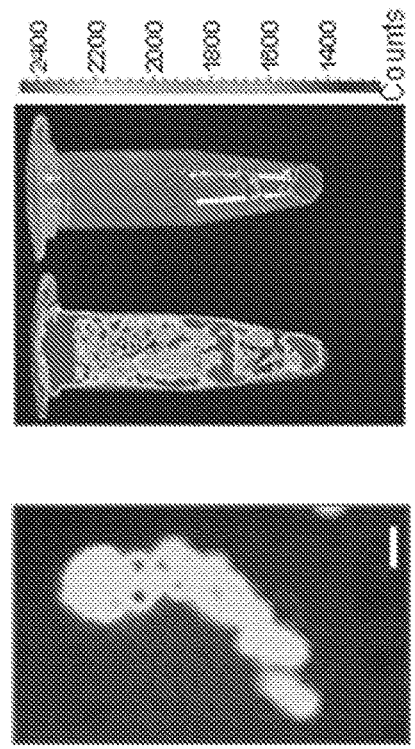
FIG. 7B
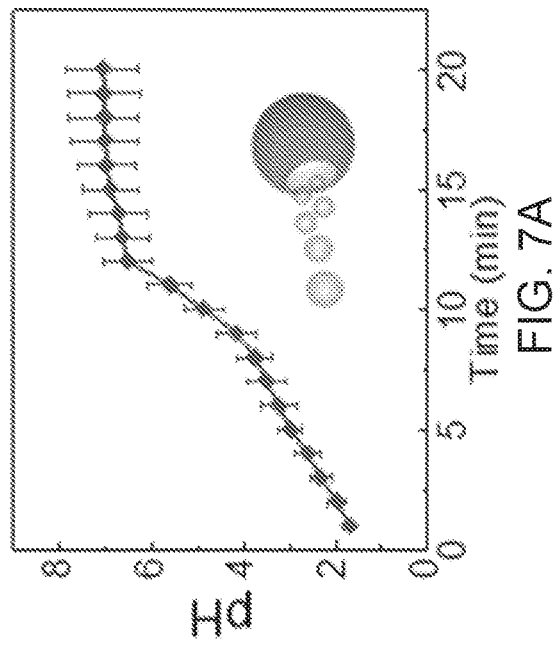
FIG. 7C
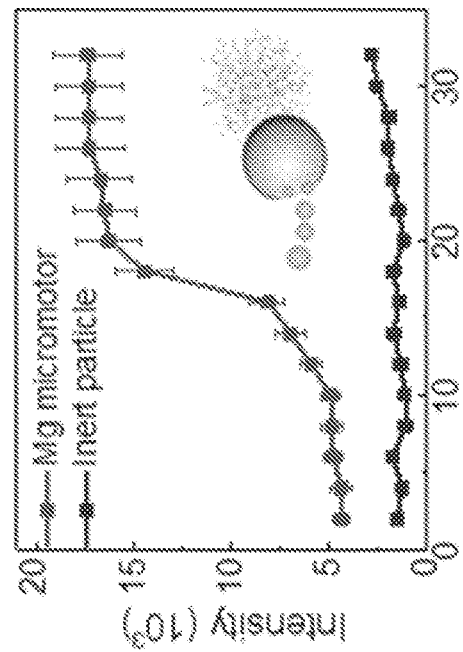
FIG. 7D
FIG. 7E

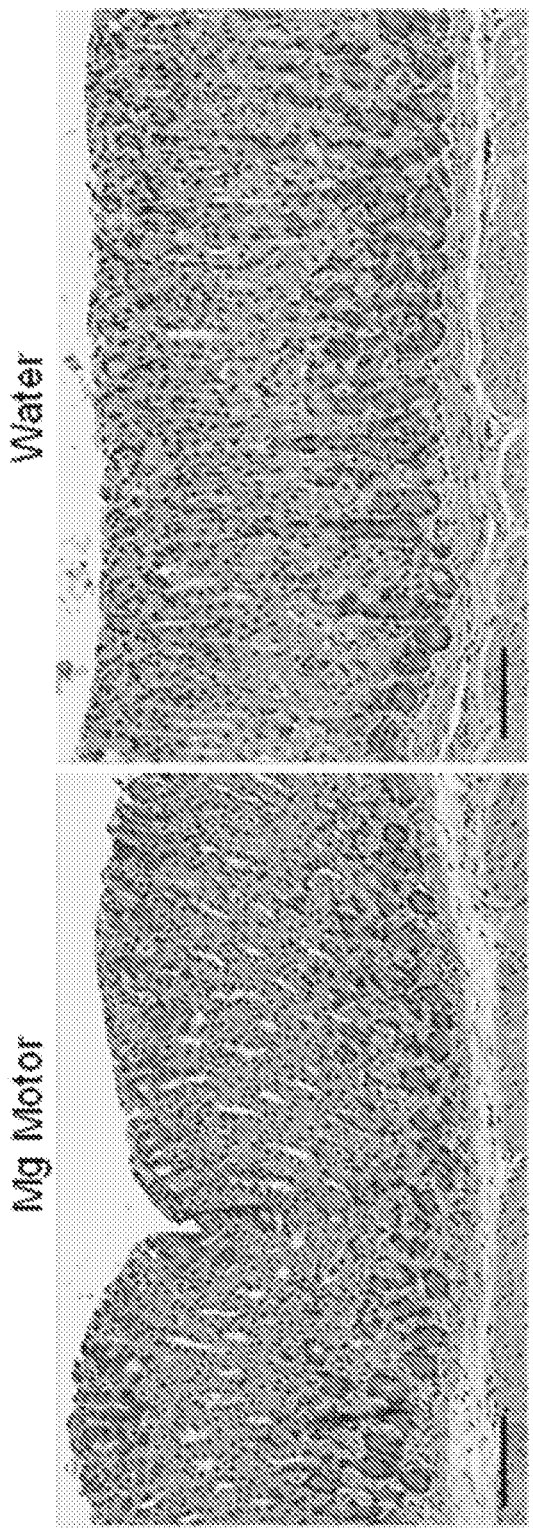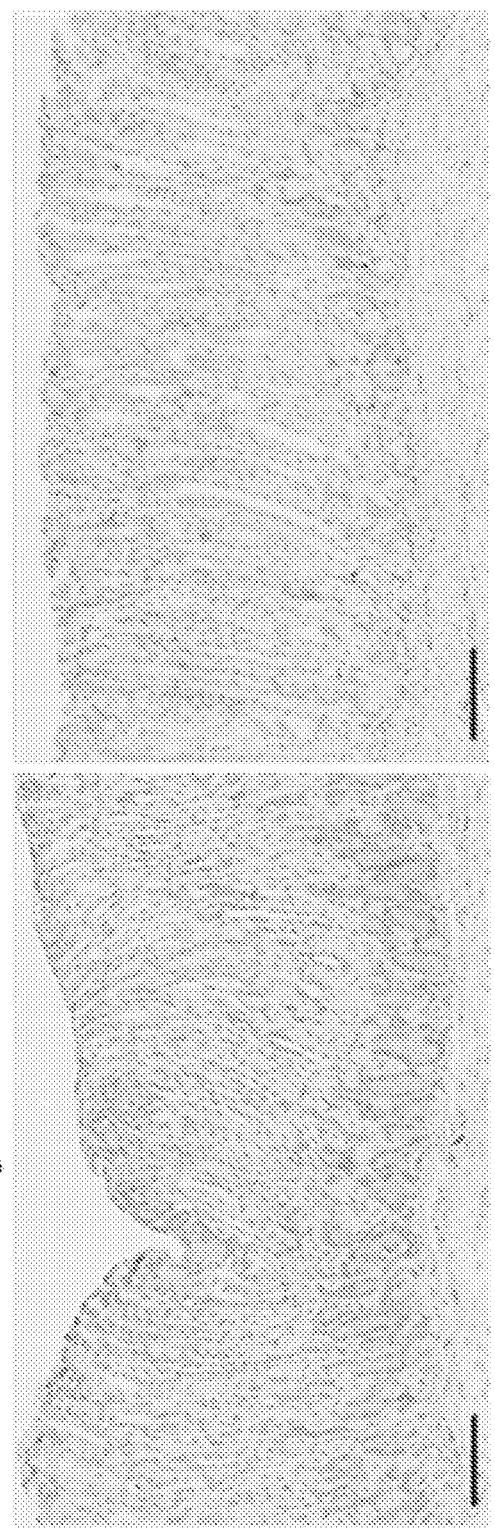
FIG. 10A
FIG. 10B

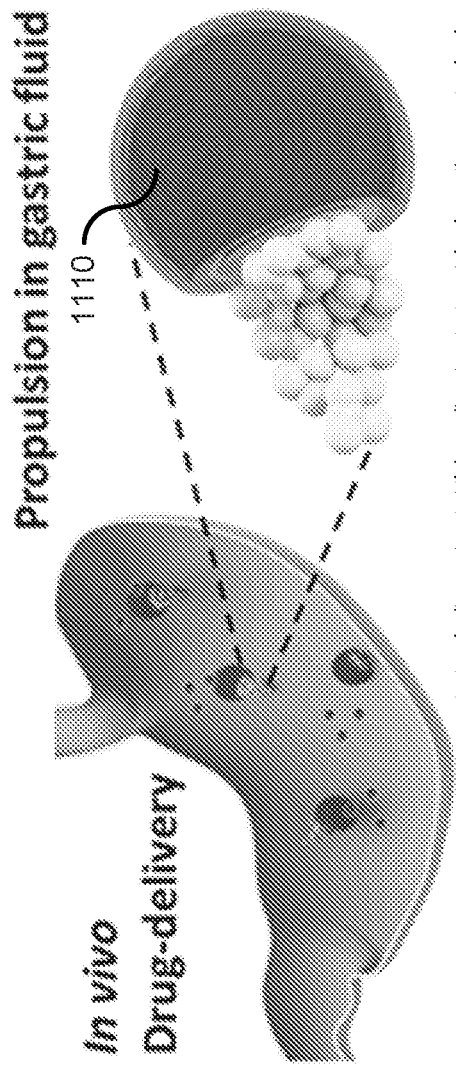
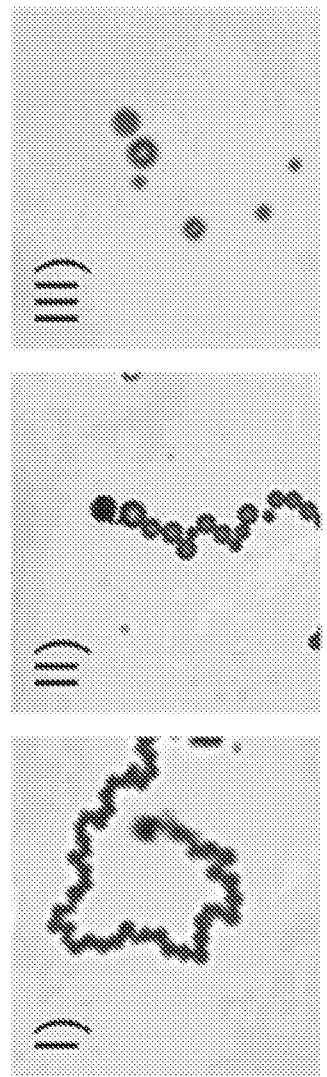
FIG. 11B
FIG. 11C
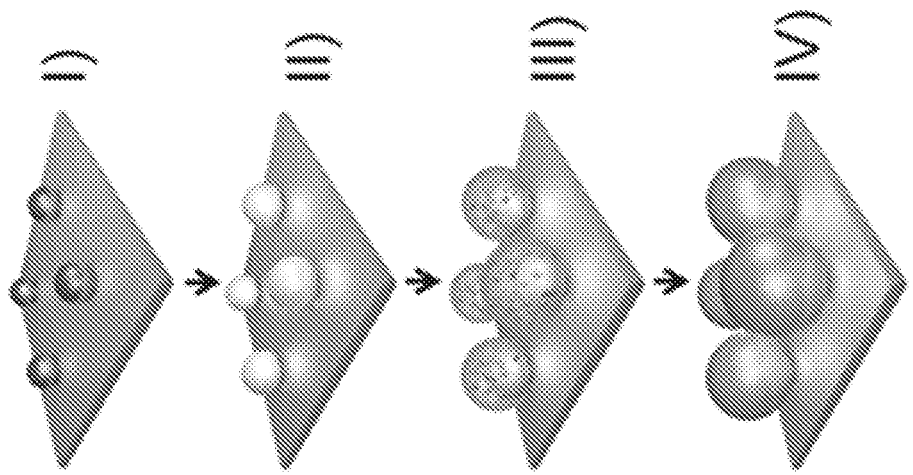
FIG. 11A

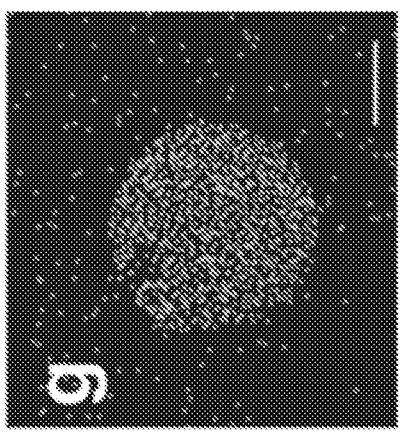
FIG. 11G
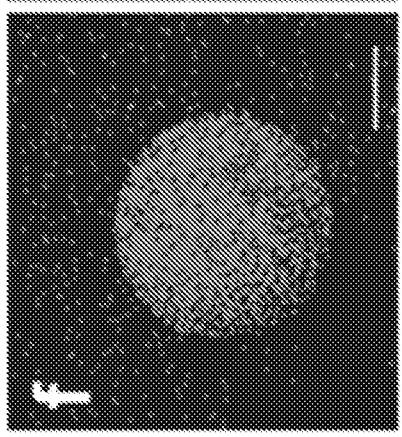
FIG. 11F
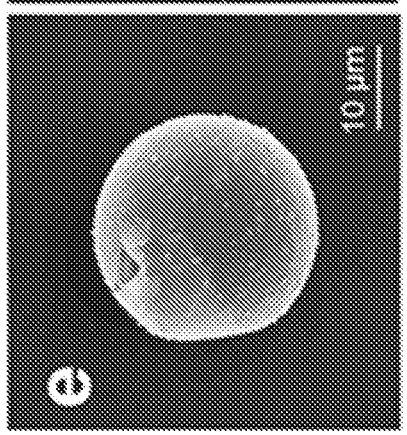
FIG. 11E
FIG. 11D
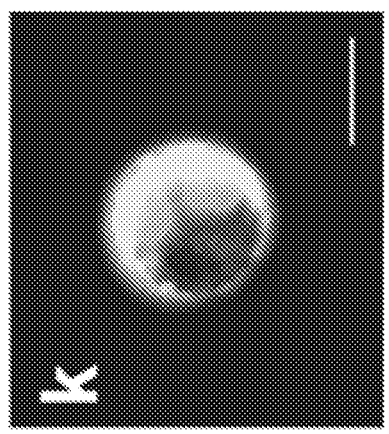
FIG. 11K
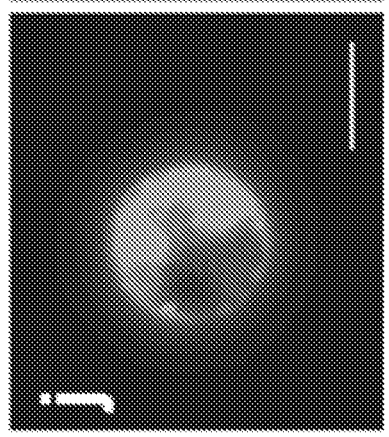
FIG. 11J
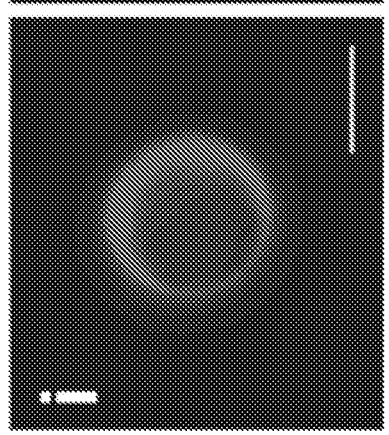
FIG. 11I
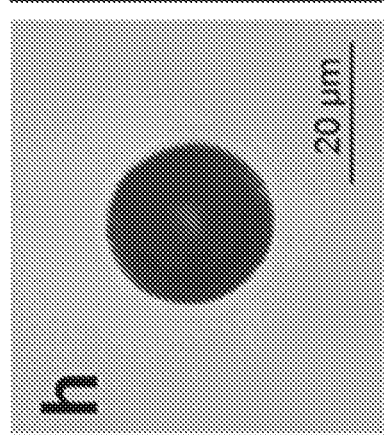
FIG. 11H

MICROMOTORS AND NANOMOTORS FOR GASTROINTESTINAL DIAGNOSIS AND TREATMENT APPLICATIONS

CROSS-REFERENCE TO RELATED APPLICATIONS

This patent document is a 371 National Phase Application of PCT Application No. PCT/US2018/012678 entitled "MICROMOTORS AND NANOMOTORS FOR GASTROINTESTINAL DIAGNOSIS AND TREATMENT APPLICATIONS" filed on Jan. 5, 2018 which claims the priority to and benefits of U.S. Provisional Patent Application No. 62/443,516 entitled "MICROMOTORS FOR NEUTRALIZING GASTRIC ACID AND PH-RESPONSIVE PAYLOAD RELEASE" filed on Jan. 6, 2017, and of U.S. Provisional Patent Application No. 62/505,812 entitled "MICROMOTORS AND NANOMOTORS FOR GASTROINTESTINAL DIAGNOSIS AND TREATMENT" filed on May 12, 2017. The entire contents of the aforementioned patent applications are incorporated by reference as part of the disclosure of this patent document.

FEDERALLY SPONSORED RESEARCH OR DEVELOPMENT

This invention was made with government support HDTRA1-13-1-0002 and HDTRA1-14-1-0064 awarded by Defense Threat Reduction Agency Joint Science and Technology Office for Chemical and Biological Defense, and under R01DK095168 awarded by the National Institute of Diabetes and Digestive and Kidney Diseases of the National Institutes of Health. The government has certain rights in the invention.

TECHNICAL FIELD

This patent document relates to systems, devices, and processes that use micro- and nano-motor technologies.

BACKGROUND

Gastric acid, primarily including hydrochloric acid produced by parietal cells in the gastric glands, plays a role in maintaining the stomach's digestive function. It enables gastric proteolysis by denaturing proteins from food for break down by digestive enzymes. It also inhibits the growth of many microorganisms that enter the stomach and thus reduces the risk of pathogen infection. However, the harsh gastric environment may also create a physiological barrier in the stomach for the use and delivery of therapeutic drugs, such as protein-based drugs and some antibiotics. In these cases, the drugs may be combined with a proton pump inhibitor (PPI), to reduce the production of gastric acid. The effectiveness of PPIs may be due to the irreversible binding to the proton pumps to suppress acid secretion for approximately 12 to 24 hours. Long-term use of PPIs can cause adverse side effects such as headache, diarrhea and fatigue, and in more serious scenarios can cause anxiety and depression, as well as server reaction rhabdomyolysis. Due to these problems, alternative approaches are needed that can temporarily neutralize gastric acid without causing adverse side effects.

SUMMARY

Disclosed are nanoscale and microscale engineered motors, devices, systems and methods for their use and manufacture in gastrointestinal biomedical applications including diagnosis and treatment of disease and dysfunction.

In some embodiments, a micromotor for a gastrointestinal tract includes a micromotor body including a one or more material layers to provide a structure that surrounds a hollow interior region and has an opening to an exterior of the micromotor body; one or more particles including a biocompatible metal element, the one or more particles contained in the interior region of the micromotor body; a coating coupled to the structure of the micromotor body; and a payload material, in which the micromotor is structured to move in a fluid medium of a gastrointestinal system based on a reaction between the one or more particles and a constituent or a condition of the fluid medium, such that the reaction generates bubbles that accelerate out of the opening of the micromotor body to propel the micromotor in the fluid medium.

In some embodiments, an enteric micromotor includes one or more magnesium particles; a microstructure body including an inner layer including gold and an outer layer including a polymer material including poly3,4-ethylenedioxythiophene (PEDOT), in which the microstructure body is structured to include a hollow interior region to contain the one or more magnesium particles and an opening of the microstructure body into the hollow interior region; a polymer layer coupled to the outer layer; and a payload material contained in the hollow interior region of the microstructure body, in which, when the polymer layer is immersed in a solution at a predetermined neutral pH, the one or more magnesium particles reacts with water in the solution to generate hydrogen to propel the enteric micromotor.

In some embodiments, an enteric micromotor includes a magnesium microsphere; a gold coating affixed to the magnesium microsphere; a polymer layer affixed to the gold coating; and a payload material encapsulated by the polymer layer, in which when the polymer layer is immersed in a solution at or below a predetermined acidic pH, the magnesium microsphere reacts with the acidic solution thereby (i) generating hydrogen to propel the enteric micromotor, (ii) depleting protons in the solution thereby increasing the pH of the solution, and (iii) releasing the payload material from the polymer layer.

In some embodiments, a chemical-propulsion microstructure device includes a magnesium microsphere; a coating including titanium oxide affixed to the magnesium microsphere, in which the coating includes an opening at one portion of the magnesium microsphere to expose a magnesium surface; a polymer layer affixed to the coating; and a payload material at least partially encapsulated by the polymer layer, in which the chemical-propulsion microstructure device is operable to undergo a chemical reaction between magnesium and acid when the chemical-propulsion microstructure device are placed in an acidic solution.

Implementations of the example embodiments can include one or more of the following features.

The highly acidic gastric environment may create a physiological barrier for using therapeutic drugs in the stomach. While proton pump inhibitors may block acid-producing enzymes, adverse side effects may occur. In some aspects, an engineered micro-/nano-motor system includes a magnesium-based micromotor that can temporarily neutralize gastric acid through efficient chemical propulsion in the gastric fluid by rapidly depleting localized protons. Coating the example micromotors with a cargo-containing pH-responsive polymer layer may lead to release of the encapsulated payload upon gastric-acid neutralization by the micromotors. For example, micromotors can safely and rapidly neutralize gastric acid in a mouse and release payload without causing noticeable acute toxicity or affecting the stomach function. The normal stomach pH can be restored within 24 hours post micromotor administration.

In some implementations, micro- and/or nano-motor devices (e.g., Mg-based micromotors) can be loaded with an antibiotic drug (e.g., clarithromycin (CLR)) for in vivo treatment of gastrointestinal maladies (e.g., *H. pylori* infection). For example, in implementations, given the built-in proton depletion function, the example micro/nanomotor-based therapy is able to undergo the harsh gastric environment to achieve remarkable antibacterial efficacy without involving the commonly used proton pump inhibitors (PPIs).

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

FIGS. 2A-2E show diagrams and images depicting an implementation of an enteric micromotor system capable of precise positioning and controllable retention in desired segments of the gastrointestinal tract, in accordance with some example embodiments.

FIGS. 5A-5F show images depicting example toxicity evaluations of example enteric micromotors, in accordance with some example embodiments.

FIGS. 7A-7E show data plots and images of example results from implementations using Mg micromotors to neutralize gastric acid and pH-triggered release of a payload, in accordance with some example embodiments.

FIGS. 10A and 10B show images of a toxicity evaluation using example Mg micromotors, in accordance with some example embodiments.

FIGS. 11A-11K show schematic diagrams and example results of example embodiments of drug-loaded Mg-based micromotors in accordance with the present technology.

DETAILED DESCRIPTION

Figure 1A:
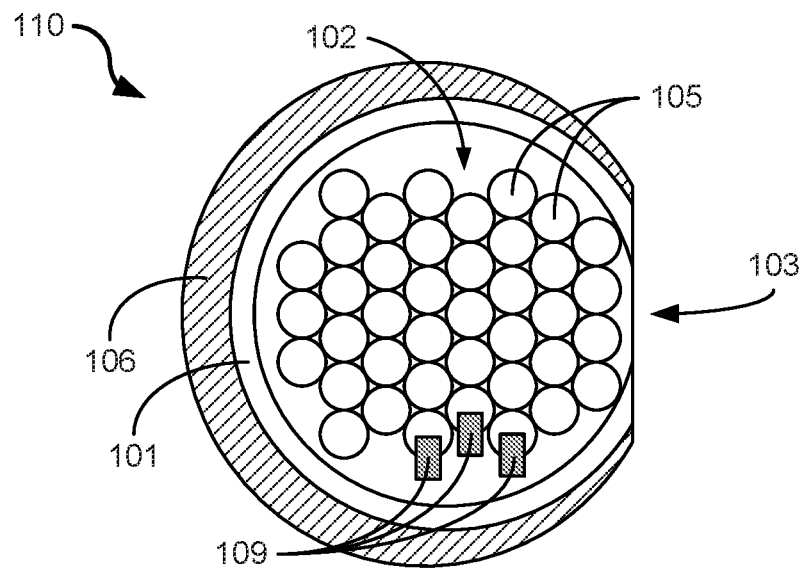
FIGS. 1A-1D show diagrams of an example embodiment of a nano-scale or micro-scale motor for gastrointestinal biomedical applications in accordance with the present technology.

Nanotechnology provides techniques or processes for fabricating structures, devices, and systems with features at a molecular or atomic scale, e.g., structures in a range of one to hundreds of nanometers in some applications. For example, nano-scale devices can be configured to sizes similar to some large molecules, e.g., biomolecules such as enzymes. Nano-sized materials used to create a nanostructure, nanodevice, and/or a nanosystem can exhibit various unique properties, e.g., including optical properties and/or electrical, that are not present in the same materials at larger dimensions and such unique properties can be exploited for a wide range of applications. For example, various nanomotors can be constructed to navigate in body fluids to perform various functions, including carrying substances (e.g., payloads) that can be delivered and/or used to interact with other substances in the environment that the nanomotor navigates. In some embodiments, certain properties of nanomotors can be implemented on structures built on a micro-scale, referred to as micromotors.

Nanomotor and micromotor systems can be designed so that they can respond to various biological stimuli such as pH to trigger the release of a payload chemical, compound, material. Synthetic nano/micromotors including small devices that convert locally supplied fuels or externally provided energy to force and movement may be used as delivery due to their active transport capacity and ability to dynamically respond to their surroundings. These delivery vehicles may deliver chemicals such as drugs. For example, in vivo micromotors can self-propel in the stomach and intestinal fluids for enhanced retention and targeted delivery in the gastrointestinal tract. Accordingly, the micromotors disclosed herein may provide targeted delivery of chemicals such as drugs.

Recent advances in bio-inspired design principles and nanomaterials have led to tremendous progress in autonomously moving nano/microscale synthetic motors. These tiny motors, designed primarily for biomedical applications, have demonstrated their functionality and versatility in diverse environments. However, there is still a significant gap in moving nano/microscale motors from test tubes to living organisms for treating diseases with high efficacy.

Disclosed are nanoscale and microscale engineered motors and devices, systems and methods for their use and manufacture in gastrointestinal (GI) biomedical applications including diagnosis and treatment of disease and dysfunction. The nanoscale motors may also be referred to as nanomotors, nanoengines, and/or nanomachines, and similarly the microscale motors may also be referred to as micromotors, microengines, and micromachines.

The disclosed nanomotors and micromotors can utilize the environmental conditions of the biological environment in which they are deployed to actuate motion or propel the nano/micromotors in a fluid environment. In some embodiments, the nanomotor/micromotor can include one or more mechanisms to achieve a motile thrust by converting a chemical fuel available within the fluid medium, e.g., of the stomach or intestines of the GI tract, to promote propulsion by such chemo-motile mechanism(s), e.g., including bubble propulsion, self-electrophoresis, and/or self-diffusiophoresis. For example, the nanomotor/micromotor can utilize pH conditions, certain chemical constituents present, temperature or other environmental conditions to cause a reaction with a structural feature of the nanomotor/micromotor that actuates its motion. In some embodiments, the engineered nanomotors/micromotors include a material loaded in its nano/microstructure, capable of reacting with hydronium ions or water, in an acid pH condition or neutral pH condition, respectively, to generate bubbles that accelerate out of the nano/microstructure, propelling the nano/micromotor in the fluid. For example, nanoscale or microscale tubes, wires, spheres, ovals, cones, or other shaped nanostructures or microstructures can be loaded with magnesium nano- or micro-particles that are partially exposed to the outer environment from within the nanostructure/microstructure. The magnesium can react with hydronium ions or water in the deployed environment, yielding magnesium ions and hydrogen gas manifested as bubbles that produce a driving force to the nanostructure/microstructure. In other aspects, the engineered nano/micromotors do not include a fuel and instead are propelled in the fluid due to a pressure gradient produced within a hollowed interior of the nano/microstructure by the ultrasound waves penetrating the concave rear end of the nano/micromotors.

In some embodiments of the disclosed nano/micromotor technology, the nanostructure and/or microstructure can be configured in a tubular shape, e.g., including, but not limited to, a cylindrical or conical geometry, in which, for example, one dimension (e.g., such as the diameter of the tube) is in the nanometer regime and another dimension (e.g., such as the length of the tube) is in the micrometer regime. For example, the nano/microstructures can include one or multiple structural layers, e.g., having an inner layer formed of a first material and an outer layer formed of a second material, or the same material as the first material. In some embodiments, for example, the nano/microstructure can be coated by an outer polymer that can provide various protective functionalities such that the deployed nanomotor/micromotor may be dormant until the outer polymer coating is removed, e.g., via environmental conditions of the biological environment. In some embodiments, the nanomotor/micromotor can be loaded with a payload in the interior region of the nanostructure/microstructure. For example, in some embodiments, the payload can be attached to the first material used in propulsion of the nanomotor/micromotor. In some embodiments, an inner and/or an outer layer of the nanomotor/micromotor can be functionalized to attach other molecules, e.g., such as a fuel substance and/or payload to interact with a target of the biological environment.

Figure 1B:
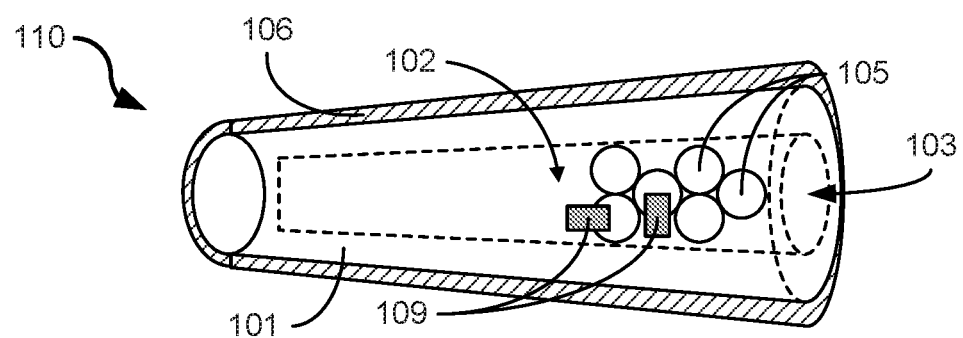
Figure 1C:
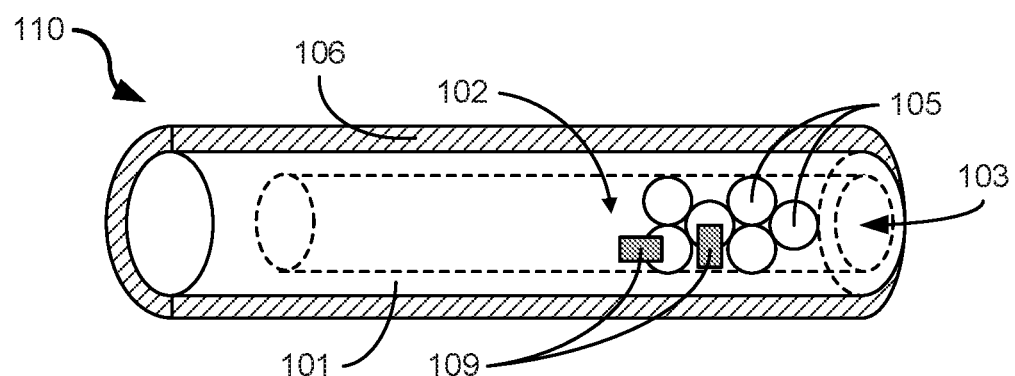
Figure 1D:
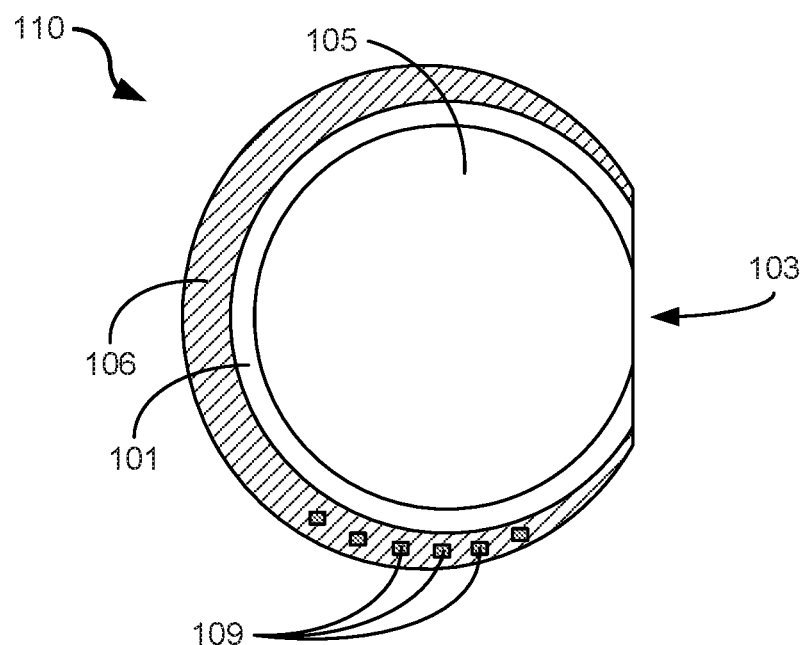

FIGS. 1A-1D show diagrams of an example embodiment of a nano-scale or micro-scale motor 110 for gastrointestinal biomedical applications in accordance with the present technology. The example GI nano-/micro-scale motor 110 is depicted in a rounded or circular shape in FIGS. 1A and 1D, such as a sphere or an oval, but it is understood that other shapes can also be implemented, such as a conical shape or a tubular shape as shown in FIGS. 1B and 1C, respectively. The GI nano/micromotor 110 includes a nano- or micro-scale structure or body 101 that includes an interior region 102 and an opening 103. In some embodiments, the interior region 102 within the nano/microstructure body 101 can have a cross section spatially reducing in size along a longitudinal direction from the opening 103, whereas in other embodiments, the interior region 102 can have a uniform volume with respect to the walls provided by the nano/microstructure body 101. In some embodiments, for example, the nano/microstructure body 101 can be formed of multiple layers, e.g., such as a bi-layer body including an inner layer of a first material and an outer layer formed of a second material; whereas in some embodiments, the nano/microstructure body 101 can include a single layer or material to form the structure. For example, in some embodiments, the multiple layers of the nano/microstructure body 101 can include an embedded layer of a magnetic material that permits external guidance for precision steering of the GI nano/micromotor 110.

In some embodiments, the GI nano/micromotor 110 includes one or more particles 105 to provide a chemo-motile mechanism to drive motion of the nano/micromotor 110 via a reaction with a constituent or based on a condition of the biological environment which the nano/micromotor 110 is deployed. In some embodiments, the one or more particles 105 is a single particle in the interior region 102, like that shown in FIG. 1D; whereas in other embodiments, the one or more particles 105 include a plurality of particles, like that shown in FIG. 1A. In some implementations of the nano/micromotor 110, for example, the one or more particles 105 include a material such as magnesium (Mg) or Zinc (Zn) that, upon contact with GI fluid in the GI tract, a reaction between the Mg (or Zn) of the particle's surface and surrounding hydronium ions, i.e., protons, in the gastric fluid generate hydrogen bubbles at the opening 103, and thereby drive the nano/micromotor 110 in the fluid. Such reaction may also affect acid neutralization of the gastric fluid in the GI tract. In some embodiments, where the nano/microstructure body 101 includes a gold (Au) layer, the motile function of the nano/micromotor 110 can be facilitated based on the presence of the Au layer, which can increase proton depletion through macrogalvanic corrosion. In some embodiments, the nano/microstructure body 101 includes a titanium oxide ($TiO_2$) layer.

In some embodiments, the GI nano/micromotor 110 includes an outer coating 106 to surround the surface of the nano/microstructure body 101. In some embodiments, the outer coating 106 can include a single coating attached to the body 101 while leaving the opening 103 uncovered. Whereas in some embodiments, the example single outer coating 106 can at least partially or completely cover the opening 103. For example, in some implementations, the outer coating 106 provides a protective coating to shield the nano/micromotor 110 from certain conditions (e.g., low or neutral pH) in certain regions of the GI tract while being configured to dissolve or otherwise be removable in other particular region(s) based on the conditions of that particular region(s). In various embodiments, for example, the outer coating 106 can include an enteric coating to prevent dissolution or disintegration in certain regions of the GI tract or gastric conditions. For example, an enteric coating can include an enteric polymer (e.g., copolymers like methacrylic acid-ethyl acrylate, methyl acrylate-methacrylic acid, methyl methacrylate-methacrylic acid) or other enteric compound. In some examples, the outer coating 106 includes an anionic copolymer (e.g., such as the enteric copolymer:anionic copolymer methacrylic acid and ethyl acrylate, known as EUDRAGIT® L100-55), chitosan, or other polymeric and/or biocompatible materials. The outer coating 106 can respond or dissolve to changes in their surrounding (e.g., pH). In some embodiments, the outer coating 106 can include two or more coating layers. In an example, an underlayer of the outer coating 106 attached to the exterior wall of the nano/microstructure body 101 includes the anionic copolymer, and the overlayer of the outer coating 106 includes chitosan; or vice versa.

In some embodiments, the GI nano/micromotor 110 includes a payload 109 loaded in or on the nano/micromotor 110, which can be released at a desired location and/or time in the GI tract. In the example shown in FIG. 1A, the payload 109 is attached to the particles 105, loaded in the interior region 102 of the nano/micromotor 110. In some embodiments, the payload 109 can be attached to the interior wall of the nano/microstructure body 101 in the interior region 102. In some embodiments, the payload 109 can be attached to the outer coating 106 and/or underneath the outer coating 106 attached to the exterior wall of the nano/microstructure body 106. In some embodiments, as shown in the example in FIG. 1D, the payload 109 can be embedded within the outer coating 106.

In some embodiments, the GI nano/micromotor 110 can further include an external coating (not shown in FIGS. 1A-1D) that fully or at least partially covers the GI nano/micromotor 110. For example, the external coating or cover material can include a biocompatible material, e.g., such as chitosan, to protect the nano/micromotor 110 and/or provide adhesive properties of the GI nano/micromotor 110 to particular tissue or regions of the GI system. For example, a positively-charged chitosan outer coating can enable adhesion of the nano/micromotor 110 on the stomach wall.

In some example embodiments of the nano/micromotor 110, for example, the nano/microstructure body 101 can include multiple layers, e.g., having an inner layer including gold and an outer layer formed of a second material, e.g., such as a polymer material, like Poly(3,4-ethylenedioxythiophene) (also known as PEDOT), or a second metal material, such as platinum. In such embodiments, the one or more particles 105 (e.g., a magnesium and/or zinc particle or particles) can be loaded in the interior region 102 of the example gold-PEDOT structure body 101. In such embodiments, for example, the outer coating 106 can include an enteric polymer, such as anionic copolymer methacrylic acid-ethyl acrylate.

In some example embodiments of the nano/micromotor 110, for example, the nano/microstructure body 101 can include a layer of gold, the one or more particles 105 can include magnesium or zinc; and the outer coating 106 can include the payload material 109 (e.g., such as a drug) embedded within the coating 106, such as an enteric polymer that encapsulates the payload.

In some example embodiments of the nano/micromotor 110, for example, the nano/microstructure body 101 can include an inner layer including titanium oxide (TiO$_2$) coated around the one or more particles 105 (e.g., a magnesium or zinc particle or particles) and an outer layer including a payload-loaded polymer layer (e.g., a copolymer), in which the outer layer embeds the payload 109. In such embodiments, the nano/micromotor 110 can include an additional outer or external coating, such as the outer coating 106 (e.g., chitosan or other biocompatible material), that coats the payload-loaded outer layer. These example embodiments are described in further detail in the patent disclosure.

Figure 1E:
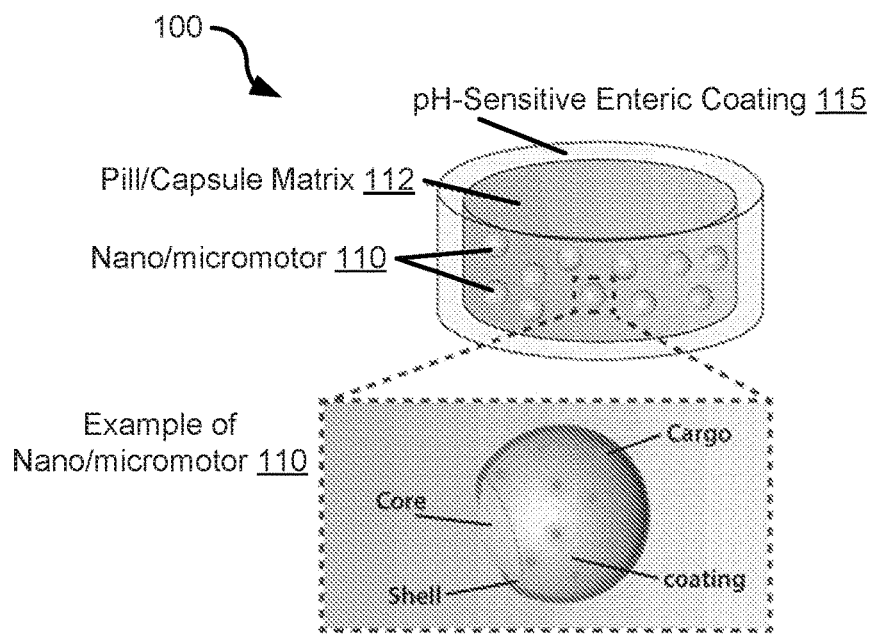
FIGS. 1E and 1F show diagrams of an example embodiment of a gastrointestinal nano/micromotor delivery system in accordance with the present technology.

FIG. 1E shows a diagram of an example embodiment of a gastrointestinal nano/micromotor delivery system 100 in accordance with the present technology that includes a pill or capsule matrix to embed the nano/micromotors 110 for controlled delivery in the GI tract. The GI nano/micromotor delivery system 100 can be embodied as a pill or capsule, which includes a pill/capsule matrix 112 that embeds the GI nano/micromotors 110 within. The GI nano/micromotor delivery system 100 can include a pH-sensitive enteric coating 115, e.g., such as an enteric polymer, to shield the system 100 from certain conditions in the GI tract (e.g., shield in the stomach in the presence of an acidic gastric fluid environment), while being capable of dissolving in other conditions and/or locations of the GI tract (e.g., dissolve the coating 115 in intestinal fluid at more neutral pH).

Figure 1F:
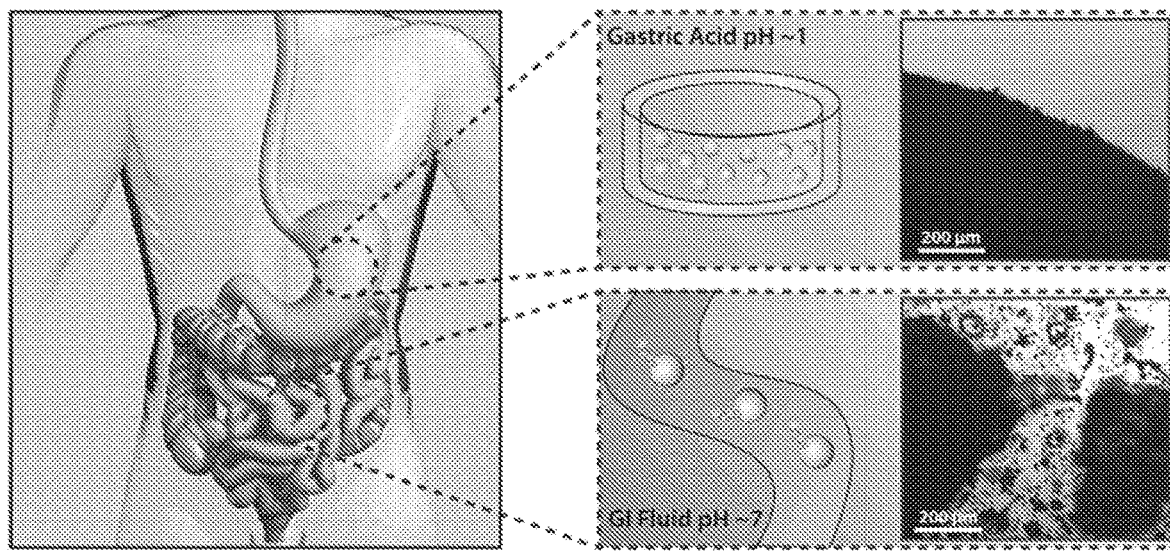

FIG. 1F shows an illustrative diagram depicting an example implementation of the GI nano/micromotor delivery system 100 for controlled functionality, such as controlled location of movement and/or deployment of the payload. The diagram illustrates the pH-sensitive enteric coating 115 shielding the system 100 from the gastric acid (e.g., pH~1) in the stomach, and dissolving in intestinal fluid (e.g., pH~7) in the small intestine to allow the release and motility of the nano/micromotors 110 embedded in the pill/capsule 112, e.g., to perform the desired function of the system 100, such as deliver a payload.

Figure 1G:
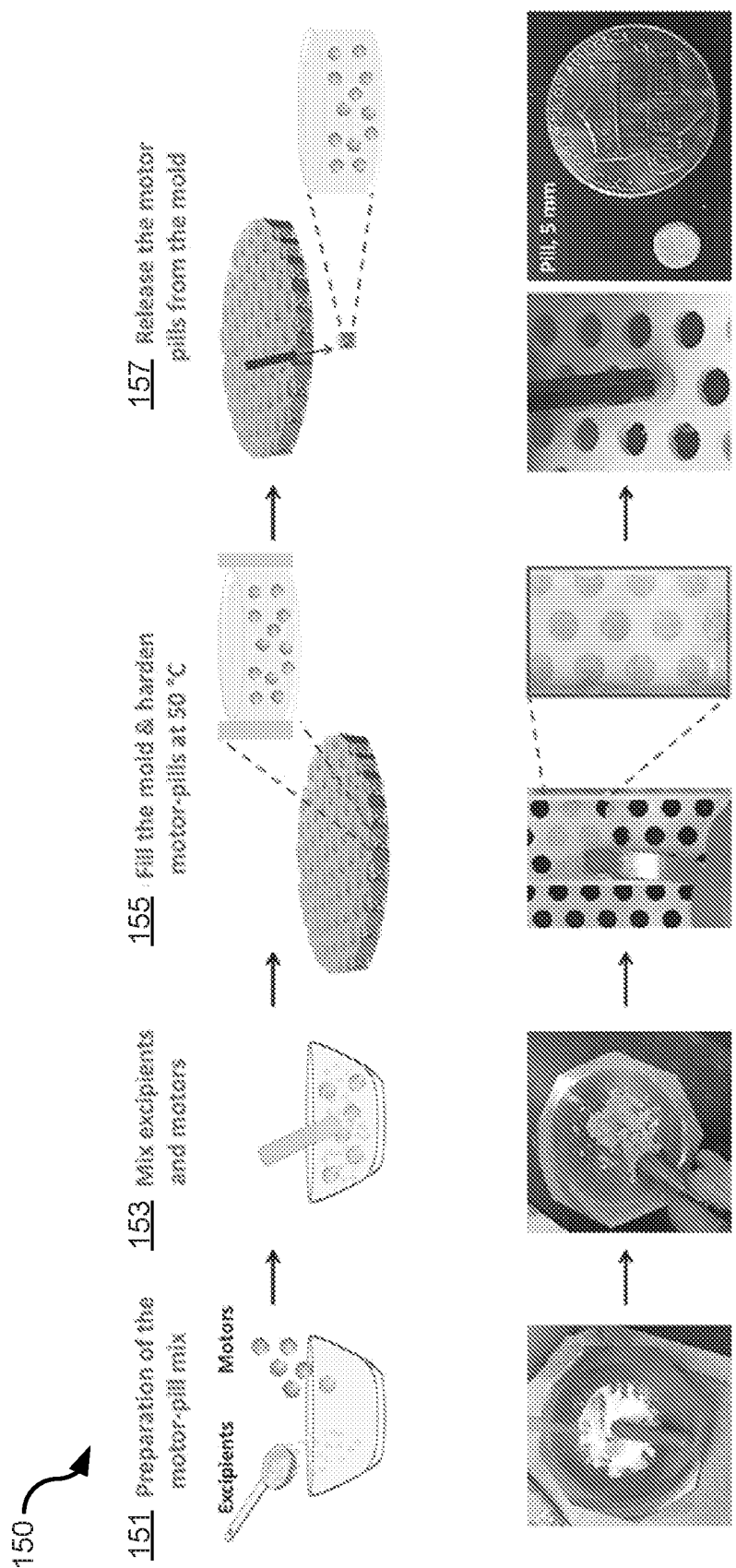
FIGS. 1G and 1H show diagrams of example embodiments to fabricate an example GI nano/motor delivery system in a pill or capsule in accordance with the present technology.

FIG. 1G shows a diagram of an example embodiment of a method 150 for manufacturing a pill-based GI nano/motor delivery system 100 in accordance with the present technology. The method 150 includes a process 151 to prepare add constituents to form a pill matrix (e.g., excipients) and the nano/micromotors 110 in a container. The method 150 includes a process 153 to mix the pill matrix constituents and the nano/micromotors 110 in the container. The method 150 includes a process 155 to form a mold of a pill with the mixed pill matrix constituents and nano/micromotors 110, and to solidify (e.g., harden) the pill structure in the mold. For example, in some implementations, the process 155 includes applying heat (e.g., 50° C.) to harden the pill structures. The method 150 includes a process 157 to release the pill structures from the mold and produce the pill-based GI nano/micromotor delivery system 100. In some implementations of the method 150, the method 150 includes a process to coat the released pill structures with the pH-sensitive enteric coating 115 to produce the pill-based GI nano/micromotor delivery system 100. For each example process of the method 150 illustrated in the upper panel of FIG. 1G, an image is shown (lower panel) depicting an example implementation to produce the pill-based GI nano/micromotor delivery system 100.

Figure 1H:
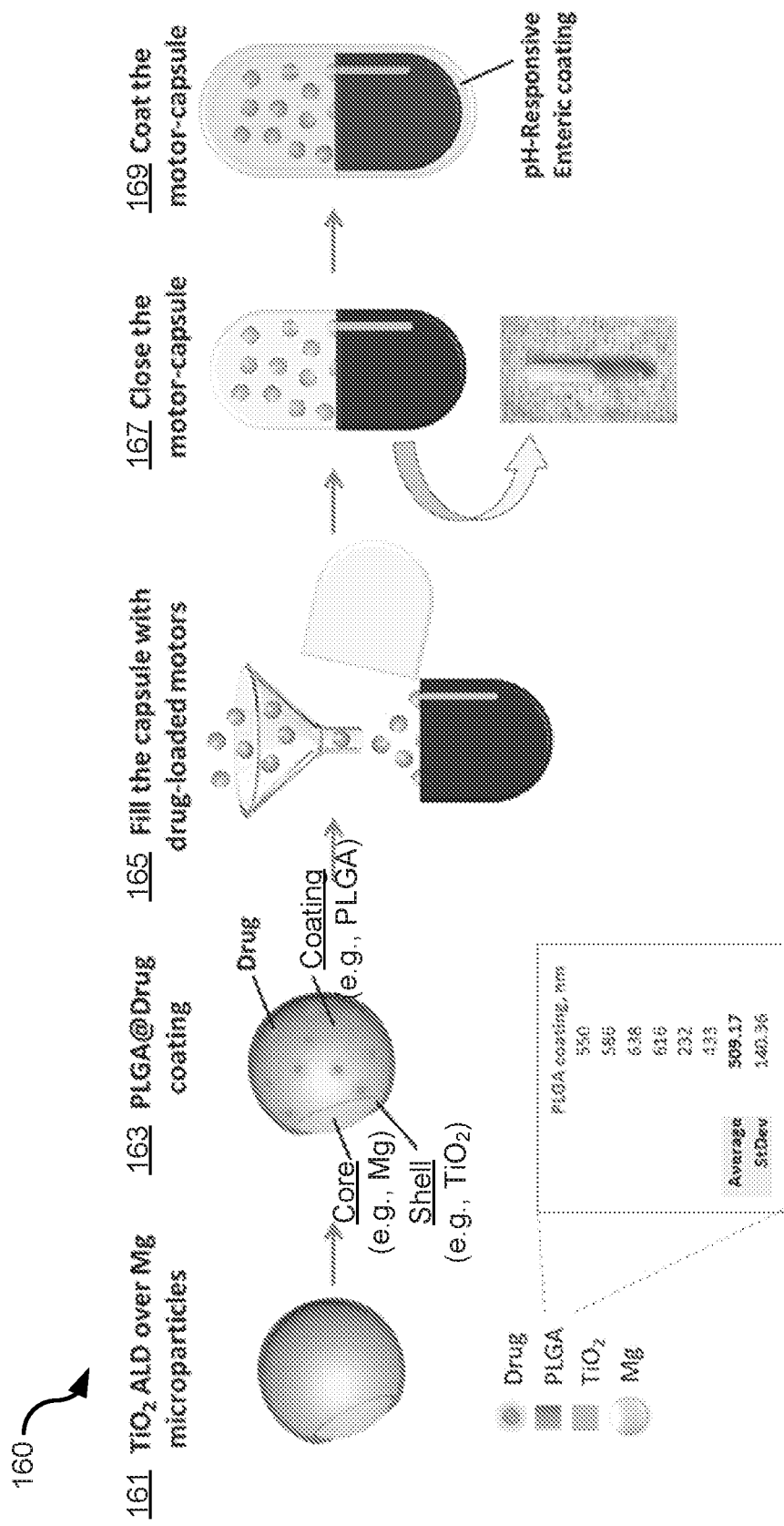

FIG. 1H shows a diagram of an example embodiment of a method 160 for manufacturing a capsule-based GI nano/motor delivery system 100 in accordance with the present technology. The method 160 includes a process 161 to fabricate an intermediate nano/micromotor structure, e.g., the motor 110 without the payload and/or outer coating(s). In the example shown in FIG. 1H, the process 161 includes a process to produce core-shell particle, including a magnesium core particle surrounded by a titanium oxide shell layer. Examples of the process 161 are further discussed in the patent disclosure. The method 160 includes a process 163 to provide a payload-loaded coating on the intermediate nano/micromotor structure (e.g., Mg—TiO$_2$ core-shell particle) to form the nano/micromotors 110. In the example shown in FIG. 1H, the payload-loaded coating includes a drug embedded in a polymer coating including poly(lactic-co-glycolic acid) (PLGA), e.g., having a coating thickness in a range of 370 nm to 650 nm. The method 160 includes a process 165 to fill a capsule structure with the nano/micromotors 110 produced by the process 161-163. Similarly, for example, the process 165 can fill the capsule structure using the nano/micromotors 110 fabricated using another method or technique. The method 160 includes a process 167 to close the capsule structure and form capsule-based GI nano/micromotor delivery system 100. In some implementations of the method 160, the method 160 includes a process 169 to coat the closed capsule structures with the pH-sensitive enteric coating 115 to produce the capsule-based GI nano/micromotor delivery system 100. For each example process of the method 160 illustrated in the upper panel of FIG. 1H, an image is shown (lower panel) depicting an example implementation to produce the capsule-based GI nano/micromotor delivery system 100.

Example Implementations Using Enteric Micromotors for Selective Positioning and Spontaneous Propulsion in the Gastrointestinal Tract The gastrointestinal (GI) tract, which hosts hundreds of bacteria species, is organ system of interest for microbiome research and development of biomedical technologies. Some of the GI microbes are hostile and cause a variety of diseases. The bacteria colonize in different segments of the GI tract dependent on the local physicochemical and biological factors. Therefore, selectively locating therapeutic or imaging agents to specific GI segments is of significant importance for studying the gut microbiome and treating various GI-related diseases. As discussed below, the disclosed technology provides an enteric micromotor system capable of precise positioning and controllable retention in desired segments of the GI tract. In some embodiments, the micromotor system includes magnesium-based tubular micromotors coated with an enteric polymer layer, which can act as a robust nanobiotechnology tool for site-specific GI delivery. The example micromotors can deliver payload to particular location via dissolution of their enteric coating to activate their propulsion at the target site towards localized tissue penetration and retention.

Microbiomes play important roles in the health of many animals, including human beings, thus have attracted intense research interest. While most of the GI microbes live in harmony with the host, some are hostile and cause a variety of diseases. These bacteria colonize in different segments of the GI tract, dependent on local factors. Therefore, selectively locating therapeutic or imaging agents to specific segments of the GI tract is of considerable interest. For example, an ideal GI delivery system should provide a carrier that protects its cargo(s) en-route and/or accurately locate a target or cargo to a desired site of action. Upon arrival at the destination, the carrier should be able to retain there for unloading the cargo(s). Yet, achieving this type of capability is a tremendous challenge, e.g., hampered by the body's natural physiological and structural barriers. As a result, there has been an unmet need to develop a biocompatible nano/micro-scale device that can selectively position in a specific segment of the GI tract and actively penetrate into the tissue for prolonged retention.

Disclosed are artificial micro-scale and nano-scale motors, which are tiny devices that can convert locally supplied fuels or externally provided energy to propelling force and movement of a carrier structure for motile applications. In some examples, micromotors have proved useful for performing diverse biomedical tasks, including transport of cargos, biosensing and imaging, and target isolation. Yet, while the basic research on the synthesis and characterization of artificial micromotors in test-tubes has advanced, there are several challenges that remain for realizing in vivo/in-body applications of such artificial motors.

Example implementations of the disclosed micromotor and/or nanomotor technology are described for an enteric micromotor system including self-propelled micromotors structured to include a magnesium (Mg)-based motor body with an enteric polymer coating for precise positioning and controllable retention in desired segments of the GI tract. While magnesium is described for the example embodiments below, other chemical elements and materials can be used, such as Zinc (Zn), in for the described enteric nanomotors and micromotors and devices, systems and methods thereof. For example, the Mg body allows for spontaneous propulsion in intestinal fluid, while the coating, which is stable in acidic conditions but soluble in neutral or alkaline media, enables accurate positioning of the Mg-based micromotor in the GI tract. The enteric coating can shield the motors from acidic gastric fluid environment (pH 1~3), but dissolves in intestinal fluid (e.g., at pH 6~7) to expose the motors to their fuel and start the movement. By tailoring the thickness of the enteric coating, for example, the micromotors can be tuned to the time required to dissolve the polymer layer, thereby controlling the distance that the motors can travel in the GI tract before their propulsion is activated. Upon activation, the motors will propel and penetrate into the local tissue and retain there to release payloads. The example implementations include evaluation of such micromotors in a mouse model that demonstrates properties and functions of the synthesized enteric magnesium micromotors (EMgMs). The example in vivo results demonstrate that these motors can safely pass through the gastric fluid and accurately activate in the GI tract without causing noticeable acute toxicity.

Figure 2B:
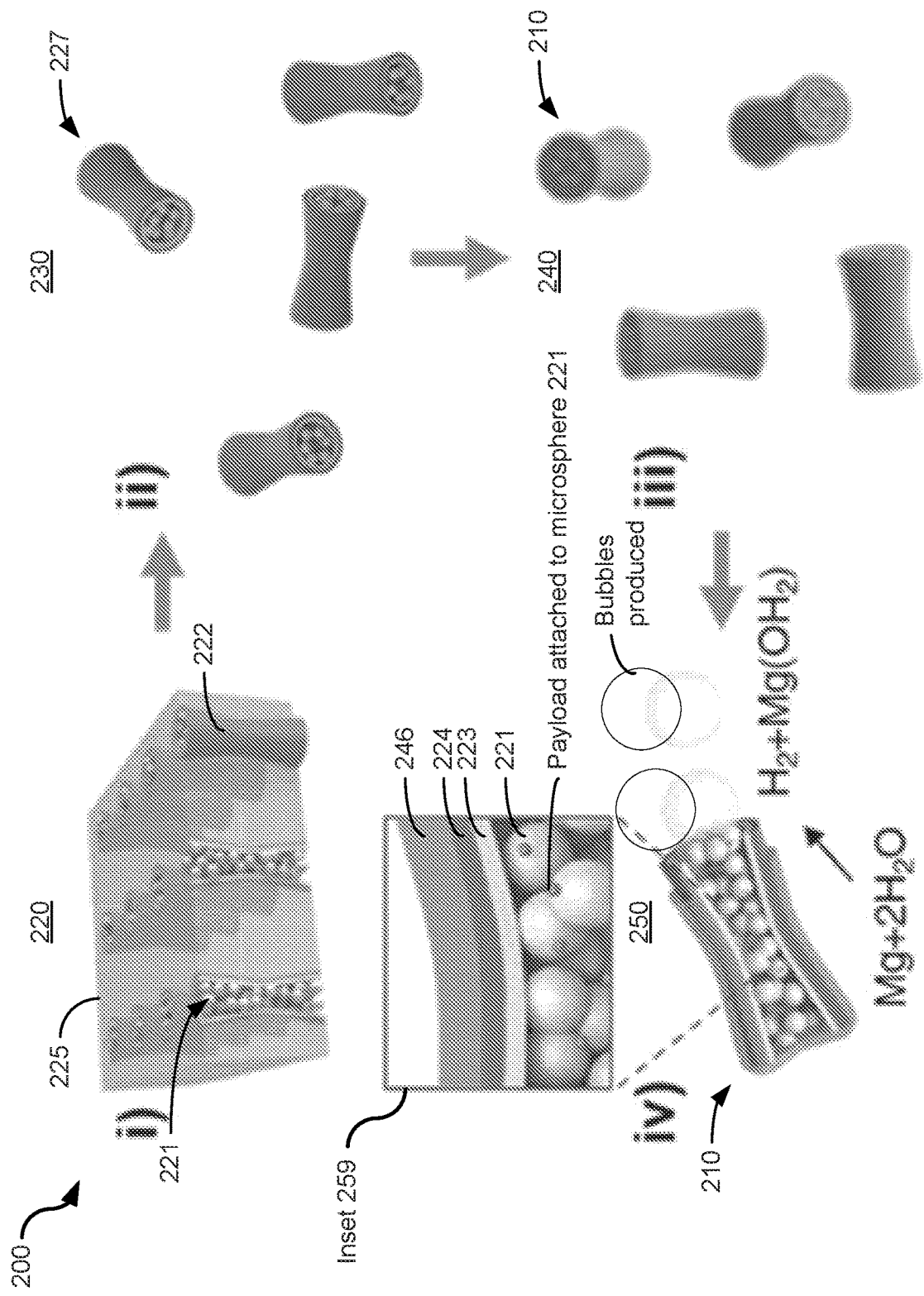

FIGS. 2A-2E show diagrams and images depicting an implementation of an enteric micromotor system capable of precise positioning and controllable retention in desired segments of the GI tract. FIG. 2A shows an illustration depicting the operation principle of example enteric magnesium micromotors (EMgMs) 210 that can selectively position and spontaneously propel in the GI tract by using the pH-sensitive coating which dissolves in intestinal fluid (e.g., pH 6~7). The example EMgMs 210 depict an example embodiment of the GI nano/micromotor 110.

FIG. 2B shows an illustrative diagram depicting an example fabrication method 200 to produce the example EMgMs 210, in which an integrative template-electrodeposition method is utilized with a particle-infiltration technique, e.g., by packing Mg microparticles within template-synthesized PEDOT/Au microtubes with a uniform diameter of 5 μm. The method 200 includes a process 220 to load microspheres, which can attach a payload, into a template that houses microtube structures to produce microsphere/payload-loaded micromotors (labeled 227). For example, as shown in FIG. 2B scheme (i), example Mg microspheres (labeled 221) and payloads are loaded into example PEDOT/Au microtubes (labeled 222), which can be electrodeposited in microporous polycarbonate (PC) membrane (labeled 225), e.g., with pore size of 5 μm and pore length of 15 μm. The layers and payload-attached microspheres contained inside the example PEDOT/Au microtubes 222 are shown in inset 259 of scheme (iv) of FIG. 2B. The method 200 includes a process 230 to dissolve the template and release the loaded micromotors, e.g., which can be collected for the desired application. As shown in FIG. 2B scheme (ii), the PC membrane 225 are dissolved and release the example microsphere/payload-loaded micromotors 227. The method 200 includes a process 240 to coat the loaded micromotors with a polymer coating to produce enteric micromotors (labeled 210). As shown in FIG. 2B scheme (iii), the Mg microsphere-loaded micromotors are coated with an enteric polymer (labeled 246, as shown in inset 259 in scheme (iv) of FIG. 2B). The method 200 includes a process 250 to implement the enteric micromotors for the desired applications. As shown in FIG. 2B scheme (iv), the process 250 can include dissolution of the enteric coating 246 and propulsion of the enteric micromotors 210 in solution with neutral pH. The example template-synthesized PEDOT/Au microtubes serve can provide robust microcontainers for loading the Mg microparticles while Au is used as a model cargo for the example in vivo biodistribution implementations. It is noted that Mg is a biocompatible trace element vital for many bodily functions and that the reaction of Mg microparticles with water can be used to generate propulsion.

Figure 2C:
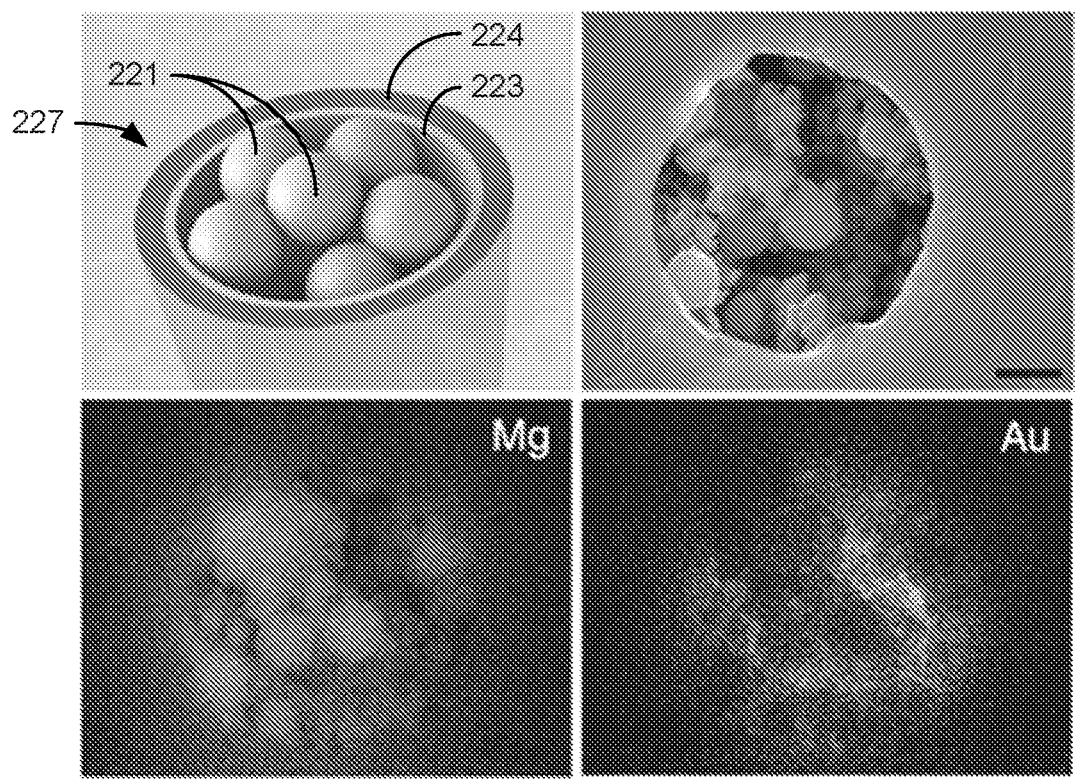
Figure 2D:
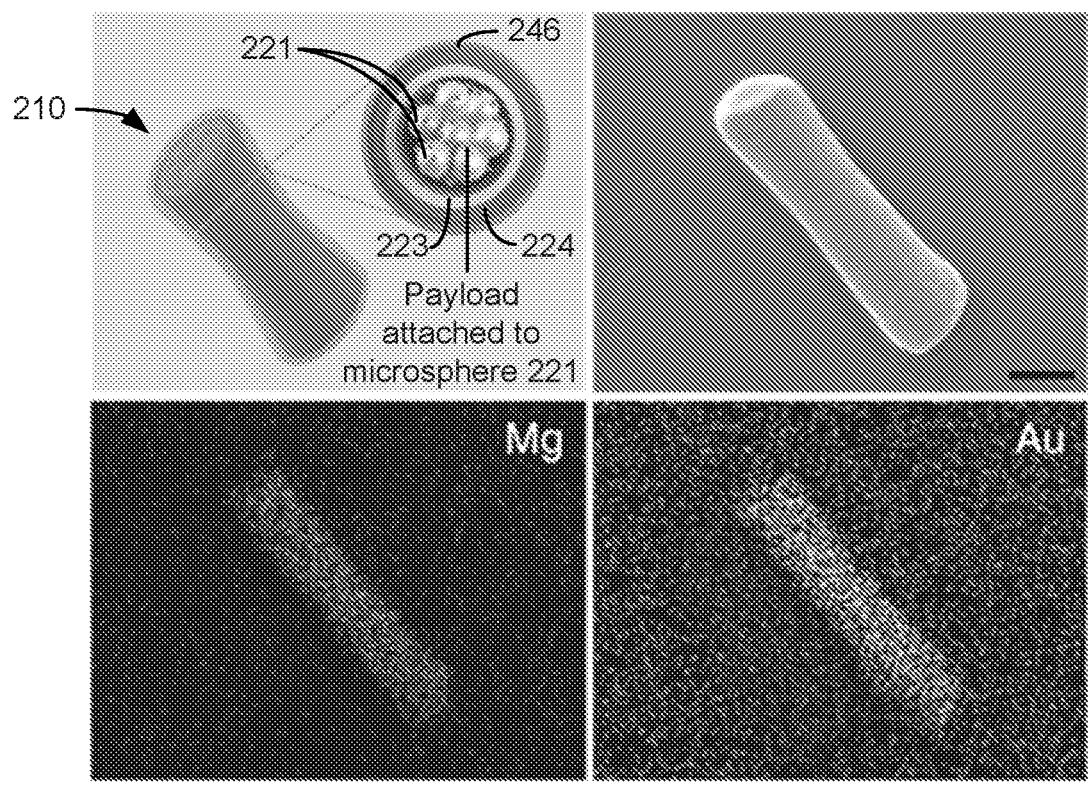

FIG. 2C shows images of a top view of the Mg particles infiltrated into an example PEDOT/Au microtube (e.g., scale bar 1 μm). The SEM images and EDX mapping show that the microtube can be successfully loaded with Mg particles, while the interparticle space could be potentially filled with therapeutic or imaging payloads. The example motors are subsequently coated with methacrylate-based polymer Eudragit L100-55, which has been used for protecting oral drug capsules from the acidic gastric fluid. FIG. 2D shows images of a side view of an example EMgM with SEM characterization and EDX images of the Mg and Au in the micromotor (e.g., scale bar 5 μm). The SEM image and EDX mapping in FIG. 2D depict the micromotor with a smooth enteric polymer coverage. Upon fabrication of the EMgMs, their propulsion performance was evaluated in intestinal fluid. FIG. 2E shows images snapshots during propulsion of a single (i) and multiple (ii) EMgMs in the intestinal fluid (e.g., scale bars 20 μm). The microscopy images of FIG. 2E demonstrate effective movement of a single and multiple EMgMs in intestinal fluid simulant. Hydrogen bubbles propel the motors for approximately 1 min with average speed of 60 μm/s, demonstrating water-powered microtubular motors that can efficiently propel and function in intestinal fluid.

Example implementations of the method 200 for fabricating the enteric magnesium micromotors (EMgMs) shown in FIG. 2B can include the following. In some implementations of the method, polycarbonate (PC) membrane templates, e.g., with pore sizes of 5 μm, can be used for fabricating the Mg-based micromotors. A gold film (e.g., 75 nm) can be sputtered on one side of the porous membrane to serve as a working electrode, e.g., using the Denton Discovery 18 (Moorestown, NJ, USA). A Pt wire and an Ag/AgCl (with 1 M KCl) can be used as counter and reference electrodes, respectively. In the example implementations, the membrane was then assembled in a plating cell with aluminum foil serving as a contact. The electrochemical deposition steps were carried out at room temperature (e.g., 22° C.). First, the outer PEDOT layer of the microtubes was prepared by electropolymerization at +0.80 V using a charge of 0.2 C from a plating solution containing 15 mM EDOT, 7.5 mM $KNO_3$, and 100 mM sodium dodecyl sulfate (SDS); subsequently, a gold layer was deposited at −0.9 V from a gold plating solution (e.g., Orotemp 24 RTU RACK; Technic Inc., USA) with a total charge of 0.6 C. After electrochemical deposition, the sputtered gold layer was completely removed by mechanical polishing with 3 μm alumina slurry. For example, to get the Mg microparticles with favorable size to be loaded in the prepared PEDOT/Au microtube with a diameter of ~5 μm, the microparticles were collected from the commercial ones (e.g., size 0.2-50 μm catalog #FMW20, TangShanWeiHao Magnesium Powder Co., China). Vacuum infiltration process by a 5 μm Polycarbonate membrane (e.g., 110607, Whatman, NJ, USA) was used to remove the Mg microparticles with size larger than 5 μm, then another vacuum infiltration process using a 1 μm Polycarbonate membrane (e.g., 110607, Whatman, NJ, USA) was used to remove the Mg microparticles with size smaller than 1 μm. The obtained Mg microparticles with size of 1-5 μm were then dispersed in isopropanol with a concentration of 10 mg/mL. Thereafter, the Mg microparticle suspension was pumped into the polished polycarbonate templates with electrodeposited PEDOT/Au microtubes using vacuum infiltration. For example, a polycarbonate membrane with a pore size of 15 nm was placed below the 5 μm diameter PC membrane to retain the magnesium microparticles within the upper PEDOT/Au microtubes. The vacuum infiltration process was performed for 2 hours to ensure full loading of Mg microparticles in the microtubes, for example. The polycarbonate membrane was then dissolved in methylene chloride for 2 h to completely release the micromotors, e.g., the Mg microparticles loaded PEDOT/Au microtubes. The micromotors were then collected by a sediment process and washed with methylene chloride and isopropanol (3 times each one), for example. For the example implementations, fluorescent Mg-based micromotors were prepared by using the Mg microparticle suspension dissolved with a Rhodamine 6G dye (83697, SIGMA, USA) with a concentration of 2 μg/mL.

An example enteric polymer (e.g., Eudragit L100-55; Evonik Industries, Germany) was chosen to be coated on the Mg-based micromotors to prevent the Mg microparticles from reacting in stomach fluid thus ensuring their safe reaching to the GI tract. First, a batch of Mg-based micromotors (dissolved from one whole piece of PC membrane) was collected in 0.1 mL isopropanol solution. The example enteric polymer was dissolved into isopropanol solution with three different concentrations of 6.5%, 10.0% and 12.5% (w/v) to prepare the EMgMs with different coating thicknesses. The micromotor suspension was then mixed with the enteric polymer solution with the above three different concentrations, and then dispersed in to a paraffin matrix for a solvent evaporation process. The obtained structures were then solidified with hexanes and a following freeze drying process. A soft annealing process (e.g., 130° C. for 10 min) was implemented to ensure the complete sealing of the Mg-based micromotors, for example. The original diameter of the micromotors without polymer coating is 5 μm, as defined by the micropores of the polycarbonate membrane template. The enteric coating thicknesses were examined by SEM. For the three enteric polymer concentration of 6.5%, 10.0% and 12.5% (w/v), a coating thickness of 0.3, 0.8 and 1.2 μm was calculated by polymer-coated micromotors with an average diameter of 5.6, 6.8 and 7.4 μm, respectively.

For example, to make the silica microspheres-loaded control micromotors, a suspension of silica microspheres (e.g., diameter 1.21 µm, Bangs Lot #8348, Fisher, IN, USA) were added into the PEDOT/Au microtubes, instead of Mg microparticles. An enteric polymer coating, with a thickness of 0.8 am, was then coated on these silica-microspheres loaded micromotors by same method described above using a polymer concentration of 10.0%. The resulting coated silica-microspheres loaded micromotors were then used as control micromotors without movement in the intestinal fluid.

The example implementations of the EMgMs included in vitro and in vivo studies. For example, to evaluate the feasibility of precisely tuning the activation time of EMgMs after entering the GI tract, the example micromotors—with an original diameter of 5 µm—were modified with enteric polymer coatings of three different thicknesses (e.g., 0.3 µm for "thin", 0.8 jam for "medium", and 1.2 µm for "thick") and were tested in vitro in gastric and intestine fluids. The thickness of the polymeric coating was adjusted by using three enteric polymer concentrations of 6.5%, 10.0% and 12.5% (w/v), which resulted in average EMgMs diameters of 5.6, 6.6 and 7.4 µm, respectively. In vitro release of the EMgMs was performed using gastric fluid simulant and intestinal fluid simulant, respectively. Videos of micromotor propulsion were captured by an inverted optical microscope (e.g., Nikon Instrument Inc. Ti-S/L100), coupled with a 40× microscope objective, a Hamamatsu digital camera C11440 using the NIS-Elements AR 3.2 software. In each test of the example release study, EMgMs were dispersed on a glass slide with PDMS cell to prevent the evaporation of the liquid during the observation. In the implementations, about 400 micromotors were typically in the view under the 4× microscope objective. The CCD camera was set to take a microscopy image every minute. When the micromotor generated bubbles or moved from its original place in the imaging, it was consider as being released. The time-dependent release rate was calculated in each test then averaged as the statistical results (n=6).

Figure 3A:
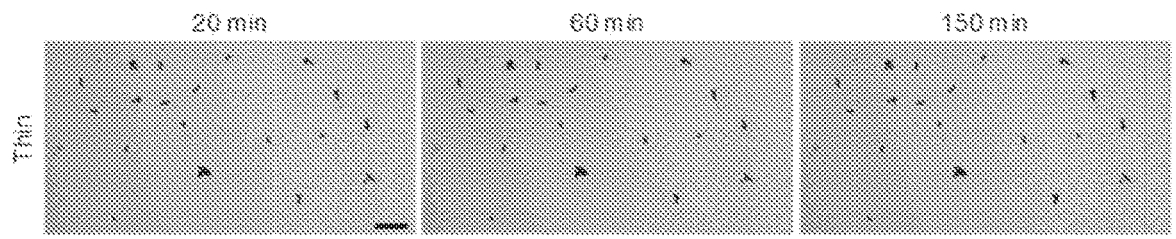
FIGS. 3A-3E show images and data plot of example results from an in vitro evaluation of example enteric micromotors in gastric and intestinal fluids, in accordance with some example embodiments.
Figure 3B:
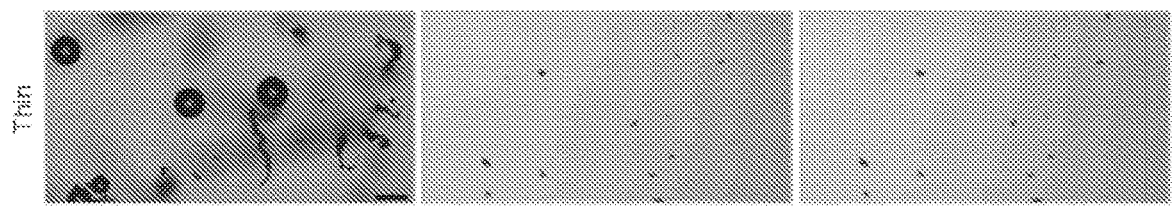
Figure 3C:
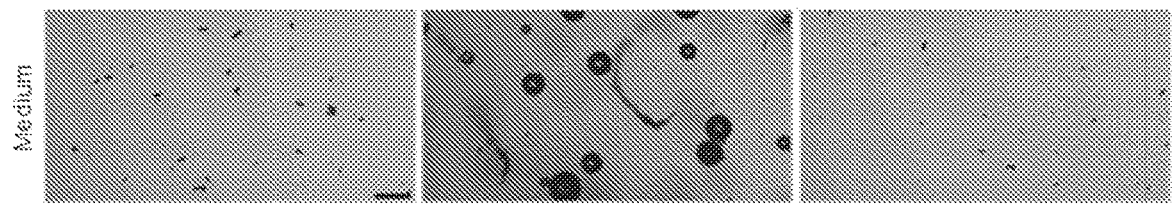
Figure 3D:
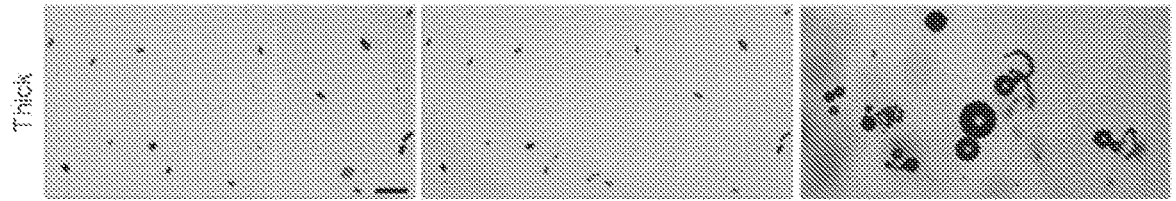
Figure 3E:
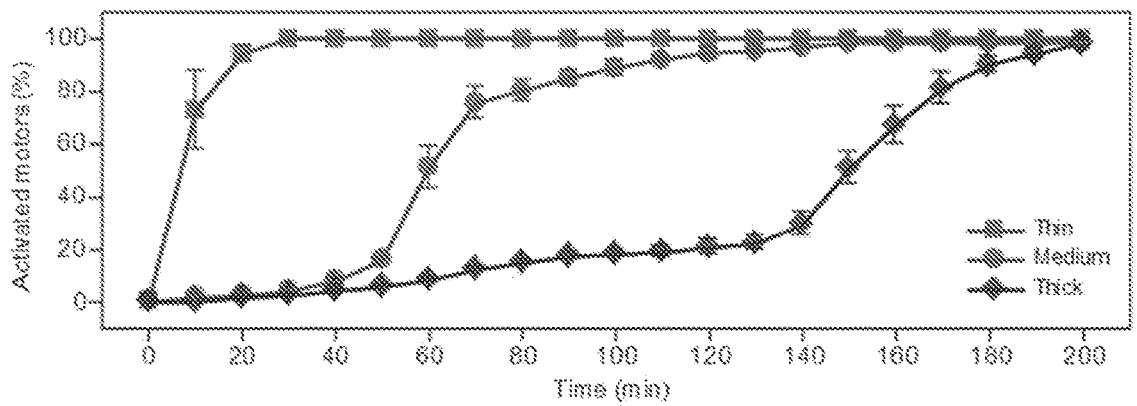

FIGS. 3A-3E show images and data plot of example results from an in vitro evaluation of example EMgMs in gastric and intestinal fluids. FIG. 3A shows microscopy images of example EMgMs with thin thickness of enteric polymer coating immersed in gastric fluid for 20 min, 60 min and 150 min. FIG. 3B shows microscopy images of example EMgMs with a thin enteric polymer coating immersed in intestinal fluid for 20 min, 60 min and 150 min. FIG. 3C shows microscopy images of example EMgMs with a medium enteric polymer coating immersed in intestinal fluid for 20 min, 60 min and 150 min. FIG. 3D shows microscopy images of example EMgMs with thick enteric polymer coating immersed in intestinal fluid for 20 min, 60 min and 150 min. The scale bar of FIGS. 3B-3D is 50 µm. The three coating thicknesses are 0.3, 0.8 and 1.2 µm, respectively. FIG. 3E shows a data plot depicting quantitative analysis of the percentage of activated micromotors in intestinal fluid at different time points (n=6 with 400 micromotors in each test).

As shown in FIG. 3A, the EMgMs with thin coating displayed no bubble generation upon immersing in gastric acid for over 150 minutes, reflecting the shielding ability of the polymer in strongly acidic gastric environment. Upon changing to intestinal fluid, these EMgMs display a burst of bubble generation and efficient propulsion within 20 minutes (FIG. 3B). The efficient propulsion eventually leads to a dynamic distribution of the micromotors to different locations. Medium and thick enteric coatings are able to delay the bubble generation and micromotor propulsion to 60 minutes and 150 minutes after immersion in intestinal fluid, as shown in FIGS. 3C and 3D, respectively.

FIG. 3E shows the quantitative results of the release and activation of EMgMs with different enteric coatings in intestinal fluid. Based upon the statistical analysis of about 400 motors for each group, thin polymer coating results in over 75% of EMgMs activated in intestinal fluid within 10 min, e.g., indicating that the propulsion occurs in the upper segment of the GI tract. In contrast, for example, for a medium-thickness coating, a very slow activation is observed between 30 and 45 minutes, followed by a rapid activation of about 75% of EMgMs between 50 to 70 minutes, e.g., indicating the motors localize at the middle segment of the GI tract. EMgMs coated by a thick polymer layer display very slow activation up to 2 hours, followed by rapid activation of 80% EMgMs at 3 hours, e.g., indicating that these motors can reach the lower segment of the GI tract. These example results verify the possibility of selectively position the motors in different regions of the GI tract by controlling the coating thickness.

The ability of EMgMs to selectively localize at desirable segments of the GI tract was evaluated in vivo using a mouse model. In the example study, four groups (n=3) of mice were assigned to receive EMgMs with three different polymer thicknesses and uncoated micromotors, respectively. Upon oral administration of the motors for 6 hours, the mice were euthanized, and their stomach and entire GI tract were collected to evaluate the biodistribution and retention of the motors. Specifically, the mouse GI tract was sliced into three segments corresponding to duodenum, jejunum and ileum of the GI tract for separate inspection.

Figure 4B:
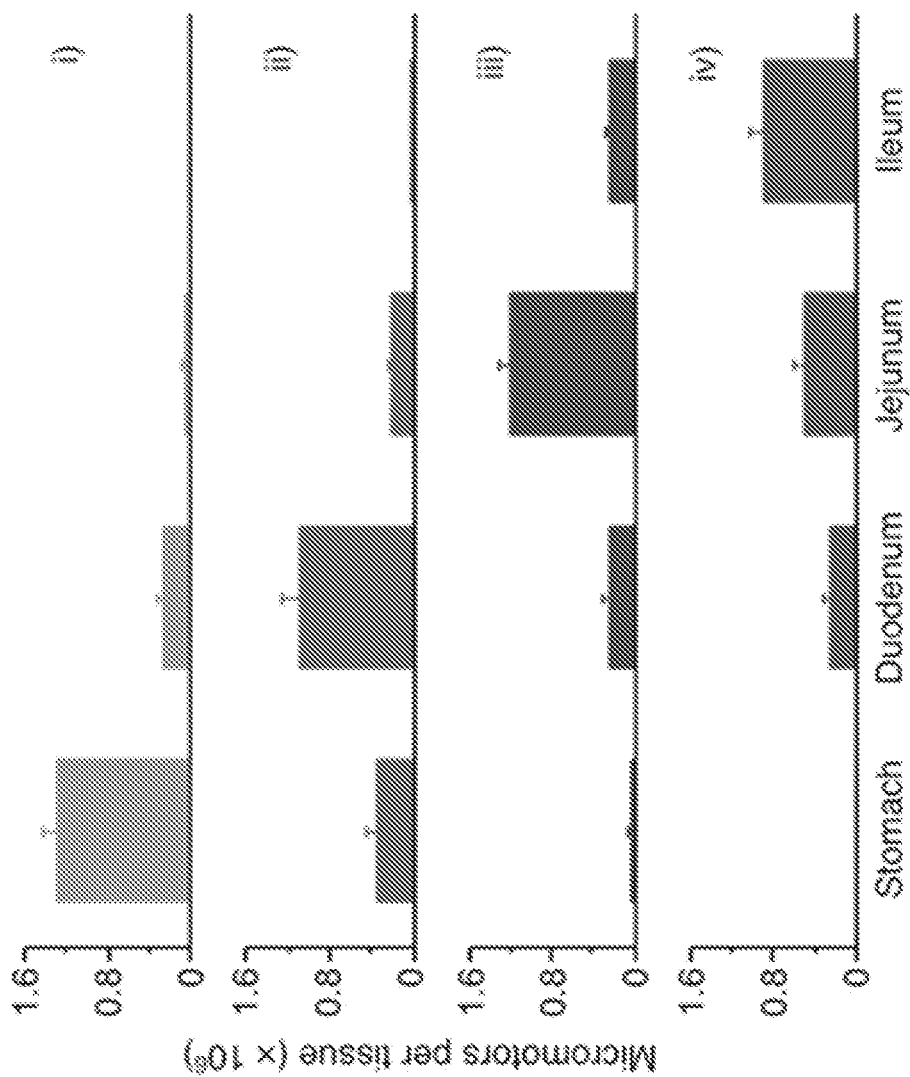
FIGS. 4A-4C show illustrative diagrams, data plots and images of example results associated with in vivo biodistribution and retention evaluation of example enteric micromotors in the gastrointestinal tract, in accordance with some example embodiments.
Figure 4A:
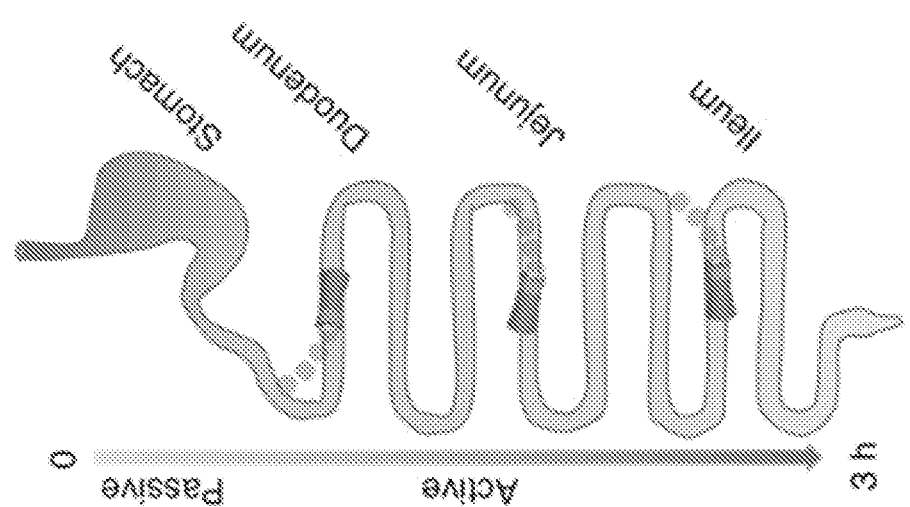
Figure 4C:
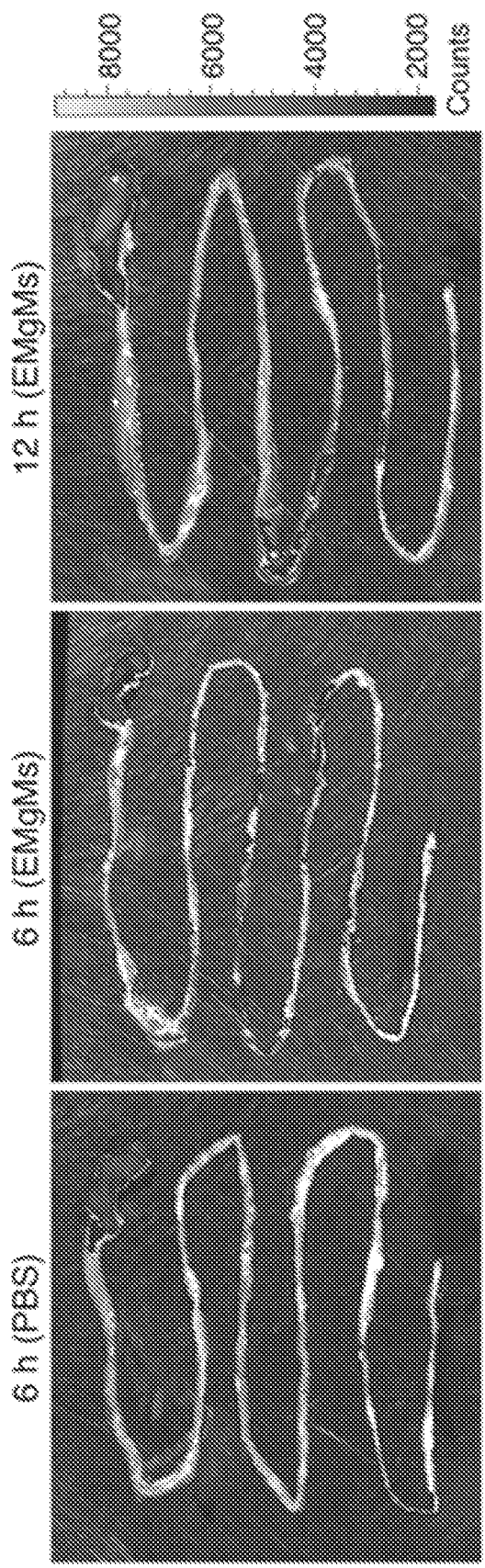

FIGS. 4A-4C show illustrative diagrams, data plots and images of example results associated with in vivo biodistribution and retention evaluation of example EMgMs in the GI tract. FIG. 4A shows an illustrative diagram depicting the localization and retention of the example micromotors in the stomach and GI tract. FIG. 4B shows data plots of the ICP-MS analysis of the number of micromotors with different enteric coating thickness retained in the stomach, duodenum, jejunum, and ileum 6 hours post oral administration. As shown in FIG. 4B, the samples include (i) bare Mg micromotors without enteric coating, (ii) EMgMs with thin polymer coating, (iii) EMgMs with medium polymer coating, and (iv) EMgMs with thick polymer coating (n=6 mice per group). FIG. 4C shows superimposed fluorescent images of mouse GI tracts at 6 hours and 12 hours post-administration of EMgMs loaded with the dye Rhodamine 6G and covered with medium polymer coating. PBS was used as a control.

For the example in vivo GI tract site-specific localization study, 8 weeks old ICR male mice were obtained from Harlan Laboratory (Indianapolis, IN). Mice were gavaged with 0.3 mL of suspension of uncoated Mg-based micromotors or EMgMs with thin, medium, or thick enteric coatings (n=6). GI tracts including stomach, duodenum, jejunum, and ileum from each mouse were collected at 6 hours after administration. The tissues were rinsed with PBS. Each section was placed in a glass vial and 3 mL of aqua regia that included concentrated nitric acid and hydrochloric acid (Sigma-Aldrich, St. Louis, MO, USA) in the ratio of 1:3 was added into the tissue for 12 hours at room temperature. This was followed by annealing at 80° C. for 6 hours in order to remove the acids and then resuspended with 5 mL DI water. Analysis of the amount of micromotors retained in each part of GI tract was carried out by measuring their embedded Au content using inductively coupled plasma-mass spectrometry (ICP-MS). For in vivo retention study, mice (n=6) were fed with alfalfa-free food from LabDiet (St. Louis, MO, USA) for 2 weeks prior to the experiment. A 0.3 mL suspension of fluorescence-labeled EMgMs with medium thickness of enteric coating was administered orally. At 6 and 12 hours after administration, the GI tracts were dissected, rinsed with PBS, and then imaged using an intelligent visual inspection system (IVIS). A 0.3 mL PBS was given to control mice and tissues were collected and imaged at 6 hours after administration. For the example in vivo retention study comparing the propulsive EMgMs with inert silica microspheres loaded micromotors, one group of the mice were orally administered with a 0.3 mL suspension of fluorescence-labeled EMgMs with medium thickness of enteric coating, while another group were orally administered with a 0.3 mL suspension of silica-microsphere loaded PEDOT/Au microtubes coated with medium thickness of enteric coating. At 6 hours after administration, the GI tracts were dissected, rinsed with PBS, and then imaged using an intelligent visual inspection system (IVIS).

FIG. 4B displays the distribution of the micromotors in these three GI segments and the stomach for the four tested groups. The uncoated micromotors display significant (79%) retention in the stomach, reflecting their efficient activation and propulsion in the stomach (FIG. 4B, panel i). The enteric polymer coatings offer robust protection of the micromotors in the stomach and thus enhance their delivery efficiency to the GI tract. A small fraction (16%) of EMgMs with thin enteric coating retained in the stomach (FIG. 4B panel ii) while minimal micromotors were detected in the stomach for EMgMs with medium and thick coatings (FIG. 4B panels iii and iv). In contrast, FIG. 4B panels ii-iv illustrate that 75%, 67% and 54% of the motors retained in the duodenum, jejunum and ileum for EMgMs with thin, medium and thick enteric coatings, respectively. These example results demonstrate that controlling the coating thickness, and hence the exposure and activation times of the motors, has a profound effect upon the biodistribution of EMgMs within the GI tract.

The example implementations further included studying retention of the EMgMs with medium coating in mouse GI tract by orally administrating fluorescently labeled EMgMs. At 6 and 12 hours after EMgMs administration, the entire GI tract was excised for fluorescence imaging, as shown in FIG. 4C. The image obtained from GI tract collected at 6 hours showed the strongest fluorescence in jejunum and the signal remained at the site at 12 hours, which was about four-fold longer than typical gastric emptying times in mouse GI tract. In contrast, when mice were treated with phosphate-buffered saline (PBS) control, there was no detectable fluorescence signal in the GI tissue; some signal observed in the stomach is attributed to the food self-fluorescence. The luminal surfaces of the intestines are covered by a mucus layer, including large and highly glycosylated proteins, which serve as the front line of protection of GI tract. When the cylindrical Mg-loaded motors are locally released and activated in the GI tract, they will propel and collide with the porous, slimy mucus layer and can be readily trapped within the gel-like mucus, leading to an enhanced local retention. To test the hypothesis that the active propulsion of the motors is critical for the enhanced local retention, the retention of EMgMs with medium polymer coating was compared with that of inert silica-microsphere loaded PEDOT/Au microtubes (with the same polymer coating). The latter are inert in the intestinal environment fluid and do not exhibit autonomous propulsion when released. These control micromotors displayed a significantly lower fluorescence intensity, as compared to the EMgMs, reflecting their greatly reduced retention in the jejunum under the same experimental conditions and coatings. Such observations demonstrated that the propulsion of Mg-based micromotors in the acidic stomach environment greatly improved their tissue penetration and retention, e.g., with highly enhanced retention (up to 24 hr) associated with propulsive micromotors. Overall, self-propelled micromotors lead to a dramatically improved localized retention of their payloads in the intestine compared to the passive diffusion and dispersion of inert payloads. The example data verify that both the enteric polymer coating and the propulsion of the Mg-based micromotors are critical for their accurate position and enhanced retention in desired segment of the GI tract.

The toxicity profile of the EMgMs in the GI tract was investigated. For example, to investigate the acute toxicity of EMgMs, 8 weeks old ICR male mice were oral-gavaged with 0.3 mL suspension of EMgMs with medium thickness of enteric coating. Healthy mice treated with PBS were used as a negative control. Mice were sacrificed at 24 hours after the administration. The stomach and small intestine were collected. The stomach was cut open along the greater curvature, and the gastric content was removed. The small intestine was cut to small sections as duodenum, jejunum, and ileum, and rinsed inside with PBS to remove internal residues. The tissues were put in tissue cassettes and fixed with 10% buffered formalin for 15 hours, then moved into 70% ethanol, and then embedded in paraffin. The tissue sections were cut with 5 am thickness and stained with hematoxylin and eosin (H&E) assay. The apoptosis cells were evaluated by terminal deoxynucleotidyl transferase-mediated dUTP nick-end labeling (TUNEL) assay using ApopTag® from EMD Millipore (Billerica, MA, USA). The stained sections were visualized by the Hamamatsu Nano-Zoomer 2.0HT.

FIGS. 5A-5F show images depicting example toxicity evaluations of example enteric micromotors. Specifically, FIGS. 5A-5C show images of the stomach, duodenum, jejunum and ileum of mice treated with PBS buffer, and FIGS. 5D-5F show images of the stomach, duodenum, jejunum and ileum of mice treated with EMgMs with medium polymer coating thickness. At 24 hours post-treatment, the mice were sacrificed and GI tract tissue sections were stained with H&E assay (FIGS. 5A, 5B, 5D, 5E) and TUNEL assay (FIGS. 5C, 5F). The scale bar of FIGS. 5A and 5D is 500 ram; and the scale bar of FIGS. 5B, 5C, 5E and 5F is 100 μm.

Mice were orally administrated with PBS buffer (FIGS. 5A-5C) or suspension of EMgMs with medium polymer coating thickness (FIGS. 5D-5F) and monitored for general toxicity signs every 2 hours for the first 10 hours post administration. No physiological symptoms such as lethargy, rough fur, or diarrhea were observed in both groups. Then, the GI tract was dissected and sectioned for histological evaluation 24 hours after administration. The tissues were first stained with hematoxylin and eosin (H&E) (FIGS. 5A, 5B, 5D, 5E). Apparent alteration of gastric and intestinal mucosal epithelial architectures was not observed or differences in the crypt and villus length and number, or mucosal thickness, between the PBS and motors-treated groups. There was also no infiltration of immune cells such as neutrophils, lymphocytes, or macrophages into the mucosa and submucosa, indicating no sign of tissue inflammation. Furthermore, the deparaffinized mouse gastric tissue sections of motor-treated mice showed no difference in apoptotic gastric and intestinal epithelial compared to the PBS control, as indicated by positive staining cells in TUNEL assay (FIGS. 5C, 5F). Overall, the example in vivo toxicity studies demonstrated no apparent GI mucosal epithelial morphology change or inflammation, suggesting that the EMgMs are biocompatible and safe for oral administration in mouse model.

The example implementations demonstrate a GI delivery system in accordance with the present technology able to delivery and protect cargos en-route and accurately locate them to the site of action. For example, upon arrival at destination, the carrier can retain position at the site for complete unloading of the cargos. These examples of enteric magnesium micromotors provide capabilities for GI diagnoses and treatment applications. For example, by simply tuning the thickness of the pH-sensitive polymer coating, the disclosed enteric micromotors can selectively activate the propulsion of the water-powered micromotors, and thus control their tissue penetration and retention at desired regions of the GI tract. Such combination of accurate positioning and active propulsion demonstrate that a microscale robot can achieve desired biodistribution and enhanced retention simultaneously in the GI tract. Furthermore, the use of advanced pH-sensitive materials for precise local manipulation of microrobot for site-specific active delivery (e.g., as compared to conventional passive-diffusion-driven delivery vehicles) is envisioned to pioneer novel delivery approaches and advance the emerging field of medical nano/micromotors and nanorobotics. While future studies are warranted to validate the delivery efficiency and therapeutic efficacy, the micromotor-based GI transporter system offers innovative combination of accurate positioning and active propulsion towards effective localized GI delivery of cargos and personalized treatment of GI diseases and disorders.

Example Implementations Using Micromotors for Spontaneously Neutralizing Gastric Acid for pH-Responsive Payload Release Consistent with some example embodiments of the enteric micromotor system, a magnesium (Mg)-based micromotor can be covered by a pH sensitive polymer coating, which may temporarily neutralize the acidity of the stomach fluid in vitro and/or in vivo. Acidity of the stomach fluid may be used by the micromotors as fuel. By using acid as fuel, synthetic motors may rapidly deplete protons while propelling in the stomach which can effectively elevate the gastric pH to neutral in less than 20 minutes. The micromotor-induced neutralization of the stomach fluid may trigger a payload release from a pH-sensitive polymer coating. In contrast to acid suppression by proton pump inhibitors (PPIs), the micromotors temporarily alter the local environment without blocking the function of the proton pumps. As such, the disclosed approach minimally interferes with the function of the stomach and may eliminate adverse side effects associated with PPIs. These example micromotors may be made of biocompatible materials without biological activities, so they are safe to use and will not cause acute toxicity. For example, compared to conventional pH-responsive nanocarriers that passively respond to the local environment, the disclosed micromotors can actively adjust their surroundings to reach desired conditions for triggered payload release. The disclosed micromotors, with built-in dual capabilities of acid neutralization and pH-responsive payload release, provide a platform for drug delivery to treat various gastric diseases.

In some example embodiments, a micromotor device for the gastric-intestinal system includes a magnesium microsphere; a metal (e.g., gold) coating affixed to the magnesium microsphere; a polymer layer affixed to the metal coating; and a payload material encapsulated by the polymer layer, in which, when the polymer layer is immersed in a solution at or below a predetermined acidic pH, the magnesium microsphere reacts with the acidic solution thereby (i) generating hydrogen to propel the enteric micromotor, (ii) depleting protons in the solution thereby increasing the pH of the solution, and (iii) releasing the payload material from the polymer layer.

In some example embodiments in accordance with the example micromotor device, the predetermined acidic pH is approximately 1.3. In some example embodiments, the polymer layer includes EUDRAGIT® L100-55. In some example embodiments, the payload material includes one or more of a rhodamine 6G (R6G) dye and a DiD dye.

Figure 6A:
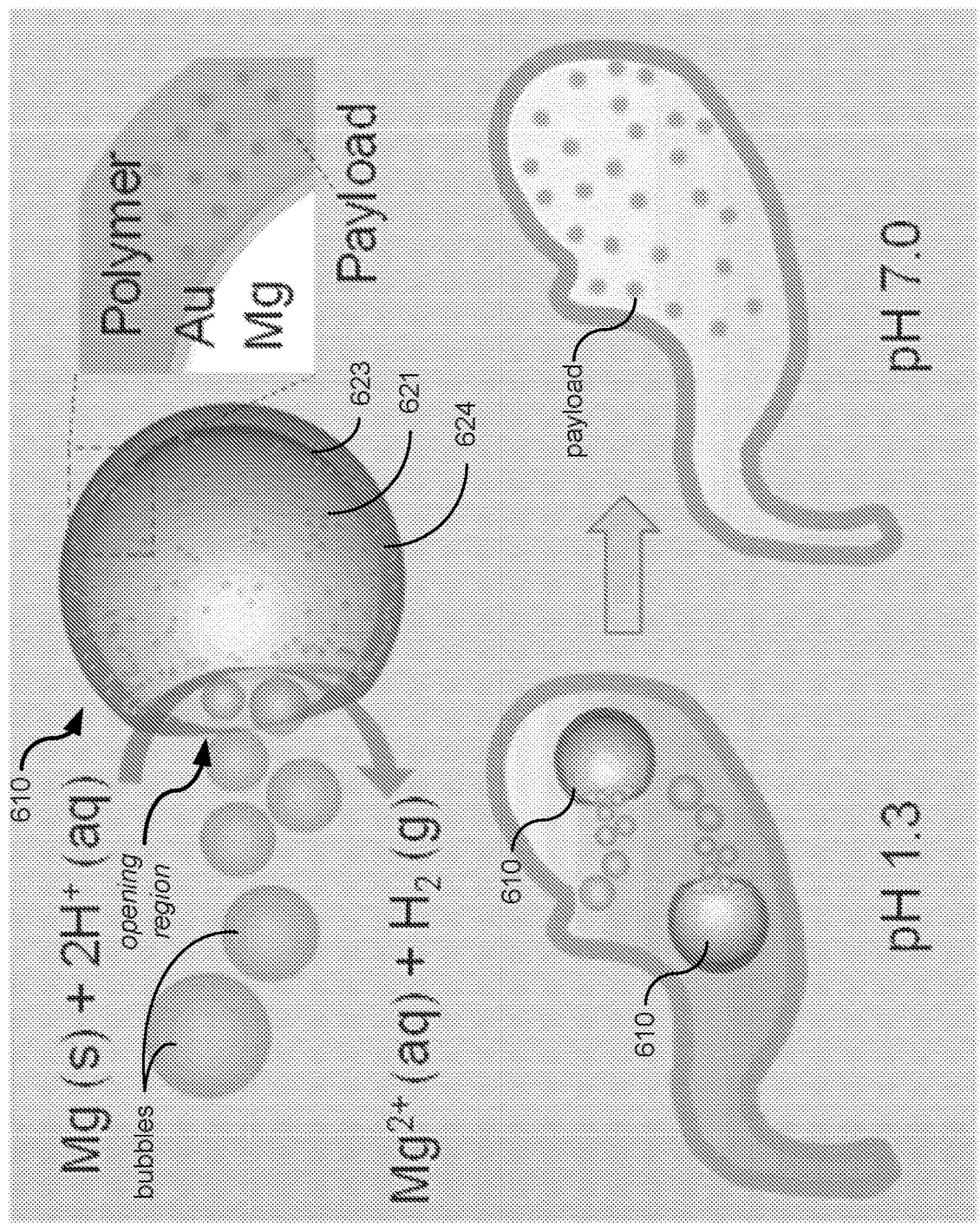
FIGS. 6A-6C show illustrative diagrams and images of enteric micromotors including acid-powered magnesium (Mg)-based micromotor and an associated acid neutralization mechanism, in accordance with some example embodiments.

FIG. 6A shows an illustrative diagram depicting an example enteric micromotor 610 that includes a magnesium (Mg) microsphere 621 coated with an interior layer 623 (e.g., a thin gold (Au) layer) and a polymer layer 624. The example micromotor 610 depicts an example embodiment of the GI nano/micromotor 110. In some implementations, the micromotor 610 includes a payload-encapsulated pH-sensitive polymer layer. The example embodiment shown in FIG. 6A of the enteric micromotor 610 includes an opening in the polymer layer that can expose the Mg surface to the acidic outside environment. For example, at acidic pH, the Mg may react with the acids to generate hydrogen bubbles, propel the micromotors 610, and deplete protons in the solution. This may cause an increase in pH, and the release of a payload from the pH-responsive polymer layer. The example of the enteric, acid-powered micromotor 610 shown in the illustrative diagram of FIG. 6A includes the coated Mg microsphere, the pH-sensitive polymer coating, and an encapsulated cargo.

In various implementations, for example, the enteric, acid-powered micromotors 610 are capable of movement, acid neutralization, and/or cargo transport and release in an acidic environment, such as the stomach or other environments. The Mg-based enteric micromotors 610 can convert the acid fuel to propulsion force and simultaneously alter the local pH that may cause payload release from the pH-sensitive coating. In some embodiments, the enteric micromotor 610 can include a Mg microsphere with a diameter of approximately 20 microns. To fabricate the micromotors, for example, a layer of Mg microparticles may be dispersed onto a glass slide, followed by an asymmetrical coating of the microspheres by sputtering with an approximately 10 nanometers (nm) gold (Au) layer that may cause propulsion via the macrogalvanic corrosion of the Mg surface. After sputtering the Au layer, for example, the microspheres may be coated with a pH-sensitive polymeric film containing the payload. For example, EUDRAGIT® L100-55 which dissolves at pH>5.5 may be used as the polymeric film/coating 624. Other polymeric films/coatings may also be used. The well-separated Mg micromotors may be obtained via soft mechanical scratching of the glass slide, leaving a small opening that exposes the Mg surface to reaction with the gastric fluid that may lead to the hydrogen-bubble generation and propulsion. In some embodiments, the enteric micromotors 610 can include Janus micromotors. The enteric micromotors 610 can be configured to be biocompatible since magnesium is an essential mineral needed for variety of physiological functions, for example. The enteric polymer coating may be used for drug delivery and release, for example. Also, for example, the gold layer can provide a material to the enteric micromotor 610 capable for imaging and/or therapeutic applications. The lower section of FIG. 6A illustrates an example in vivo acid neutralization process associated with the propulsion of the Mg-based Janus micromotors along with the corresponding payload release from the pH-sensitive polymer layer. Upon contact with the gastric fluid, a spontaneous reaction between the Mg microsphere micromotor surface and the surrounding protons (displayed in top portion of FIG. 6A) may generate hydrogen bubbles, and accordingly micromotor thrust. The reaction and acid neutralization may be facilitated by the presence of the Au layer which boosts proton depletion through macrogalvanic corrosion.

Figure 6B:
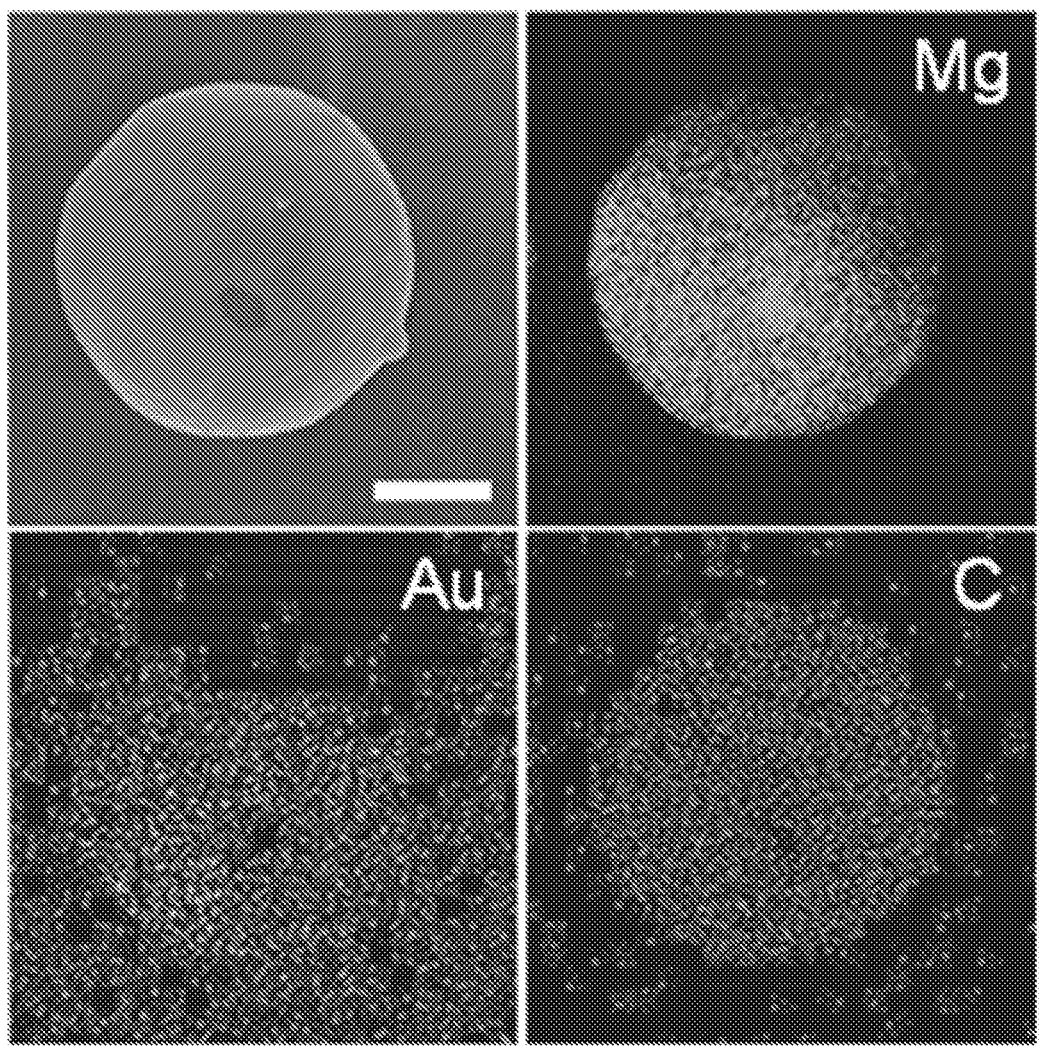

FIG. 6B shows a scanning electron microscopy (SEM) images and energy-dispersive X-ray (EDX) spectroscopy characterizations of an example Mg-based enteric micromotor 610. The scale bar in FIG. 6B corresponds to 5 microns. The example of FIG. 6B demonstrates a characterization of Mg-based Janus micromotors. The SEM image (top left) shows a small opening (e.g., approximately 2 micron) presented on the spherical Mg-based micromotor, that may be produced during the coating process of the micromotors to expose the Mg surface for reaction with the surrounding acidic fluid. The presence of Mg, Au, and carbon (from the polymer coating) was confirmed by the corresponding EDX spectroscopy mapping images (top right, bottom left, and bottom right).

Figure 6C:
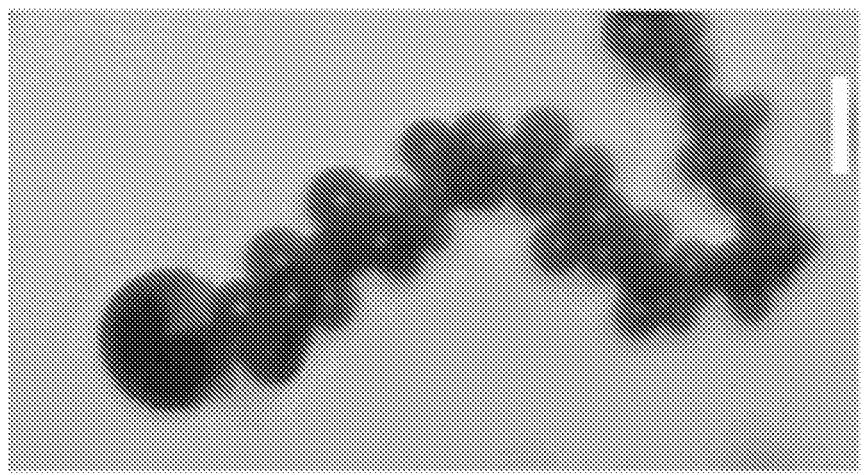

FIG. 6C shows an optical microscopy image illustrating the bubble propulsion of a micromotor in gastric fluid. The scale bar in FIG. 6C corresponds to 20 microns. The image in FIG. 6C depicts the micromotor movement in gastric fluid simulant (pH 1.3). Efficient hydrogen bubble generation may propel the micromotor with an average speed of 60 microns per second, indicating that the micromotors can rapidly react and move in gastric fluid.

FIGS. 7A-7E show data plots and images of example results from implementations using Mg micromotors to neutralize gastric acid and pH-triggered release of a payload, in accordance with some example embodiments. FIG. 7A shows an example of a time-dependent pH neutralization that is associated with the proton consumption during the reaction and propulsion of Mg micromotors in gastric fluid (initial pH 1.3) using 2.75 mg of micromotors and 3 mL of gastric fluid. The Mg micromotors may neutralize gastric acid and trigger release of the payload in vitro. In some example implementations, the pH of the fluid may increase from 1.3 to 6.2 within approximately 12 minutes, followed by stabilizing at an approximate pH 7.5 after approximately 18 min. Accordingly, neutralization of gastric acid can be performed in less than 20 min using the disclosed subject matter. In contrast, PPIs used to reach the same level of neutralization require 1 hour or more. In some implementations, a fluorescent pH indicator such as BCECF may be used to indicate the pH neutralization of the gastric fluid by the micromotors.

FIG. 7B shows a data plot of fluorescence intensity of the pH indicator BCECF in gastric fluid (pH 1.3), gastric fluid containing 2.75 milligrams g of Mg micromotors, and PBS buffer (pH 7.4), respectively. The data plot includes an inset of images illustrating examples of the corresponding solutions. In FIG. 7B, in the absence of Mg micromotors, the gastric fluid containing the BCECF indicator displays a light yellow color and weak fluorescence intensity, indicative of acidic conditions. A color change to red may be observed approximately 20 min after adding the Mg micromotors to the gastric fluid; the fluorescence intensity may increase to a similar level to that observed in a PBS buffer (pH 7.4) as a control solution. Accordingly, BCECF indicates that the Mg micromotors neutralize gastric fluid through fast proton depletion and efficient propulsion. The fast neutralization may result from the fluid convection induced by the collective motion of micromotors in the gastric fluid and the corresponding bubble generation. As such, micromotor-induced "self-stirring" may accelerate environmental decontamination processes.

FIG. 7C shows a data plot of time-dependent fluorescence intensity of released rhodamine 6G (R6G) dye in the supernatant of 3 mL gastric fluid. R6G dye can be loaded in the pH-sensitive polymer coating (starts to dissolve at pH>5.5) as a model payload. Polystyrene (PS)-based inert microparticles with a similar size to the Mg micromotors may be used as a negative control. In the example implementations, R6G dye was used as a payload encapsulated by the pH-sensitive EUDRAGIT® L100-55 polymeric coating of the Mg micromotors to indicate the neutralization of the gastric fluid. In some implementations, inert polystyrene (PS) microspheres (with diameters of approximately 10 microns) coated with the R6G dye-loaded polymer layer may be used as a control group. FIG. 7C depicts an example payload release profile. In the example, the payload release profile results from determining the supernatant fluorescence intensity, using the micromotors and inert (control) particles placed in the acidic gastric fluid (initial pH 1.3). The pH change associated with the presence of the Mg micromotors may result in sustained release of R6G from the pH-sensitive polymeric coating. The fluorescence of the gastric fluid solution may increases gradually and may reach a plateau in approximately 20 minutes. In contrast, R6G release may not be observed using the inert PS microparticles that do not react with the protons to cause a pH change and thus the pH-sensitive polymer coating remains stable.

FIG. 7D shows a fluorescence image showing the propulsion and release of an R6G-loaded Mg micromotor. The scale bar in FIG. 7D corresponds to 20 microns. The fluorescence signals observed on the micromotor body and the yellow bubble tail may indicate the dissolution of the polymer and subsequent release of R6G.

FIG. 7E shows fluorescence images of released R6G in a supernatant of gastric fluid containing Mg micromotors (left), and PS microparticles (right). FIG. 7E shows the corresponding fluorescence photographs of R6G in 1 mL bulk gastric solution in the presence of Mg micromotors and inert control microparticles (both coated with R6G-loaded pH-sensitive polymer), respectively. The images indicate that the dye is released into the solution using micromotors and resides in the sediment at the bottom (containing the inert microparticles). This indicates that the Mg micromotors, which actively neutralize the gastric fluid, can trigger drug release illustrating an advantage of the disclosed micromotor-based delivery over conventional stimuli-responsive drug release. The micromotors themselves may actively create the desired environment (stimuli) to trigger the drug release.

The example Mg micromotors 610 can be used for in vivo applications. Example implementations of the enteric micromotors 610 were used in mice. The disclosed pH neutralization process may be implemented by administrating different amounts of Mg micromotors. For example, example implementations employing the enteric micromotors 610 included administering 0, 2.5 mg, 5 mg and 10 mg of Mg micromotors to four groups of mice (n=3 for each group). Upon oral administration for 20 min, the stomach pH values were determined using a microelectrode sensor coupled with a pH meter to validate the effects on pH by the varying amounts of administered enteric micromotors.

Figure 8A:
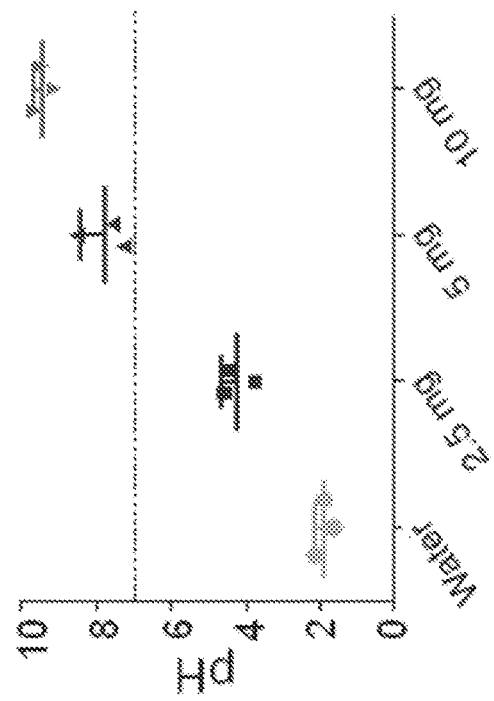
FIGS. 8A-8C show illustrative diagrams, data plots and images of example results associated with in vivo acid neutralization and pH-triggered payload release, in accordance with some example embodiments.
Figure 8B:
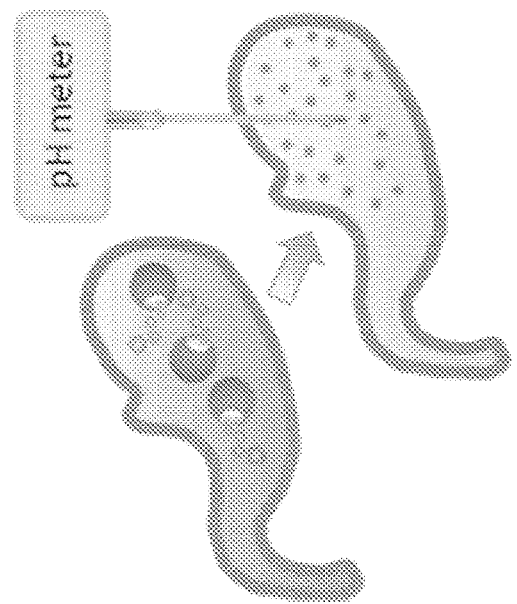
Figure 8C:
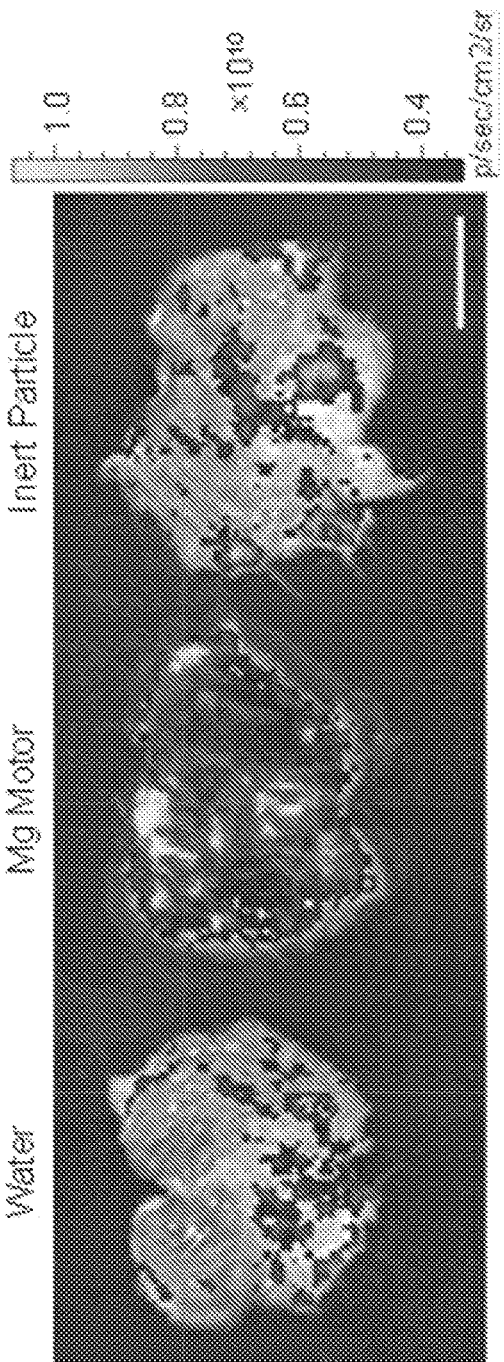

FIGS. 8A-8C show illustrative diagrams, data plots and images of example results associated with in vivo acid neutralization and pH-triggered payload release, in accordance with some example embodiments. FIG. 8A shows an illustrative diagram depicting an in vivo gastric acid neutralization implementation using the example Mg enteric micromotors 610 and pH measurements of the GI organ (e.g., stomach) using a microelectrode-enabled pH meter.

FIG. 8B shows a data plot of in vivo gastric pH values in mice (n=3) measured 20 minutes post administration of different amounts of Mg micromotors with de-ionized water was used as a negative control. In the example of FIG. 8B, gastric pH changes were shown to be dose-dependent. For example, 5 mg of Mg micromotors was able to neutralize gastric acid in the mouse stomach, resulting in pH=7.81±0.38. In the mouse, the micromotor concentration was higher than the 2.75 mg per 3 mL gastric acid that was used in the example in vitro study. An increase in the micromotor amount may be due to continuous secretion of gastric acid from gastric glands in the mouse stomach, as well as the dynamic peristalsis wave of the stomach tissue that counteracts and dilutes the pH neutralization efficacy of the micromotors. Lower and higher doses of Mg micromotors may result in slightly acidic or alkaline stomach environments (e.g., pH 4.24 for 2.5 mg Mg micromotors, and pH 9.43 for 10 mg Mg micromotors, respectively). Using deionized (DI) water as a control resulted in a constant acidic stomach pH (1.88), which indicates that no pH neutralization occurs in the absence of Mg micromotors.

In vivo, pH-responsive payload release may be determined by orally administrating fluorescently labeled Mg micromotors. DiD dye may be used as a model drug, and may be loaded in the pH-sensitive polymer coating. At approximately 20 minutes after administration fluorescence imaging may be performed. FIG. 8C depicts examples of superimposed fluorescent images of the whole stomach of mice collected 20 min post administration of de-ionized water, Mg micromotors, or inert PS microparticles (both Mg micromotors and PS microparticles are loaded with DiD dye which is encapsulated in the pH-sensitive polymer coating as a model drug. DiD dye may also be referred to as DiIC18(5). The scale bar in FIG. 8C corresponds to 5 millimeters (mm). FIG. 8C indicates the stomach from mice treated with 5 mg Mg micromotors displays strong and evenly distributed fluorescence intensity over the entire stomach, reflecting the pH change due to the proton depletion by the active Mg micromotors. The example Mg micromotor delivery system can tune the stomach environment to facilitate dissolution of pH-sensitive polymer and release of the payload. In contrast, mice treated with an equal amount of inert PS microparticles display only small areas of the stomach with low fluorescence signal similar to the fluorescence signal observed using the de-ionized (DI) water control, reflecting the self-fluorescence of the administered food. The inert PS microparticles may not alter the stomach pH, and hence may not trigger dissolution of the pH-sensitive polymer and consequent payload release. FIG. 8C demonstrates Mg micromotors neutralizing gastric acid in the stomach of live animals and triggering the dissolution of the pH-responsive polymer coating with the consequent payload release. The micromotor may serve as a motile carrier that enhances transport of its payload to different locations. The efficient local propulsion, along with the corresponding bubble tail, are shown to generate an effective convective fluid transport to enhance the delivery of cargo compared to passive-diffusion systems. Furthermore, the propulsion of Mg micromotors may penetrate a mucus layer and enhance the payload retention in the stomach and GI tract.

Figure 9A:
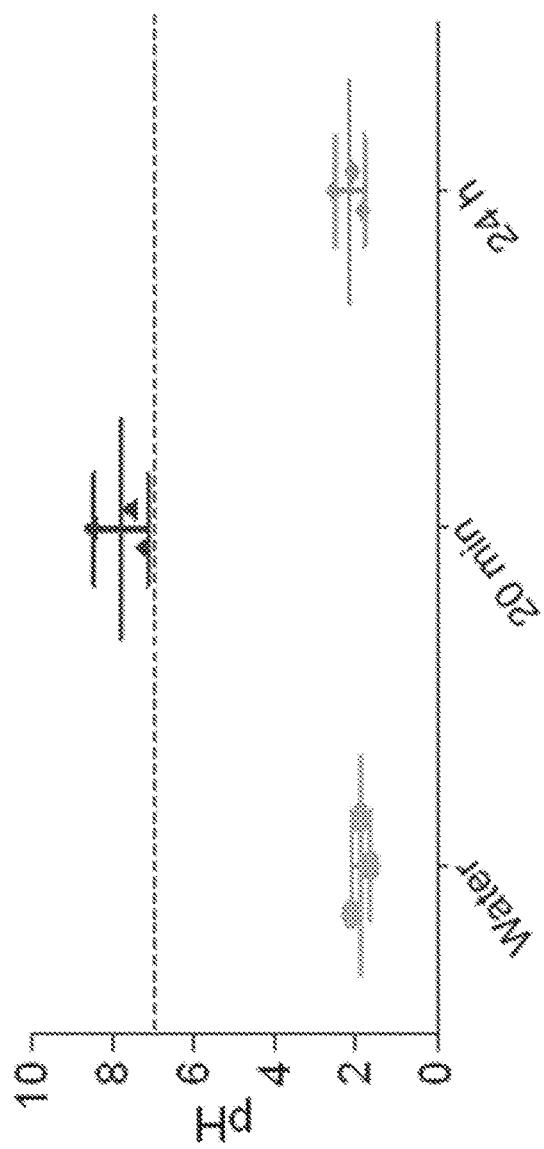
FIGS. 9A and 9B show data plots and images of example results depicting recovery of the gastric pH post micromotor treatment, in accordance with some example embodiments.
Figure 9B:
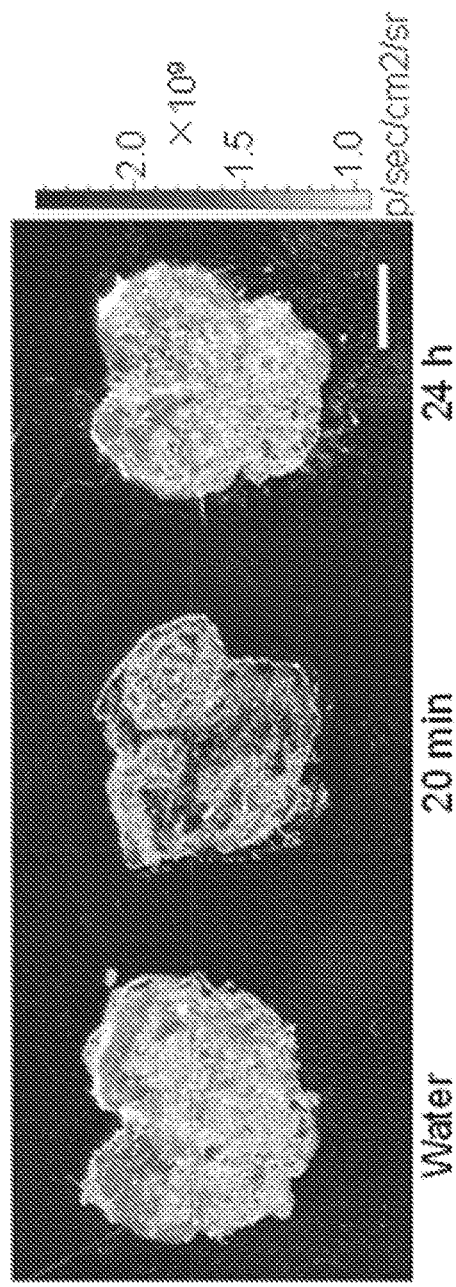

FIGS. 9A and 9B show data plots and images of example results depicting recovery of the gastric pH post micromotor treatment. The data plot of FIG. 9A depicts an example of in vivo gastric pH values using a mouse model (n=3) measured 20 min and 24 hours post administration of 5 mg of Mg micromotors, with mice administrated with water were used as a control. To determine the recovery of gastric pH after a Mg micromotor treatment, for example, the pH of stomach content can be measured at 20 minutes and 24 hours after administration of the micromotors. After the pH change induced by the Mg micromotors, the mean gastric pH returned to 2.16 within 24 hours post-treatment, e.g., which is close to pH 1.88 of the control group treated with deionized water. To confirm the in vivo recovery of gastric pH, for example, the pH indicator BCECF with a pKa of approximately 6.98 was used. The stomachs were dissected along the greater curvature and excess gastric content was removed. BCECF fluorescence dye was evenly distributed and mixed with the gastric contents on the stomach tissues. Fluorescence imaging of BCECF was performed on the different treatment groups.

FIG. 9B depicts examples of fluorescent images of the pH indicator BCECF superimposed on the entire stomach for the samples in FIG. 9A. When the environmental pH is greater than its pKa, for example, BCECF may exhibit a strong fluorescence emission, as shown by the stomach sample treated with micromotors for 20 minutes. In contrast, 24 hours after administrating the Mg micromotors, the gastric content labeled with BCECF indicator showed weak fluorescence intensity, reflecting a low pH condition. The example results from FIG. 9A-9B indicate a transient pH neutralization effect from the Mg micromotors and that the normal acidity of gastric content can be recovered following the micromotor treatment.

The gastric toxicity of the administrated Mg micromotors was evaluated. For example, the toxicity to mice was evaluated by orally administering 5 mg of Mg micromotor or DI water and monitoring for general toxicity symptoms every 2 hours for the first 10 hours post-administration. Observable signs may include signs of pain such as hunched posture, unkempt fur, or lethargy. In mice, no signs were observed in both groups. The example Mg micromotor's toxicity was further determined by histological analysis.

FIGS. 10A and 10B show images of a toxicity evaluation using example Mg micromotors. As shown in FIG. 10A, in mice a hematoxylin and eosin (H&E) stained cross-section of glandular stomach from the micromotor-treated group showed intact glandular mucosa with no signs of superficial degeneration of columnar epithelial cells or erosion. There was no observable difference in the crypt and villus size and number, or mucosal thickness, between the micromotor-treated and water-treated groups. Moreover, lymphocitic infiltration into the mucosa and submucosa was not apparent, implicating no sign of gastric inflammation. The potential toxicity of the Mg micromotors was further evaluated using gastric tissue sections by a terminal deoxynucleotidyl transferase-mediated deoxyuridine triphosphate nick-end labeling (TUNEL) assay to determine the level of gastric epithelial apoptosis as an indicator of gastric mucosal homeostasis. No apparent increase in gastric epithelial apoptosis was observed for micromotor-treated groups as compared to the water control group, as shown in FIG. 10B. Thus, the in vivo toxicity studies indicated no interference in gastric pH homeostasis, and no apparent gastric histopathologic change or inflammation. As such, the oral administration of Mg micromotors is safe in at least mice model. The Mg micromotors can thus temporarily adjust the stomach pH without adverse effects, making them an attractive vehicle for gastric drug delivery.

The example acid-powered micromotors in accordance with the present technology can operate as an active microdevice to efficiently and temporarily adjust local physiological parameters in vivo for diverse biomedical applications. As demonstrated in example implementations, the reaction of the micromotor's magnesium core with the gastric fluid leads to rapid proton depletion and thus acid neutralization without affecting the normal stomach function or causing adverse effects, making these synthetic micromotors an attractive alternative to proton pump inhibitors. The fast and efficient neutralization reflects the localized fluid convection generated by the micromotor movement. When coupled to a pH-sensitive payload-containing polymer coating, this pH change can lead to autonomous release of the encapsulated cargo. The microvehicle thus combines self-propulsion, acid neutralization, along with cargo transport and release. The Mg engine may convert the acid fuel to propulsion force and simultaneously alter the local pH that leads to payload release from the pH-sensitive coating. As such, the micromotor-based delivery vehicle can actively adjust the local environment to achieve desired conditions for triggered payload release.

Example Implementations Using Micromotor-Enabled Active Drug Delivery for in Vivo Treatment of Stomach Infection In some aspects, chemically-powered microscale and/or nanoscale motors in accordance with the present technology can be implemented for active drug delivery for in vivo therapeutic applications. For example, the chemically-powered micro-/nano-motors can be used for treatment of gastric bacterial infection by controlled delivery of antibiotic drugs. In an example, clarithromycin is an antibiotic drug that can be carried by the example micro-/nano-motors to treat *Helicobacter pylori* infection in a living organism. Example implementations are described herein that demonstrate active propulsion of drug-loaded magnesium-based micromotors in the acidic gastric media, e.g., which can enable effective delivery of the antibiotic drug, leading to significant reduction of bacteria burden in the stomach compared to passive drug carriers, with no apparent toxicity observed. Also, for example, the example micro/nano-motor delivery system are shown to eliminate the use of proton pump inhibitor (PPI) prior to drug administration, e.g., which can be attributed to the motors' built-in proton depletion function associated with their locomotion process. These self-propelled micromotors provide unique features for in vivo gastric drug delivery that are difficult, if not impossible, to achieve for the passive delivery systems.

Recent advances in the nano/micromotor field in terms of improvement of biocompatibility and biological function have led to their growing use in biomedicine, including therapeutic payload delivery, micro-surgery, isolation of biological targets, operation within living cells, and removal of toxicant molecules and organisms. Although significant progress has been accomplished to demonstrate the in vitro capabilities of nano/micromotors to transport therapeutic cargos to target destinations, tremendous effort is still required to translate the proof-of-concept research to effective in vivo biomedical applications.

For applications in living organisms, utility and performance of motor-based active transport systems should be investigated. For example, the biocompatibility and in vivo performance of zinc-based and magnesium (Mg)-based micromotors has been explored under in vivo conditions, as discussed above. Example studies of such micromotors for gastrointestinal systems have shown that the engineered micromotors can self-propel in the stomach and intestinal fluids for enhanced retention in the gastric mucous layer and targeted delivery in the gastrointestinal tract. Such example in vivo studies of synthetic motors have significantly advanced the potential of adoption of micro/nanomotor technology, and cleared a path towards direct evaluation of disease-oriented therapeutic efficacy associated with motor-enabled active drug delivery. However, still remains.

Disclosed are example embodiments in accordance with the present technology of micro- and/or nano-motor devices (e.g., Mg-based micromotors) loaded with an antibiotic drug (e.g., clarithromycin (CLR)) for in vivo treatment of gastrointestinal maladies (e.g., *H. pylori* infection). For example, in implementations, given the built-in proton depletion function, the example micro/nanomotor-based therapy is able to undergo the harsh gastric environment to achieve remarkable antibacterial efficacy without involving the commonly used proton pump inhibitors (PPIs).

For example, *H. pylori* bacteria is found in about half of the world's population, and can cause stomach infection and subsequently lead to diverse gastric and extragastric diseases. In most cases, the administration of antibiotics for the treatment of *H. pylori* infection is combined with the use of PPIs to reduce the production of gastric acid, because the gastric acid could make antibiotics less effective. The effectiveness of PPIs is attributed to the irreversible binding to proton pumps and thus to suppress acid secretion, which in long term use can lead to adverse effects such as headache and diarrhea and in more serious scenarios cause anxiety or depression. Therefore, it would be highly beneficial to develop an alternative therapeutic regimen with equivalent or advantageous therapeutic efficacy as the current antibiotic treatments while excluding the use of PPIs.

In some embodiments in accordance with the present technology, a chemical-propulsion microstructure device includes a magnesium microsphere; a coating including titanium oxide affixed to the magnesium microsphere, in which the coating includes an opening at one portion of the magnesium microsphere to expose a magnesium surface; a polymer layer affixed to the coating; and a payload material at least partially encapsulated by the polymer layer, in which the chemical-propulsion microstructure device is operable to undergo a chemical reaction between magnesium and acid when the chemical-propulsion microstructure device are placed in an acidic solution.

Example implementations of the chemical-propulsion microstructure device include any of the following examples. For example, the opening can provide contact between the magnesium surface and the acid. The chemical-propulsion microstructure device can include a Janus microstructure. In some embodiments, the device includes an outer layer over the polymer layer. For example, the outer layer can include chitosan (e.g., of a thickness of approximately 100 nm). For example, the coating including titanium oxide layer can provide a biocompatible shell scaffold to maintain a spherical shape and the opening size during the propulsion of the chemical-propulsion microstructure. For example, the payload material can include an antibiotic drug, e.g., such as clarithromycin (CLR). For example, the chemical-propulsion microstructure is operable to undergo an acidic gastric environment to deliver antibacterial substances in a gastrointestinal organ without involving proton pump inhibitors (PPIs). For example, the chemical reaction generates hydrogen microbubbles to propel the chemical-propulsion microstructure in stomach fluid, such that the opening allows a slow chemical reaction process and gradual dissolution of the magnesium microsphere to prolong life of the chemical-propulsion microstructure. For example, the prolonged life of the chemical-propulsion microstructure can include at least 6 minutes.

An example embodiment of Mg-based micromotors loaded with CLR drug were used in an example study to demonstrate their functionality for treating *H. pylori* bacteria in a mouse model. The example Mg-based micromotors included a combination of a CLR-loaded poly(lactic-co-glycolic acid) (PLGA) layer and a chitosan polymer layer covering on a propellant Mg core, e.g., which provides high drug loading capacity, along with biodegradability and biocompatibility. In some implementations, the micromotors include a positively-charged chitosan outer coating that enables adhesion of the motor onto the stomach wall, facilitating efficient localized autonomous release of CLR from the PLGA polymer coating.

In contrast to acid suppression by PPIs, for example, the Mg-based micromotors can temporally and physically alter the local acidic environment by quickly depleting protons while propelling within the stomach. Such elimination of the PPI administration is coupled with significant reduction of bacteria burden, as demonstrated in the example in vivo study using a mouse model. Using a mouse model of *H. pylori* infection, the propulsion of the drug-loaded Mg-based micromotors in gastric fluid along with their outer chitosan layer are shown to greatly enhance the binding and retention of the drug-loaded motors on the stomach wall. As these micromotors are propelled in the gastric fluid, their Mg cores are dissolved, leading to self-destruction of these motors without harmful residues, as is demonstrated by the example toxicity studies.

The example Mg-based micromotors are capable of efficient locomotion in the acidic stomach environment, and provide a built-in proton depletion ability, active and prolonged retention within the stomach wall, and high drug-loading capacity. As shown by the following results from the example study, an in vivo therapeutic application of chemically-powered micromotors provides an examination of the therapeutic efficacy, distribution and retention of the micromotors in the mouse stomach compared to passive drug-loaded microparticles and other control groups, along with corresponding in vivo toxicity profile. These example results illustrate the attractive therapeutic capabilities of acid-driven micromotors, which open the door for in vivo therapeutic applications of body-fluid propelled micromotors towards the treatment of a variety of diseases and disorders.

Example results of the example study are described, as well as example techniques for preparation and characterization of drug-loaded Mg-based micromotors.

FIGS. 11A-11K show schematic diagrams and example results of example embodiments of drug-loaded Mg-based micromotors and methods of manufacture in accordance with the present technology. FIG. 11A shows an illustrative diagram depicting a method for producing example drug-loaded Mg-based micromotors. FIG. 11B shows an illustrative diagram depicting in vivo propulsion and drug delivery of drug-loaded Mg-based micromotors (labeled 1110) in a mouse stomach. FIG. 11C shows a panel of time-lapse images (e.g., 2 min intervals, I-III) of the propulsion of the drug-loaded Mg-based micromotors in simulated gastric fluid (pH~1.3).

FIG. 11D shows an illustrative diagram of an example embodiment of the drug-loaded Mg-based micromotor 1110. The example drug-loaded Mg-based micromotor 1110 depicts an example embodiment of the GI nano/micromotor 110. The drug-loaded Mg-based micromotor 1110 include a magnesium microsphere 1111, and a coating 1112 including titanium oxide affixed to the magnesium microsphere, in which the coating includes an opening at one portion of the magnesium microsphere to expose a magnesium surface of the microsphere 1111. The drug-loaded Mg-based micromotor 1110 includes a polymer layer 1113 affixed to the coating 1112, and a payload material 1114, e.g., a drug at least partially encapsulated by the polymer layer 1113. For example, the payload 1114-encapsulated polymer layer 1113 can include a biocompatible copolymer material, e.g., such as poly(lactic-co-glycolic acid) (also known as PLGA). In some embodiments, the drug-loaded Mg-based micromotor 1110 includes an outer layer 1115, e.g., a chitosan layer. The drug-loaded Mg-based micromotor 1110 is operable to undergo a chemical reaction between magnesium and acid when the chemical-propulsion microstructure device are placed in an acidic solution.

FIGS. 11E-11K show images of the example drug-loaded Mg-based micromotors. FIG. 11E shows a SEM image of a drug-loaded Mg-based micromotor. FIGS. 11F and 11G show EDX spectroscopy images illustrating the distribution of (f) magnesium and (g) titanium in the micromotor. FIGS. 11H-11K show optical microscopy images of dye-loaded Mg-based micromotor, i.e., (h) optical image, and fluorescence images showing the dye-loaded Mg-based micromotors in the (i) DiD channel (PLGA layer), (j) FITC channel (chitosan layer), along with an overlay of the two channels (k).

FIG. 11A shows an illustrative diagram of example drug-loaded Mg-based micromotors and a method to fabricate the example drug-loaded Mg-based micromotors. As shown in FIG. 11A, the method includes Mg microparticles dispersion over a surface, e.g., glass slide (panel I). The method includes depositing a material layer, e.g., $TiO_2$ atomic layer deposition (ALD), over the Mg microparticles (panel II). The method includes depositing drug-loaded PLGA over the Mg/$TiO_2$ microparticles (panel III). The method includes depositing a chitosan polymer layer over the Mg/$TiO_2$/PLGA microparticles (panel IV). The example drug-loaded Mg-based micromotors includes a core including a Mg microparticle, e.g., some examples having an average size of ~20 μm. In the example study, a layer of Mg microparticles was dispersed onto a glass slide (FIG. 11A, panel I), followed by an asymmetrical coating of the microspheres with a thin $TiO_2$ layer using atomic layer deposition (ALD) (FIG. 11A, panel II). The ALD process leads to a $TiO_2$ uniform coating over the Mg-microspheres, while leaving a small opening (essential for contact with the acid fuel) at the sphere-glass contact point, which forms a Janus microstructure. Such biocompatible $TiO_2$ layer acts as a shell scaffold that maintains the micromotor spherical shape and the opening size during the propulsion, leading to consistent and prolonged operation. The Mg/$TiO_2$ Janus microparticles were then coated with a PLGA film containing the CLR antibiotic payload (FIG. 11A, panel III). After the drug loading step, the microparticles were coated with an outer thin chitosan layer (thickness~100 nm) that ensures efficient electrostatic adhesion of the micromotors to the mucosal layer on the stomach wall while protecting the CLR-loaded PLGA layer (FIG. 11A, panel IV). The resulting CLR-loaded Mg-based micromotors were separated and collected by soft mechanical scratching of the glass slide, leaving a small opening for spontaneous Mg-acid reaction when the motors are placed in an acidic solution. This reaction generates hydrogen microbubbles and leads to efficient propulsion in the stomach fluid. The small opening enables also a slow reaction process and gradual dissolution of the Mg core, leading to a prolonged micromotor lifetime, e.g., which can be of approximately 6 min in some implementations. The in vivo self-propulsion in the gastric fluid of a stomach and the corresponding drug delivery process from the PLGA layer of the Mg-based micromotors are illustrated schematically in FIG. 11B.

The ability of drug-loaded Mg-based micromotors to efficiently propel in gastric acid was first tested in vitro by using a simulated gastric fluid (pH~1.3). The microscopic images in FIG. 11C (taken at 2 min intervals) illustrate the fast and prolonged autonomous propulsion of a CLR-loaded Mg-based micromotor in the gastric fluid simulant. The efficient hydrogen bubble generation propels the micromotors rapidly, with an average speed of ~120 μm/s, and indicates that the Mg-based micromotors can react and move fast in the gastric fluid. Such efficient micromotor propulsion is essential for the motors to reach stomach wall and thus achieving high therapeutic efficacy. Importantly, the acid-Mg reaction responsible for the autonomous propulsion also spontaneously depletes protons in gastric fluid and thus neutralizes the stomach pH without using PPIs.

FIG. 11D schematically illustrates an example structure of a drug-loaded Mg-based micromotor, showing the Mg core, covered mostly with the $TiO_2$ shell layer, drug-loaded PLGA layer, and an outer chitosan layer. The drug-loaded Mg-based micromotors were carefully characterized. An example SEM image of a drug-loaded micromotor (shown FIG. 11E) confirms the presence of a small opening (~2 μm) on the spherical micromotor, produced during the coating process, that exposes the Mg core of the micromotor to the gastric fluid and facilitates the hydrogen bubble thrust. Energy-dispersive X-ray (EDX) spectroscopy mapping analysis was carried out to confirm the motor composition. The resulting EDX images, shown in FIGS. 11F and 11G, illustrate the presence and distribution of magnesium and titanium, respectively.

An example fluorescence study was carried out to confirm efficient drug-loading within the PLGA layer and the coating of the micromotor with the protective and adhesive chitosan layer. This was accomplished by preparing Mg-based micromotors with the PLGA and chitosan coatings containing the fluorescent dyes 1,1'-dioctadecyl-3,3,3',3'-tetramethylin-dodicarbocyanine, 4-chlorobenzenesulfonate salt (DiD, $\lambda_{em}$=665 nm) and fluorescein isothiocyanate-dextran (FITC, $\lambda_{em}$=520 nm), respectively. An optical image of a dye-loaded micromotor is displayed in FIG. 11H. The corresponding fluorescence images show the dye-loaded Mg-based micromotor in the DiD and FITC channels (FIG. 11I, FIG. 11J, respectively); an overlay of the two channels is displayed in FIG. 11K. The high fluorescent intensity of the loaded dyes confirms the successful coating of the micromotor with both PLGA and chitosan layers, along with the high cargo-loading capacity of the micromotor.

Figures 12A, 12B, 12C, 12D:
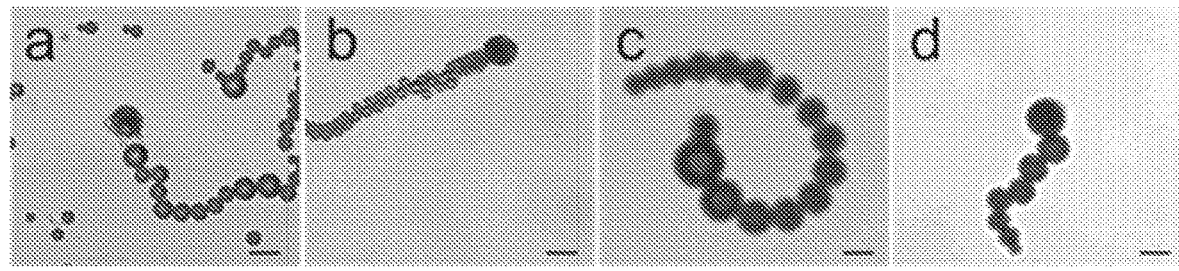
FIGS. 12A-12I show images and a data plot depicting an example propulsion characterization of the drug-loaded Mg/TiO2/PLGA/Chitosan Janus micromotors.
Figures 12E, 12F, 12G, 12H:
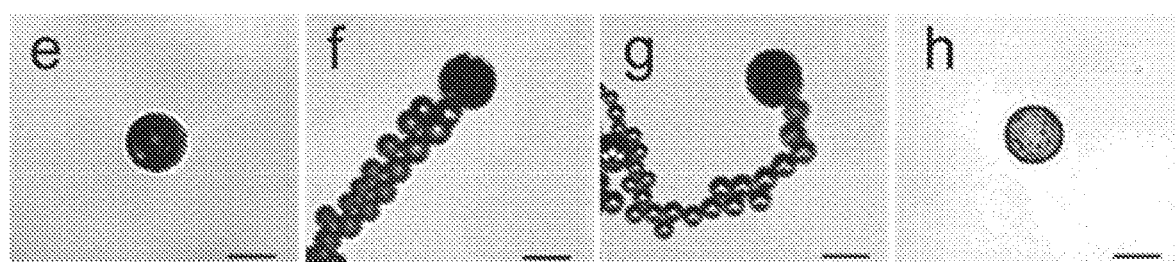
Figure 12I:
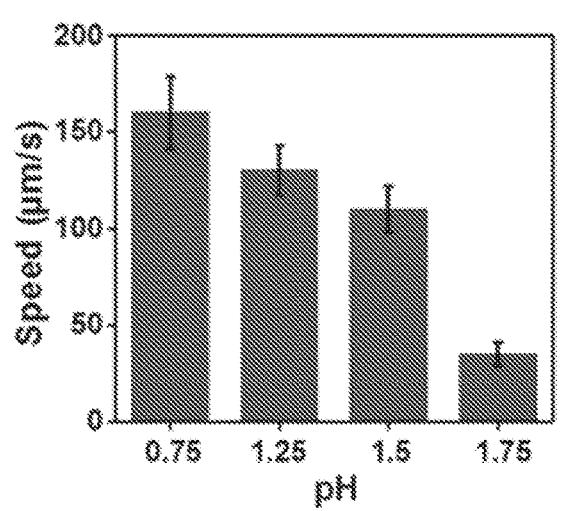

Prior to the example in vivo therapeutic application of the Mg-based micromotors, several in vitro studies were performed. Initially, the ability of drug-loaded micromotors to efficiently propel in gastric acid was tested in vitro. FIGS. 12A-12D show time-lapse images showing the motion of the drug-loaded Mg-based micromotors in simulated gastric fluid adjusted to different pH (0.75, 1.25, 1.5, and 1.75, a-d, respectively). Time-lapse images in FIGS. 12E-12H show the lifetime of a drug-loaded micromotor in gastric fluid simulant (pH~1.3) to be approximately 6 min. FIG. 12I show the pH-dependent speed of the micromotor in the gastric fluid simulant. The micromotor speed drastically decreases upon changing the pH of the gastric fluid solution from pH 1.5 to 1.75. Assuming that the stomach pH is 1.3, the drug-loaded Mg-based micromotors can efficiently move at this condition with an average speed of ~120 μm/s (e.g., ~6 body lengths $s^{-1}$).

FIGS. 12A-12I show images and a data plot depicting an example propulsion characterization of the drug-loaded Mg/TiO2/PLGA/Chitosan Janus micromotors. Time-lapse images of FIGS. 12A-12D show the motion of the drug-loaded Mg-based Janus micromotors in (a) pH 0.75, (b) pH 1.25, (c) pH 1.5, and (d) pH 1.75, respectively. Time-lapse images of FIGS. 12E-12H show the lifetime of the drug-loaded Mg/TiO2/PLGA/Chitosan Janus micromotor in simulated gastric fluid (pH~1.3) from 0 min, 1 min, 5 min, and 8 min after gastric fluid simulant addition, respectively. FIG. 12I shows a data plot depicting the dependence of the micromotor speed upon the gastric fluid pH. Example scale bar, 20 am; surfactant level, 1% Triton X-100.

Figure 13A:
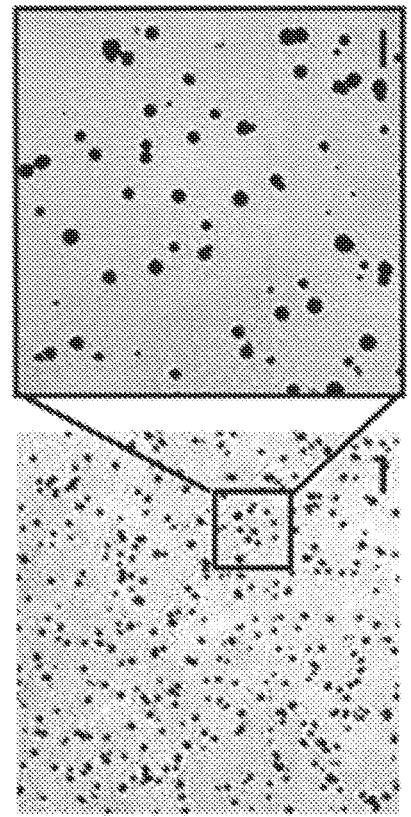
FIGS. 13A-13D show example illustrations, images and data plots depicting an example implementation of antibiotic drug loading of the Mg-based micromotors and in vitro bactericidal activity.

Example techniques for drug loading optimization and in vitro bactericidal activity. In the example study, the CLR loading onto the Mg-based micromotors was optimized to achieve a clinically-relevant therapeutic concentration of the drug (15-30 mg/kg/day). FIG. 13A shows a schematic displaying the loading of CLR onto the micromotors. For example, the $Mg/TiO_2$ microparticles dispersed onto a glass slide (~2 mg of Mg microparticles per glass slide) were coated with a PLGA solution prepared in ethyl acetate, which was mixed with CLR (see detailed experimental protocol in Methods section). Rapid evaporation under nitrogen current leads to the formation of a homogeneous PLGA/CLR coating over the $Mg/TiO_2$ microparticles (microscope images of the coated micromotors are displayed in FIG. 13B). The microparticles were further coated with chitosan before quantifying the CLR loading efficiency of the micromotors. For example, to optimize the drug loading, Mg-based micromotors were coated with PLGA solutions containing different amounts of CLR (between 4 mg and 6 mg). By studying different combinations of the PLGA/CLR solution volume and CLR concentration, for example, the highest CLR loading efficiency (e.g., 26%, corresponding to 1032±37 μg per 2 mg micromotor) was obtained when coating the microparticles with 120 μL of the PLGA solution containing 4.8 mg of CLR (FIG. 13C, II). This example formulation offered optimal CLR loading and was selected for subsequent in vitro and in vivo anti-*H. pylori* studies.

Once confirmed that the micromotors were capable to load antibiotic cargo with high loading efficiency, an example study of the in vitro bactericidal activity of CLR-loaded Mg-based micromotors against *H. pylori* was performed. To mimic the gastric environment, for example, samples were treated in 0.1 N HCl for 1 h prior to incubation with bacteria. This also ensured the dissolution of micromotors and consecutive drug release. FIG. 13D shows the enumerated amount of bacteria after being treated by CLR-loaded Mg-based micromotors or free CLR solution with varying concentrations of CLR. According to the example results, drug-loaded micromotors exhibited a comparable bactericidal activity to free drug solution over the whole range of concentrations used in the study. Specifically, it was determined that the minimal bactericidal concentration (MBC) values of the samples, defined as the minimal concentration of an antimicrobial agent that kills 3 logs (99.9%) of the bacteria. The MBC value for CLR-loaded Mg-based micromotors was found to be 0.25 µg/mL, which was unaltered from the MBC value of free CLR. Moreover, bare Mg-based micromotors with corresponding amount of motors were used as negative controls. From FIG. 13D, the bare motors had negligible effect on the viability of *H. pylori* over the studied range, which supports that the bactericidal effect of CLR-loaded Mg-based micromotors is solely due to the loaded antibiotics, not the other compositions of the micromotor carrier. Overall, FIG. 13D verifies that the activity of the loaded drug was not compromised compared to free drug. The example findings validate the potential use of these drug-loaded micromotors for therapeutic applications.

Figure 13B:
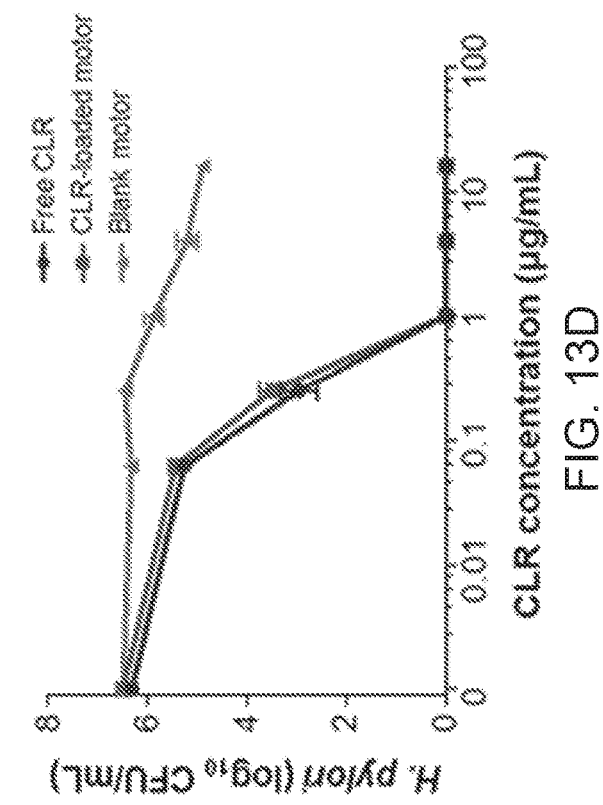
Figure 13C:
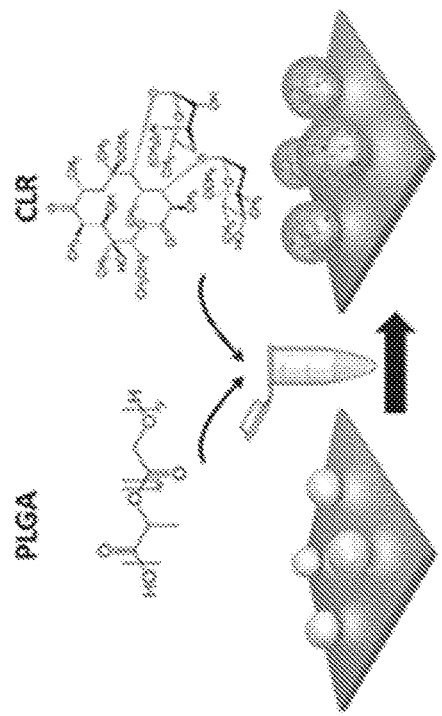
Figure 13D:
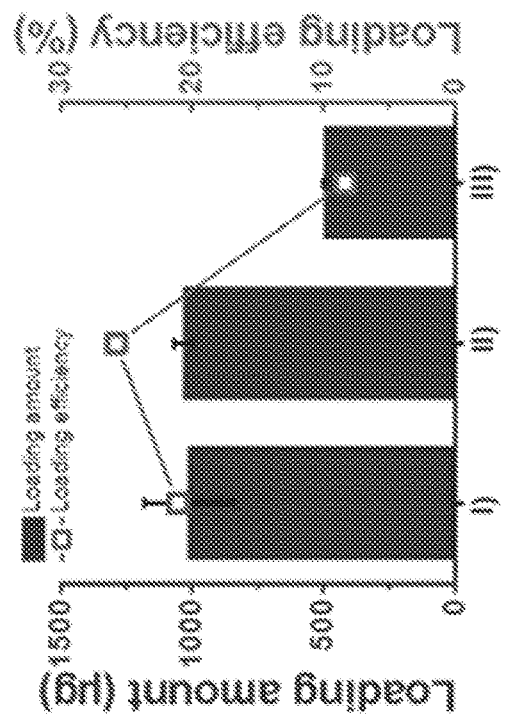

FIGS. 13A-13D show example illustrations, images and data plots depicting an example implementation of antibiotic drug loading of the Mg-based micromotors and in vitro bactericidal activity. FIG. 13A shows a schematic displaying the loading clarithromycin (CLR) onto the Mg-based micromotors. PLGA polymer dissolved in ethyl acetate is mixed with CLR, and the solution is deposited over the Mg/TiO$_2$ microparticles resulting in the formation of a thin PLGA/CLR coating. FIG. 13B shows microscope images showing the PLGA/CLR film over the Mg-based micromotors. Scale bars are 100 µm and 40 µm, respectively. FIG. 13C shows a data plot depicting quantification of CLR loading amount and yield of the micromotors prepared with different CLR solutions: (I) 100 µL of 40 mg/mL CLR solution, (II) 120 µL of 40 mg/mL CLR solution, and (III) 200 µL of 30 mg/mL CLR solution. All the CLR-loaded Mg-based micromotors were coated with a thin chitosan layer; all samples were dissolved in acid for 24 h before the drug loading measurement. FIG. 13D shows a data plot depicting in vitro bactericidal activity of free CLR, CLR-loaded Mg-based micromotors and blank Mg-based micromotors (without CLR drug) against *H. pylori* bacteria.

Figure 14A:
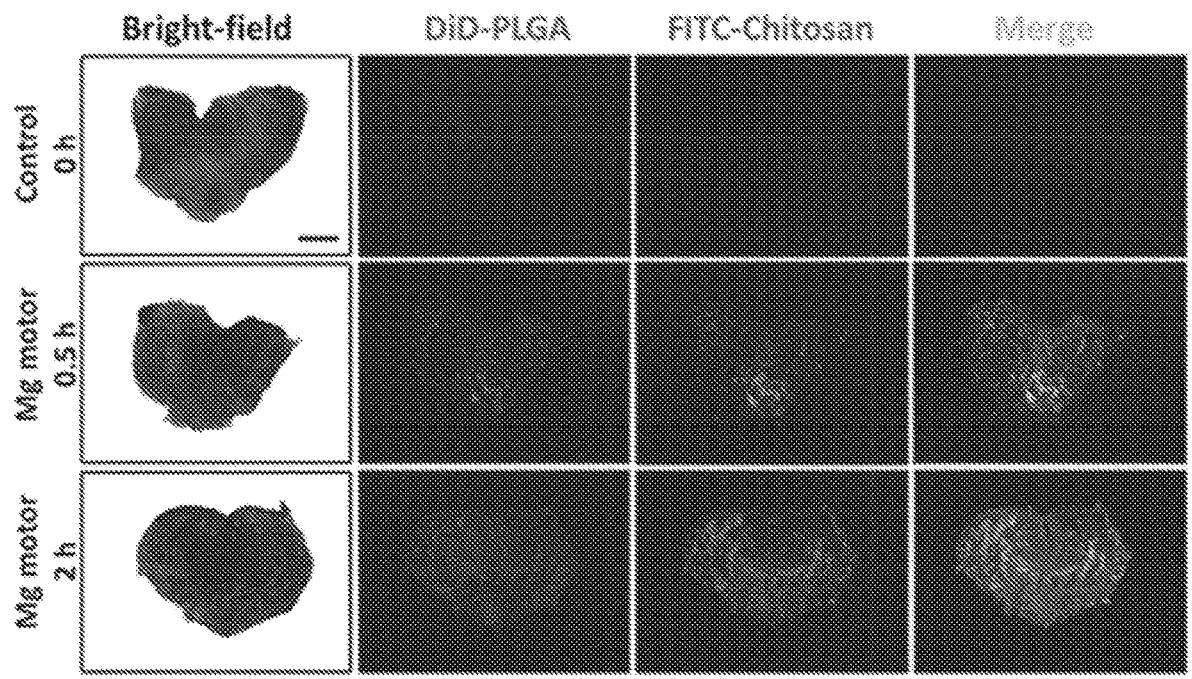
FIGS. 14A and 14B show images and a data plot depicting retention of the example Mg-based micromotors in mouse stomachs.

Example techniques for in vivo micromotor retention in mouse stomach. After the optimization of drug loading onto the example Mg-based micromotors and the confirmation of effective in vitro bactericidal activity, the micromotors were further investigated under in vivo setting. First, the in vivo retention properties of the Mg-based micromotors on stomach tissue were examined at different post-administration times, and compared with control groups administered with DI water, shown in FIGS. 14A and 14B. For example, Mg-based micromotors prepared with DiD-labeled PLGA and FITC-labeled chitosan coatings were administered to a group of mice (n=3), and following 30 min and 2 h of the samples administration, the mice were sacrificed and the entire stomach was excised and opened. Subsequently, the luminal lining was rinsed with PBS and flattened for imaging. Accordingly, FIG. 14A shows bright-field and fluorescence images of the luminal lining of freshly excised mouse stomach at 0 min after oral gavage of DI water, and at 30 min and 2 h after oral gavage of Mg-based micromotors. As can be observed, the images corresponding to the dye-loaded Mg-based micromotors show an intense fluorescent signal in both red and green light channels, which indicates efficient distribution and retention of the micromotors in the mouse stomach. The continuous propulsion of the micromotors and the adhesive properties of the chitosan coating help to achieve a homogeneous distribution of the micromotors in the stomach. The corresponding fluorescence quantification of the dye-loaded micromotors retained in the mouse stomach after 30 min and 2 h oral gavage of the sample is displayed in FIG. 14B. The graphic represents the higher fluorescence signals obtained at 665 nm and 520 nm (corresponding to DiD and FITC dyes, respectively) for each sample. These example results indicate that the micromotors can effectively propel in gastric fluid and are retained in the stomach wall, where the *H. pylori* bacteria reside.

Figure 14B:
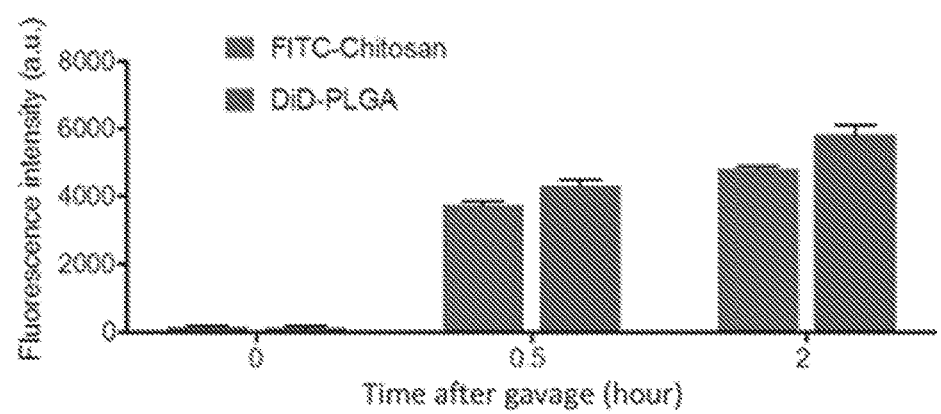

FIGS. 14A and 14B show images and a data plot depicting retention of the example Mg-based micromotors in mouse stomachs. FIG. 14A shows Bright-field and fluorescence images of the luminal lining of freshly excised mouse stomachs at 0 min after oral gavage of DI water (control), and at 30 min and 2 h after oral gavage of the Mg-based micromotors. Scale bar, 500 mm. FIG. 14B shows a data plot of corresponding fluorescence quantification of all the images shown in FIG. 14A.

Figure 15A:
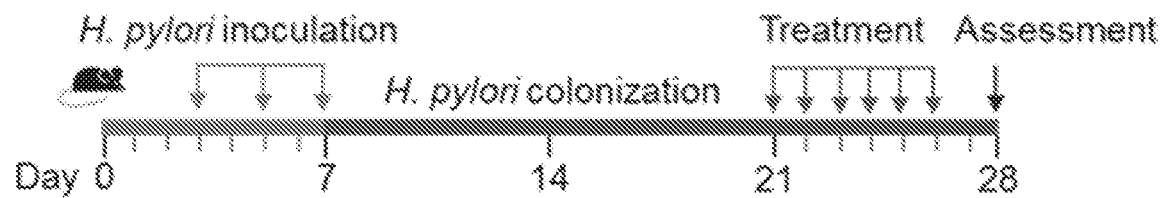
FIGS. 15A and 15B show example in vivo anti-*H. pylori* therapeutic efficacy data.

Example techniques for in vivo anti-*H. pylori* therapeutic efficacy are described. The example study included in vivo therapeutic efficacy of the drug-loaded Mg-based micromotors against *H. pylori* infection. Prior to the therapeutic study, for example, *H. pylori* infection was developed in a mouse model using C57BL/6 mice. Each mouse was inoculated with 3×10$^8$ CFU *H. pylori* SS1 in brain-heart infusion (BHI) broth by oral gavage three times on day 3, 5, and 7 (FIG. 15A). Two weeks after inoculation, the *H. pylori* infected mice were divided into five groups (n=6 for each group) and treated with DI water, blank Mg-based micromotors (without CLR drug), free CLR drug with PPI (CLR+PPI), CLR-loaded silica microparticles, or CLR-loaded Mg-based micromotors once a day for 5 days. Mice in the free CLR+PPI group received proton pump inhibitor (PPI) 30 min before administrating CLR to neutralize gastric acid and prevent potential degradation of CLR. After the treatment course, the bacterial burden was evaluated by enumerating and comparing *H. pylori* counts recovered from each mouse stomach. The mean bacterial burden from two negative control groups treated with DI water and blank Mg-based motors were 2.1×10$^7$ and 1.4×10$^7$ CFU/g of stomach tissue, respectively (FIG. 15B), black and orange color, respectively). Meanwhile, a bacterial burden of 3.0×10$^6$ CFU/g was measured from the mice treated with CLR-loaded silica microparticles, which did not show statistical difference to the negative controls. In contrast, for example, when the mice were treated with CLR-loaded Mg-based micromotors, the bacterial burden was quantified as 2.9×10$^5$ CFU/g, a significant reduction compared to the negative control and CLR-loaded silica microparticle groups.

Figure 15B:
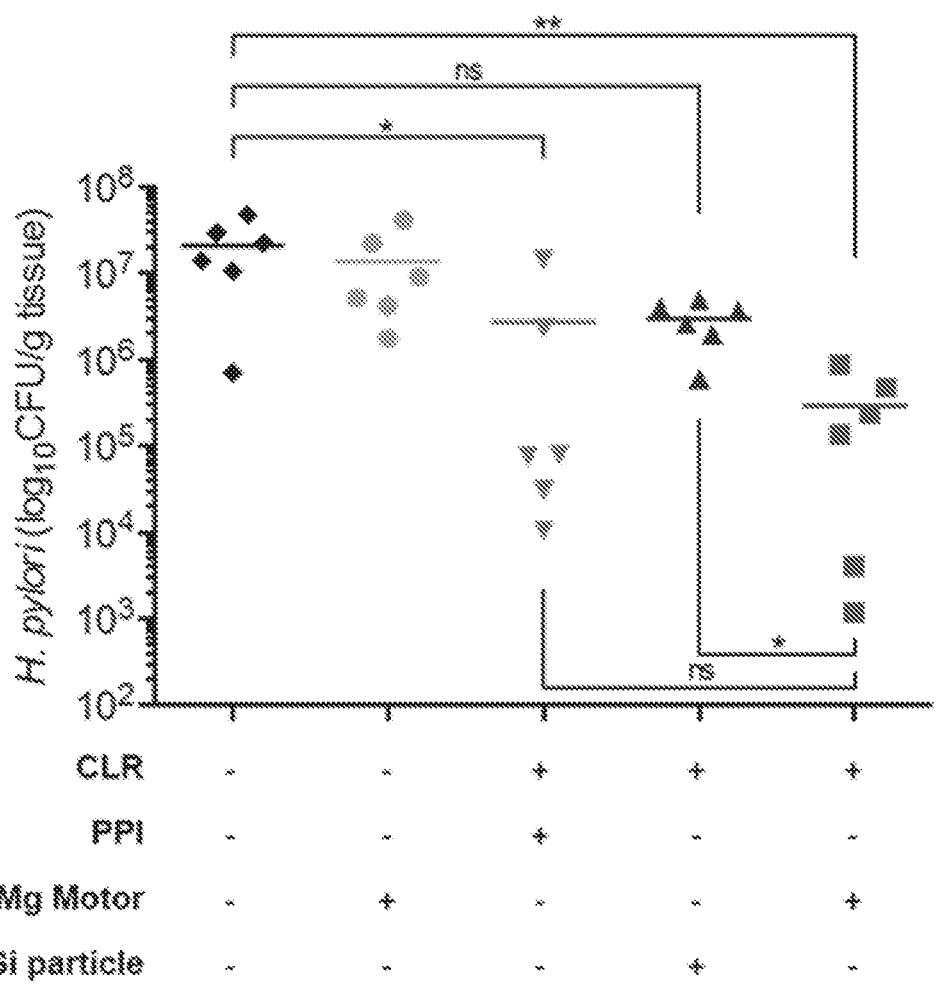

FIGS. 15A and 15B show example in vivo anti-*H. pylori* therapeutic efficacy data. FIG. 15A shows a diagram of the example study protocol including *H. pylori* inoculation and infection development in C57BL/6 mice, followed by the treatments. FIG. 15B shows a data plot depicting quantification of bacterial burden in the stomach of *H. pylori*-infected mice treated with DI water (black color), bare Mg-based micromotors (orange color), free CLR+PPI (green color), CLR-loaded silica microparticles (blue color), and CLR-loaded Mg-based micromotors (red color), respectively (n=6 per group). Example bars represent median values. *P<0.05, **P<0.01, ns=no statistical significance.

The substantial improvement in *H. pylori* reduction demonstrates the benefit of acid-powered Mg-based micromotors compared to static micron-sized carriers. A bacterial burden of 2.8×10$^6$ CFU/g was obtained for the positive control mice with free CLR+PPI treatment. The difference between example CLR-loaded Mg-based micromotors and the free CLR+PPI groups were not statistically significant. However, the example CLR-loaded micromotors reduced the *H. pylori* burden in mice compared with in the negative controls by ~1.8 orders of magnitude, whereas the free CLR+PPI group reduced it only by ~0.8 orders of magnitude. Moreover, for example, looking at the bacterial burden in each tested mice, it was found that 2 out of 6 mice from the CLR-loaded micromotors group displayed a significant reduction by 4 order of magnitude of bacteria burden which are the lowest among all other treatment groups. These analyses highlight the enhanced performance of Mg-based micromotors compared to free drug and emphasize the benefit of the propulsion-enabled active drug delivery in the stomach. These example results demonstrate that the Mg-based micromotors can effectively propel and distribute throughout the stomach of living mice, and perform effective therapeutic activity.

Figure 16:
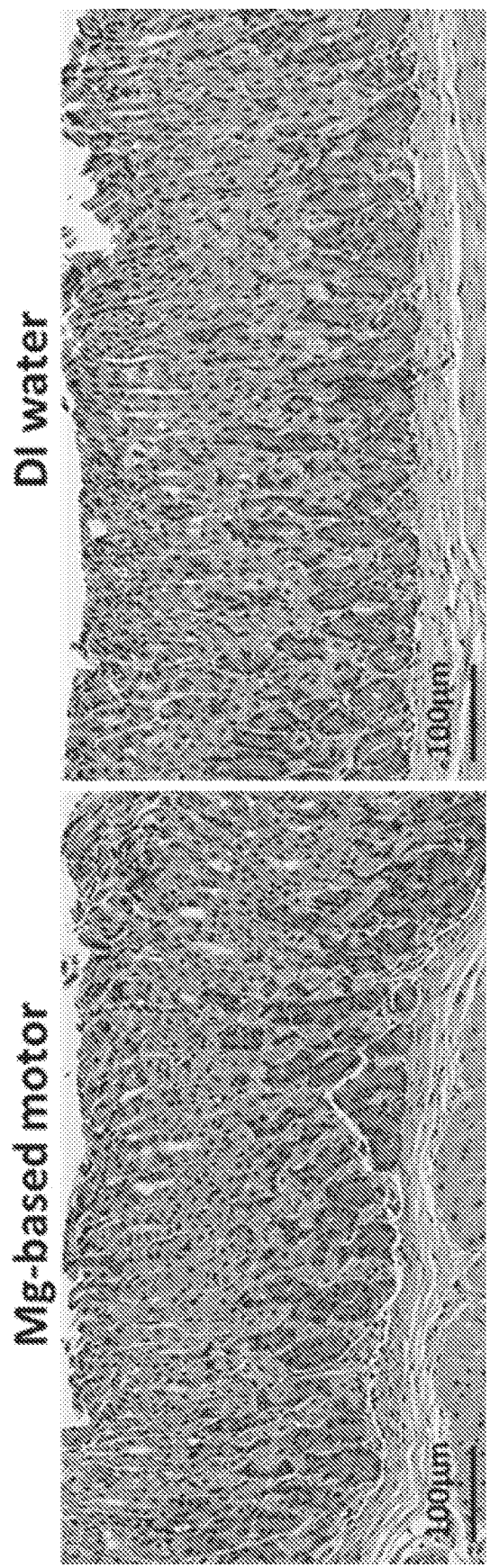
FIG. 16 shows images of example in vivo toxicity results using example Mg-based micromotors.

Example techniques for in vivo toxicity evaluation of Mg-based micromotors are described. The gastric toxicity of the administrated Mg-based micromotors was evaluated. Healthy mice were orally administered with Mg-based micromotors or DI water once daily for 5 consecutive days. Throughout the treatment, no signs of distress such as squinting of eyes, hunched posture, unkempt fur, or lethargy were observed in both groups. On day 6, mice were sacrificed and their stomachs were processed for histological staining. Longitudinal sections of the glandular stomach were stained with hematoxylin and eosin (H&E), shown in FIG. 16. The stomach section of the micromotor-treated group showed undamaged structure of columnar epithelial cells with no signs of superficial degeneration or erosion (FIG. 16, left). There was no noticeable difference in the gastric mucosal integrity, in terms of thickness as well as size and number of crypt and villus, between the motor-treated and DI water-treated groups (FIG. 16, right). No lymphocytic infiltration into the mucosa and submucosa was observed, implicating no sign of gastric inflammation. The in vivo toxicity study of Mg-based micromotors showed no alteration of gastric histopathology or observable inflammation, indicating that the treatment of Mg-based micromotors is safe in the mouse model.

FIG. 16 shows images of example in vivo toxicity results using Mg-based micromotors. Uninfected mice were orally administered with the Mg-based micromotors or DI water once daily for 5 consecutive days. On day 6, mice were sacrificed and sections of the mouse stomach tissue were processed for histological staining with hematoxylin and eosin (H&E). Scale bars of FIG. 16 are 100 μm.

Figure 17A:
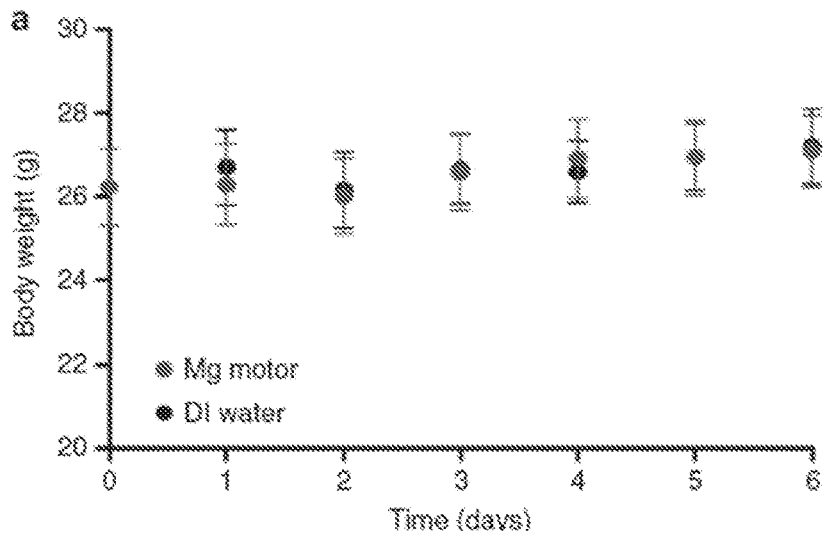
FIGS. 17A and 17B show a data plot and images of an in vivo toxicity evaluation of the example Mg-based micromotors
Figure 17B:
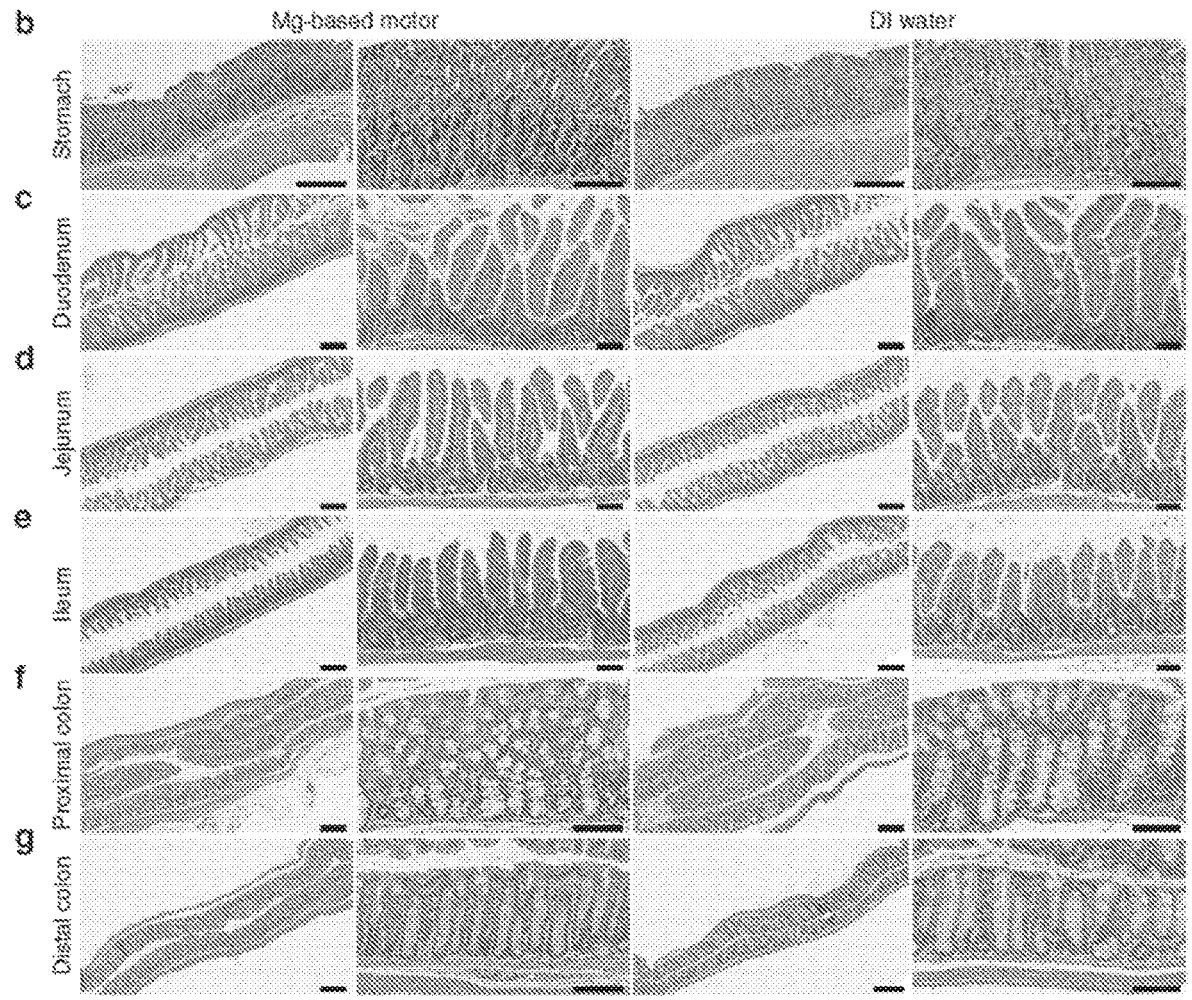

FIGS. 17A and 17B show a data plot and images of an in vivo toxicity evaluation of the example Mg-based micromotors 1110. Uninfected mice were orally administered with the Mg-based micromotors 1110 or DI water once daily for five consecutive days. As shown in FIG. 17A, the data plot depicts the mouse body weight log from day 0 to day 6 of the toxicity study. Error bars of FIG. 17A represent the standard deviation of the mean (n=6). On day 6, mice were killed and sections of the mouse GI tract were examined. FIG. 17B shows images of the examined mouse GI tract for the stomach (panel b), small intestine tissue (panels c-e) and large intestine tissues (panels f-g), which were processed for histological staining with hematoxylin and eosin (H&E). The scale bars of FIG. 17B include 250 and 100 μm for the left and right columns, respectively, under the Mg-based motor images; and 250 and 100 μm for the left and right columns, respectively, for the DI water images.

Example methods include the following.

Synthesis of Example Mg-Based Micromotors. The example Mg-based micromotors were prepared using magnesium (Mg) microparticles (e.g., average size, 20±5 μm) as the core. The example Mg microparticles were initially washed with acetone to eliminate the presence of impurities. After being dried under a $N_2$ current, the example Mg microparticles were dispersed onto glass slides (e.g., 2 mg of Mg microparticles per glass slide), followed by atomic layer deposition (ALD) of $TiO_2$ (e.g., at 100° C. for 120 cycles) using a Beneq TFS 200 system. Since such an ALD process utilizes gas phase reactants, it leads to uniform coatings over the Mg microparticles, while still leaving a small opening at the contact point of the particle to the glass slide. After that, the Janus micromotors were coated with 120 μL of 1% (w/v) PLGA (Sigma-Aldrich, P2191) prepared in ethyl acetate (Sigma-Aldrich, 270989) and containing 40 mg mL$^{-1}$ clarithromycin (CLR) (TCI CO., LTD. C220). It should be noted that different CLR amounts (e.g., between 4 mg and 6 mg) were tested in order to optimize the drug loading. The PLGA@CLR coating was dried fast to avoid crystallization of the drug. The example Janus micromotors were coated with a thin layer of 0.05% (w/v) Chit (Sigma-Aldrich, C3646) prepared in water and containing 0.1% (w/v) sodium dodecyl sulfate (SDS) (Sigma-Aldrich, 62862) and 0.02% (v/v) acetic acid (Sigma-Aldrich, 695092), forming the outermost layer coated on the Mg microparticles. The example Mg-based micromotors were collected by lightly scratching the microparticles off the glass slide.

Synthesis of Dye-Loaded Mg-Based Micromotors. For performing the characterization of the example Mg-based micromotors along with the in vivo retention studies, fluorescent Mg-based micromotors were prepared by combining both 1% PLGA and 0.05% Chit solutions with 5 μg mL$^{-1}$ 1,1'-dioctadecyl-3,3,3',3'-tetramethylindodicarbocyanine, 4-chlorobenzenesulfonate salt (DiD, $\lambda_{ex}$=644 nm/$\lambda_{em}$=665 nm, Life Technologies, D7757) and 1 μg mL$^{-1}$ fluorescein isothiocyanate-dextran (FITC, $\lambda_{ex}$=492 nm/$\lambda_{em}$=520 nm, Sigma-Aldrich, 46945) dyes, respectively. To compare with the Mg-based micromotors, for example, inert silica (Si) microparticles (Nanocs, Inc., Cat. No. Si01-20u-1; 20 μm size) were used as core particles, following the same protocol described above.

Micromotor Characterization. Bright field and fluorescent images of the Mg-based micromotors and inert silica microparticles (shown in FIG. 17) were captured using a EVOS FL microscope coupled with a 20× and 40× microscope objectives and fluorescence filters for red and green light excitation. Scanning electron microscopy (SEM) images of the Mg-based micromotors were obtained with a Phillips XL30 ESEM instrument, using an acceleration voltage of 10 kV. Energy-dispersive X-ray mapping analysis was performed using an Oxford EDX detector attached to SEM instrument and operated by *INCA* software.

Figure 18:
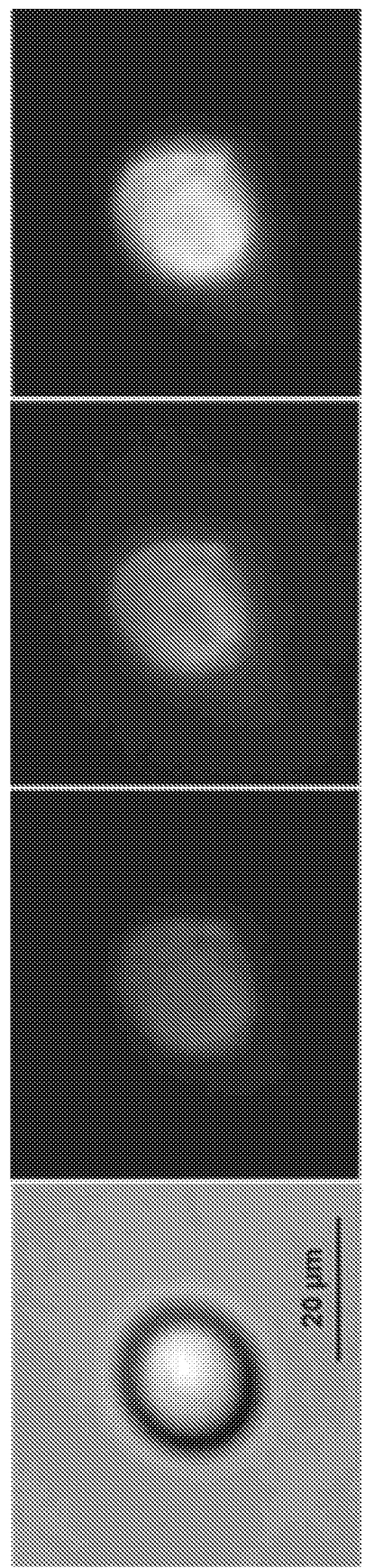
FIG. 18 shows images characterizing example dye-loaded Chit/PLGA silica Janus microparticles.

FIG. 18 shows images characterizing dye-loaded Chit/PLGA silica Janus microparticles. Microscopy images of dye-loaded Chit/PLGA/Si Janus microparticles: optical image, and fluorescence images showing the dye-loaded Si-based Janus microparticles in DiD channel, FITC-D channel, and overlay of the two channels.

Micromotor Propulsion Studies. Autonomous Mg-based micromotors propulsion in simulated gastric fluid (Sigma-Aldrich, 01651) was obtained by diluting 25 times the simulated gastric fluid according to the commercial specifications (final pH~1.3), and adding 1% Triton X-100 (Fisher Scientific, FairLawn, NJ) as surfactant. An inverted optical microscope (Nikon Eclipse 80i upright microscope) coupled with different microscope objectives (10×, 20× and 40×) and a QuantEM:512SC camera were used for recording the autonomous micromotor propulsion in the gastric fluid simulant. The speed of the Mg-based micromotors was characterized using the MetaMorph 7.1 software (Molecular Devices, Sunnyvale, CA).

In Vitro Anti-*H. pylori* Activity. *H. pylori* Sydney strain 1 (HPSS1) was cultured from frozen stock and routinely maintained on Columbia agar supplemented with 5% (vol/vol) laked horse blood at 37° C. under microaerobic conditions (e.g., 10% $CO_2$, 85% $N_2$, and 5% 02). For example, broth cultures of *H. pylori* were prepared by subculturing fresh colonies from agar plates into Brain heart infusion (BHI) supplemented with 5% fetal bovine serum (FBS) and incubated overnight at 37° C. under microaerobic conditions with moderate reciprocal shaking. An overnight broth culture of *H. pylori* was centrifuged at 5000 g for 10 min to obtain a bacterial pellet. After removal of culture medium by centrifugation, the obtained bacteria pellet was then suspended in an appropriate amount of fresh BHI with 5% FBS for future use.

The bactericidal activity against *H. pylori* of free CLR and CLR-loaded Mg-based micromotors (PLGA@CLR/$TiO_2$/Mg) were tested in vitro. Samples were treated in 0.1 N HCl for 1 h and serially diluted to desired concentrations with PBS. Bare Mg-based micromotors (PLGA/$TiO_2$/Mg) with corresponding amount of micromotors were used as negative control.

The samples were added with $1\times10^6$ CFU/mL *H. pylori* in BHI with 5% FBS to make final concentrations of 0-16 μg/mL CLR, followed by incubation at 37° C. under microaerobic conditions with moderate reciprocal shaking for 24 h. Then a series of 10-fold dilutions of the bacterial suspension was prepared, and inoculated onto a Columbia agar plates supplemented with 5% laked horse blood. The plates were cultured for 4 days before the colony-forming unit (CFU) of *H. pylori* was quantified. All example measurements were made in triplicate.

In Vivo Micromotor Retention. Prior to the example experiments, C57BL/6 mice (n=3) were fed with alfalfa-free food from LabDiet (St. Louis, MO, USA) for 2 weeks. The example in vivo retention study was performed by using dye-loaded Mg-based micromotors prepared by the protocol described above. A 0.3 mL suspension of Mg-based micromotors with DiD-labeled PLGA and FITC-labeled chitosan coatings were intragastrically administered. A group of mice was administered with DI water as a negative control. Following 30 min and 2 h of oral administrations, the mice were sacrificed and their entire stomachs were excised and cut opened along the greater curvature. Then, the tissues were rinsed with PBS, flattened, and visualized using a Keyence BZ-X700 fluorescence microscope. The bright field and corresponding fluorescence images were obtained at 665 nm and 520 nm (DiD and FITC, respectively) for each sample. Subsequently, the tissues were transferred to 1 mL PBS and homogenized. Analysis of the amount of micromotors retained in the stomachs was carried out by measuring the fluorescence intensity of their embedded DiD-labeled PLGA and FITC-labeled chitosan using Synergy Mx fluorescent spectrophotometer (Biotek, Winooski, VT).

In Vivo Therapeutic Efficacy Against *H. pylori* Infection. Six-week-old C57BL/6 male mice were obtained from the Jackson Laboratory (Bar Harbor, ME). Each C57BL/6 mouse received 0.3 mL of $1\times10^9$ CFU/mL *H. pylori* in BHI broth administered intragastrically through oral gavage every 48 h, repeated three times (on day 3, 5 and 7, respectively), and the infection was allowed to develop for 2 weeks. For the example in vivo anti-*H. pylori* therapeutic study, mice were randomly divided in five treatment groups (n=6) to be orally administered with CLR-loaded Mg-based micromotors, CLR-loaded inert silica microparticles, free CLR+PPI, blank Mg-based micromotors or DI water. For free CLR+PPI group, mice were first administered with omeprazole (a proton pump inhibitor) through oral gavage at a dose of 400 μmol/kg, followed by a lag time of 30 min before administration of CLR. CLR-loaded Mg-based micromotors, CLR-loaded inert silica microparticles and free CLR (with 30 mg/kg clarithromycin dosage) were administered through oral gavage once daily for 5 consecutive days. Blank Mg-based micromotors and DI water served as movement control and negative control, respectively. Forty-eight hours after last administration, mice were sacrificed and stomachs were excised from the abdominal cavity. The stomachs were cut along the greater curvature, and the gastric content were removed and rinsed with PBS. For *H. pylori* recovery, each gastric tissue was weighed before suspended in 200 μL PBS and homogenized. The homogenate was serially diluted and spotted onto Columbia agar plate with 5% laked horse blood and Skirrow's supplement (e.g., 10 μg/mL vancomycin, 5 μg/mL trimethoprim lactate, 2,500 IU/L polymyxin B; Oxiod). The plates were then incubated at 37° C. under microaerobic conditions for 5 days, and bacterial colonies were enumerated. Statistical analysis was performed using one-way ANOVA. No statistical methods were used to predetermine sample size. The example studies were done in a non-blinded fashion. Replicates represent different mice subjected to the same treatment (n=6).

Toxicity Evaluation of Mg-Based Micromotors. To evaluate the acute toxicity of the Mg-based micromotors in vivo, uninfected C57BL/6 male mice were orally administered with CLR-loaded micromotors once daily for 5 consecutive days. Mice administered with DI water were tested in parallel as a negative control. On day 6, mice were sacrificed and sections of the mouse stomach tissue were processed for histological examination. The longitudinal sections of gastric tissue were fixed in neutral-buffered 10% (vol/vol) formalin for 15 h, transferred into 70% ethanol, and embedded in paraffin. The tissue sections were cut with 5 μm thickness and stained with hematoxylin and eosin (H&E) assay. Sections were visualized by Hamamatsu NanoZoomer 2.0HT and the images processed using NDP viewing software.

The example study evaluates the therapeutic efficacy of a drug-loaded Mg-based micromotor for in vivo treatment of *H. pylori* infection in a mouse model. The example in vivo study results demonstrated that acid-powered Mg-based micromotors could efficiently be loaded with clinical doses of drugs, retain in the mouse stomach wall, and perform effective in vivo bactericidal activity. Example results showed that the active propulsion of drug-loaded Mg-based micromotors in the acidic media of the stomach and motor-tissue interaction lead to efficient drug delivery and hence to a significant reduction of bacteria burden compared to passive drug carriers. Furthermore, such drug-loaded micromotors were able to rapidly deplete the protons in the gastric fluid to reach a neutral pH, thereby excluding the use of PPIs for the *H. pylori* infection treatment. It was also demonstrated that there were no toxicological consequences of the micromotors in the mouse models. The example results indicate that micromotors holds great promise for effective and safe therapeutic treatment of gastrointestinal infection. The micromotor-based therapy devices, systems and methods represent an exciting new therapeutic regimen for the treatment of stomach diseases such as *H. pylori* infection.

EXAMPLES

The following examples are illustrative of several embodiments in accordance with the present technology.

Other exemplary embodiments of the present technology may be presented prior to the following listed examples, or after the following listed examples.

In some embodiments in accordance with the present technology (example 1), a micromotor for a gastrointestinal tract includes a micromotor body including a one or more material layers to provide a structure that surrounds a hollow interior region and has an opening to an exterior of the micromotor body; one or more particles including a biocompatible metal element, the one or more particles contained in the interior region of the micromotor body; a coating coupled to the structure of the micromotor body; and a payload material, in which the micromotor is structured to move in a fluid medium of a gastrointestinal system based on a reaction between the one or more particles and a constituent or a condition of the fluid medium, such that the reaction generates bubbles that accelerate out of the opening of the micromotor body to propel the micromotor in the fluid medium.

Example 2 includes the micromotor of example 1, in which the micromotor body is structured to have a shape of a sphere, an oval, a cone, or a tube.

Example 3 includes the micromotor of example 1, in which the condition of the fluid medium to affect the reaction includes a pH condition of the fluid medium, including an acidic pH condition in a pH range of 0.1 to 5, or a neutral pH condition in a pH range of 6 to 8.

Example 4 includes the micromotor of example 1, in which the micromotor is structured to move in the fluid medium based on a reaction between the biocompatible metal element and hydronium ions or water in the fluid medium of the gastrointestinal system to yield ions of the biocompatible metal element and hydrogen gas that forms the bubbles that produce a driving force to propel the micromotor in the fluid medium.

Example 5 includes the micromotor of example 1, in which the one or more particles includes a single particle in the interior region coupled to the one or more material layers of the micromotor body.

Example 6 includes the micromotor of example 1, in which when the coating includes a polymer layer that encapsulates the payload material.

Example 7 includes the micromotor of example 1, in which the one or more particles includes a plurality of particles located within the interior region proximate the opening of the micromotor body.

Example 8 includes the micromotor of example 1, in which when the payload material is attached to the one or more particles contained in the interior region of the micromotor body.

Example 9 includes the micromotor of example 1, in which the biocompatible metal element includes an alkaline earth metal.

Example 10 includes the micromotor of example 1, in which the coating includes an enteric polymer.

Example 11 includes the micromotor of example 1, in which the micromotor body includes an inner layer including gold and an outer layer including a polymer material including poly3,4-ethylenedioxythiophene (PEDOT); the one or more particles includes magnesium, in which the payload material is coupled to the one or more magnesium particles; and the coating includes a polymer.

Example 12 includes the micromotor of example 11, in which the polymer includes an enteric copolymer.

Example 13 includes the micromotor of example 1, in which the one or more particles includes magnesium; the micromotor body includes gold; and the coating includes the payload material embedded within the coating, the coating including a polymer.

Example 14 includes the micromotor of example 12, in which the polymer includes an anionic copolymer including methacrylic acid and ethyl acrylate.

Example 15 includes the micromotor of example 1, in which the one or more particles includes a magnesium particle; the micromotor body includes a titanium oxide ($TiO_2$) layer coated around the magnesium particle; and the coating includes the payload material embedded within the coating, the coating including a polymer.

Example 16 includes the micromotor of example 15, in which the polymer includes poly(lactic-co-glycolic acid) (PLGA).

Example 17 includes the micromotor of example 16, further including an outer covering.

Example 18 includes the micromotor of example 17, in which the outer covering includes chitosan.

Example 19 includes the micromotor of example 1, in which the payload includes a drug.

Example 20 includes the micromotor of example 1, in which the micromotor is embedded in a pill or a capsule.

In some embodiments in accordance with the present technology (example 21), an enteric micromotor includes one or more magnesium particles; a microstructure body including an inner layer including gold and an outer layer including a polymer material including poly3,4-ethylenedioxythiophene (PEDOT), in which the microstructure body is structured to include a hollow interior region to contain the one or more magnesium particles and an opening of the microstructure body into the hollow interior region; a polymer layer coupled to the outer layer; and a payload material contained in the hollow interior region of the microstructure body, in which, when the polymer layer is immersed in a solution at a predetermined neutral pH, the one or more magnesium particles reacts with water in the solution to generate hydrogen to propel the enteric micromotor.

Example 22 includes the enteric micromotor of example 21, in which, when the enteric micromotor is propelled in the solution, the payload material contained in the hollow interior region of the microstructure body is released into the solution.

Example 23 includes the enteric micromotor of example 21, in which the predetermined neutral pH is in a range of approximately 6 to 8.

Example 24 includes the enteric micromotor of example 21, in which the polymer layer includes an anionic copolymer including methacrylic acid and ethyl acrylate.

Example 25 includes the enteric micromotor of example 21, in which the payload material includes a drug.

Example 26 includes the enteric micromotor of example 21, further including an external coating structured to coat the enteric micromotor and to have a configurable thickness that dissolves in an acidic fluid of a stomach region of the gastrointestinal system so as to be timed expose the opening of the enteric micromotor in an intestinal region of the gastrointestinal system having a gastric fluid at the predetermined neutral pH.

In some embodiments in accordance with the present technology (example 27), an enteric micromotor includes a magnesium microsphere; a gold coating affixed to the magnesium microsphere; a polymer layer affixed to the gold coating; and a payload material encapsulated by the polymer layer, in which when the polymer layer is immersed in a solution at or below a predetermined acidic pH, the magnesium microsphere reacts with the acidic solution thereby (i) generating hydrogen to propel the enteric micromotor, (ii) depleting protons in the solution thereby increasing the pH of the solution, and (iii) releasing the payload material from the polymer layer.

Example 28 includes the enteric micromotor of example 27, in which the predetermined acidic pH is in a range of approximately 1 to 3.

Example 29 includes the enteric micromotor of example 27, in which the polymer layer includes an anionic copolymer including methacrylic acid and ethyl acrylate.

Example 30 includes the enteric micromotor of example 27, in which the payload material includes a drug.

In some embodiments in accordance with the present technology (example 31), a chemical-propulsion microstructure device includes a magnesium microsphere; a coating including titanium oxide affixed to the magnesium microsphere, in which the coating includes an opening at one portion of the magnesium microsphere to expose a magnesium surface; a polymer layer affixed to the coating; and a payload material at least partially encapsulated by the polymer layer, in which the chemical-propulsion microstructure device is operable to undergo a chemical reaction between magnesium and acid when the chemical-propulsion microstructure device are placed in an acidic solution.

Example 32 includes the device of example 31, in which the opening provides contact between the magnesium surface and the acid.

Example 33 includes the device of example 31, in which the chemical-propulsion microstructure device includes a Janus microstructure.

Example 34 includes the device of example 31, further including an outer layer over the polymer layer.

Example 35 includes the device of example 34, in which the outer layer includes chitosan.

Example 36 includes the device of example 35, in which the chitosan layer includes a thickness of approximately 100 nm.

Example 37 includes the device of example 31, in which the coating including titanium oxide layer provides a biocompatible shell scaffold to maintain a spherical shape and the opening size during the propulsion of the chemical-propulsion microstructure.

Example 38 includes the device of example 31, in which the payload material includes an antibiotic drug.

Example 39 includes the device of example 38, in which the antibiotic drug includes clarithromycin (CLR).

Example 40 includes the device of example 39, in which the CLR-encapsulated polymer layer.

Example 41 includes the device of example 31, in which the chemical-propulsion microstructure is operable to undergo an acidic gastric environment to deliver antibacterial substances in a gastrointestinal organ without involving proton pump inhibitors (PPIs).

Example 42 includes the device of example 31, in which the chemical reaction generates hydrogen microbubbles to propel the chemical-propulsion microstructure in stomach fluid, such that the opening allows a slow chemical reaction process and gradual dissolution of the magnesium microsphere to prolong life of the chemical-propulsion microstructure.

Example 43 includes the device of example 31, in which the prolonged life of the chemical-propulsion microstructure includes at least 6 minutes.

In some embodiments in accordance with the present technology (example 44), a method for fabricating micromotors includes dispersing particles (e.g., nanospheres, microspheres or other nano- or micro-particles) on an electrically insulative surface; producing Janus microstructures by depositing a coating on the particles (e.g., using atomic layer deposition), in which the deposited coating includes a small opening at a contact region between the particles and the surface; coating a polymer film on the Janus microstructures (in which in some embodiments the polymer film includes an antibiotic payload); and coating an exterior layer over the polymer film on the Janus microstructures to produce micromotors (in which in some embodiments the exterior layer includes a material providing electrostatic adhesion of the micromotors to a biological tissue layer on a wall of the gastrointestinal system).

Example 45 includes the method of example 44, in which the Janus microstructures include the micromotors of any of examples 1-43.

Example 46 includes the method of example 44, further includes collecting the produced micromotors by soft mechanical scratching of the surface to separate the micromotors from the surface, in which the collected chemical-propulsion micromotors include a small opening for chemical reaction between magnesium and acid when the micromotors are placed in an acidic solution.

Example 47 includes the method of example 45, in which the wall of the gastrointestinal system includes a stomach wall.

Example 48 includes the method of example 44, further including mixing the produced micromotors with pill excipients to produce a pill structure of the micromotors.

Example 49 includes the method of example 44, further including filling a capsule structure with the produced micromotors to produce a capsule of the micromotors.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:
1. A micromotor for a gastrointestinal tract, comprising:
a micromotor body including a one or more material layers to provide a structure that surrounds a hollow interior region and has an opening to an exterior of the micromotor body, wherein a first portion of a payload is contained in the hollow interior region;

one or more particles comprising a biocompatible metal element, the one or more particles contained in the hollow interior region of the micromotor body; and a pH sensitive coating coupled to an exterior of the micromotor body, wherein the pH sensitive coating encapsulates a second portion of the payload, wherein:

the payload comprises clarithromycin, the one or more particles includes one or more magnesium particles, and the micromotor body includes gold, and the pH sensitive coating includes a polymer comprising an enteric anionic copolymer including methacrylic acid and ethyl acrylate, or the micromotor body includes titanium oxide ($TiO_2$), and the pH sensitive coating includes an enteric copolymer poly(lactic-co-glycolic acid) (PLGA), wherein the micromotor is structured to move in a fluid medium of a gastrointestinal system based on a reaction between the one or more particles and a constituent or a condition of the fluid medium, wherein the reaction generates bubbles that accelerate out of the opening of the micromotor body to propel the micromotor in the fluid medium, the propelled micromotor releasing the first portion of the payload contained in the hollow interior region, and wherein the reaction causes, via a change in pH, a release of the second portion of the payload from the pH sensitive coating.

2. The micromotor of claim 1, wherein the micromotor body is structured to have a shape of a sphere.

3. The micromotor of claim 1, wherein the condition of the fluid medium to affect the reaction includes a pH condition of the fluid medium, including an acidic pH condition in a pH range of 0.1 to 5, or a neutral pH condition in a pH range of 6 to 8.

4. The micromotor of claim 1, wherein the micromotor is structured to move in the fluid medium based on a reaction between the biocompatible metal element and hydronium ions or water in the fluid medium of the gastrointestinal system to yield ions of the biocompatible metal element and hydrogen gas that forms the bubbles that produce a driving force to propel the micromotor in the fluid medium.

5. The micromotor of claim 1, wherein the one or more particles includes a single particle in the interior region coupled to the one or more material layers of the micromotor body.

6. The micromotor of claim 1, wherein the pH sensitive coating encapsulates the other portion of the payload.

7. The micromotor of claim 1, wherein the one or more particles includes a plurality of particles located within the interior region proximate the opening of the micromotor body.

8. The micromotor of claim 1, wherein when the payload material is attached to the one or more particles contained in the interior region of the micromotor body.

9. The micromotor of claim 1, wherein the micromotor body includes an inner layer comprising the gold and an outer layer comprising a polymer material including poly3,4-ethylenedioxythiophene (PEDOT).

10. The micromotor of claim 1, further comprising an outer covering.

11. The micromotor of claim 10, wherein the outer covering includes chitosan.

12. The micromotor of claim 1, wherein the micromotor is embedded in a pill or a capsule.

13. A micromotor for a gastrointestinal tract, comprising:

a micromotor body including a one or more material layers to provide a structure that surrounds a hollow interior region and has an opening to an exterior of the micromotor body;

one or more particles comprising a biocompatible metal element, the one or more particles contained in the hollow interior region of the micromotor body; and a coating coupled to the structure of the micromotor body, wherein the coating encapsulates a portion of the payload, wherein:

the payload comprises clarithromycin, the one or more particles includes one or more magnesium particles, and the micromotor body includes gold, and the coating includes a polymer comprising an enteric anionic copolymer including methacrylic acid and ethyl acrylate, or the micromotor body includes titanium oxide ($TiO_2$), and the pH sensitive coating includes an enteric copolymer poly(lactic-co-glycolic acid) (PLGA), wherein the micromotor is structured to move in a fluid medium of a gastrointestinal system based on a reaction between the one or more particles and a constituent or a condition of the fluid medium, such that the reaction generates bubbles that accelerate out of the opening of the micromotor body to propel the micromotor in the fluid medium and causes a release of the payload from the coating.

14. The micromotor of claim 13, wherein the micromotor body is structured to have a shape of a sphere.

15. The micromotor of claim 13, wherein the micromotor further comprises:

an outer covering that includes chitosan.

* * * * *

UNITED STATES PATENT AND TRADEMARK OFFICE
CERTIFICATE OF CORRECTION

| | | |
|---|---|---|
| PATENT NO. | : 12,016,948 B2 | Page 1 of 1 |
| APPLICATION NO. | : 16/475894 | |
| DATED | : June 25, 2024 | |
| INVENTOR(S) | : Joseph Wang et al. | |

It is certified that error appears in the above-identified patent and that said Letters Patent is hereby corrected as shown below:

In the Specification

FEDERALLY SPONSORED RESEARCH OR DEVELOPMENT, Column 1, Lines 26-33, delete:
"This invention was made with government support HDTRA1-13-1-0002 and HDTRA1-14-1-0064 awarded by Defense Threat Reduction Agency Joint Science and Technology Office for Chemical and Biological Defense, and under R01DK095168 awarded by the National Institute of Diabetes and Digestive and Kidney Diseases of the National Institutes of Health. The government has certain rights in the invention."

And insert:
--This invention was made with government support under DK095168 awarded by the National Institutes of Health, and under HDTRA1-14-1-0064 and HDTRA1-13-1-0002 awarded by the Defense Threat Reduction Agency, Department of Defense. The government has certain rights in the invention.--

Signed and Sealed this
Tenth Day of February, 2026

John A. Squires
*Director of the United States Patent and Trademark Office*